United States Patent
Ochiya et al.

(10) Patent No.: US 10,544,466 B2
(45) Date of Patent: Jan. 28, 2020

(54) METHOD FOR DIAGNOSING AND TREATING CANCER BRAIN METASTASIS AND DRUG DELIVERY SYSTEM FOR ENABLING PASSAGE THROUGH BLOOD-BRAIN BARRIER

(71) Applicants: GENE TECHNO SCIENCE CO., LTD., Sapporo-shi, Hokkaido (JP); NATIONAL CANCER CENTER, Tokyo (JP); THEORIA Science Inc., Tokyo (JP)

(72) Inventors: Takahiro Ochiya, Tokyo (JP); Naoomi Tominaga, Tokyo (JP)

(73) Assignees: Gene Techno Science Co., Ltd., Sapporo-shi, Hokkaido (JP); National Cancer Center, Tokyo (JP); Theoria Science Inc., Tokyo (JP)

( * ) Notice: Subject to any disclaimer, the term of this patent is extended or adjusted under 35 U.S.C. 154(b) by 0 days.

(21) Appl. No.: 15/552,766

(22) PCT Filed: Feb. 24, 2015

(86) PCT No.: PCT/JP2015/000906
§ 371 (c)(1),
(2) Date: Aug. 22, 2017

(87) PCT Pub. No.: WO2016/135772
PCT Pub. Date: Sep. 1, 2016

(65) Prior Publication Data
US 2018/0274035 A1    Sep. 27, 2018

(51) Int. Cl.
| | | |
|---|---|---|
| *C12N 15/113* | (2010.01) |
| *A61P 25/08* | (2006.01) |
| *A61P 25/00* | (2006.01) |
| *A61P 25/16* | (2006.01) |
| *A61P 25/28* | (2006.01) |
| *C12Q 1/6886* | (2018.01) |
| *A61P 35/04* | (2006.01) |

(52) U.S. Cl.
CPC ............ *C12Q 1/6886* (2013.01); *A61P 35/04* (2018.01); *C12N 15/113* (2013.01); *A61P 25/00* (2018.01); *A61P 25/08* (2018.01); *A61P 25/16* (2018.01); *A61P 25/28* (2018.01); *C12N 2310/141* (2013.01); *C12Q 2600/158* (2013.01); *C12Q 2600/178* (2013.01)

(58) Field of Classification Search
CPC ............ C12N 15/113; C12N 2310/141; C12Q 2600/178; A61K 31/7088; A61K 45/00; A61P 35/04
See application file for complete search history.

(56) References Cited

U.S. PATENT DOCUMENTS

| | | | | |
|---|---|---|---|---|
| 8,258,111 B2 * | 9/2012 | Shen | ............. | C12N 15/113 |
| | | | | 435/320.1 |
| 8,697,663 B2 * | 4/2014 | Bennett | ............. | C12N 15/111 |
| | | | | 514/44 A |
| 2010/0137411 A1 * | 6/2010 | Green | ............. | C12N 15/111 |
| | | | | 514/44 A |
| 2010/0216767 A1 * | 8/2010 | Aikawa | ............. | C07D 239/84 |
| | | | | 514/210.21 |
| 2011/0064792 A1 | 3/2011 | Humphries et al. | | |
| 2017/0369878 A1 * | 12/2017 | Lu | ............. | C12N 15/111 |

FOREIGN PATENT DOCUMENTS

| | | |
|---|---|---|
| JP | 2011-501662 A | 1/2011 |
| WO | WO 2009/047362 A2 | 4/2009 |
| WO | WO 2012/135844 A2 | 10/2012 |
| WO | WO 2013/107460 A2 | 7/2013 |

OTHER PUBLICATIONS

Das S et al. miR-181c regulates the mitochondrial genome, bioenergetics, and propensity for heart failure in vivo. PLoS ONE, May 2014, 9(5):e96820. (Year: 2014).*
Li Y et al. MiR-181c modulates the proliferation, migration, and invasion of neuroblastoma cells by targeting Smad7. Acta Biochim. Biophys. Sin. 2014, 46:48-55. (Year: 2014).*
Ruan J et al. Tumor suppressor miR-181c attenuates proliferation, invasion, and self-renewal abilities in glioblastoma. NeuroReport, 2015, 26:66-73 (Year: 2015).*
Ma Q et al. MicroRNA-181c exacerbates brain injury in acute ischemic stroke. Aging and DIsease, 7(6):705-714. (Year: 2016).*
Zhang L et al. The microRNA miR-181c controls microglia-mediated neuronal apoptosis by suppressing tumor necrosis factor. J. Neuroinflammation, 9:211. (Year: 2012).*
International Search Report and Written opinion of the International Searching Authority for International Application No. PCT/JP2015/000906, dated May 19, 2015, in 10 pages.
Arshad et al., "Blood-Brain Barrier Integrity and Breast Cancer Metastasis to the Brain," *Pathology Research International*, vol. 2011, Article ID 920509, 12 pages (2010).
Camacho et al., "MicroRNA and Protein Profiling of Brain Metastasis Competent Cell-Derived Exosomes," *PLOS ONE*, vol. 8(9), #e73790 (Sep. 2013).
Chen et al., "Cryptococcus neoformans induces alterations in the cytoskeleton of human brain microvascular endothelial cells," *Journal of Medical Microbiology*, vol. 52, pp. 961-970 (2003).
Chen et al., "Upregulation of miR-181c contributes to chemoresistance in pancreatic cancer by inactivating the Hippo signaling pathway," *Oncotarget*, vol. 6(42), pp. 44466-44479 (2015).

(Continued)

*Primary Examiner* — Kimberly Ballard
(74) *Attorney, Agent, or Firm* — Knobbe, Martens, Olson & Bear, LLP

(57) ABSTRACT

A method increases permeability of a blood-brain barrier in a subject. The method includes administering a small interfering ribonucleic acid (siRNA) against the 3-Phosphoinositide Dependent Protein Kinase 1 (PDPK1) gene or micro ribonucleic acid (miRNA) miR-181c as an active ingredient to the subject. The method can be applied for delivering a desired active agent to the subject.

2 Claims, 25 Drawing Sheets

Specification includes a Sequence Listing.

(56) References Cited

OTHER PUBLICATIONS

Kosaka et al., "Neutral Sphingomyelinase 2 (nSMase2)-dependent Exosomal Transfer of Angiogenic MicroRNAs Regulate Cancer Cell Metastasis," *J. Biol. Chem.*, vol. 288(15), pp. 10849-10859 (2013).

Lee et al., "Vascular Endothelial Growth Factor Modulates the Transendothelial Migration of MDA-MB-231 Breast Cancer Cells through Regulation of Brain Microvascular Endothelial Cell Permeability," *J Biol Chem*, vol. 278(7), pp. 5277-5284 (Feb. 14, 2003).

Liu et al., "Murine Mammary Carcinoma Exosomes Promote Tumor Growth by Suppression of NK Cell Function," *The Journal of Immunology*, vol. 176, pp. 1375-1385 (2006).

Ostrowski et al., "Rab27a and Rab27b control different steps of the exosome secretion pathway," *Nature Cell Biology*, vol. 12(1), pp. 19-30 (2010); Methods, Supplementary Information.

Peinado et al., "Melanoma exosomes educate bone marrow progenitor cells toward a pro-metastatic phenotype through MET," *Nat Med*, vol. 18(6), pp. 883-891 (2012).

Tominaga et al., Molecular Biology Society of Japan Annual Meeting Program Abstract, vol. 36th, #1P-0824 (2013).

Tominaga et al., "Brain metastatic cancer cells release microRNA-181c-containing extracellular vesicles capable of destructing blood-brain barrier," *Nature Communications*, vol. 6, #6716, doi:10.1038/ncomms7716 (2015).

Valadi et al., "Exosome-mediated transfer of mRNAs and microRNAs is a novel mechanism of genetic exchange between cells," *Nat Cell Biol*, vol. 9(6), pp. 654-659 (Jun. 2007).

Yang et al., "The Roles of Tumor-Derived Exosomes in Cancer Pathogenesis," *Clin Dev Immunol*, vol. 2011, Article ID 842849, 11 pages (2011).

Yano et al., "Expression of Vascular Endothelial Growth Factor Is Necessary but not Sufficient for Production and Growth of Brain Metastasis," *Cancer Research*, vol. 60: pp. 4959-4967 (Sep. 1, 2000).

Notification of Reasons for Refusal received in Japanese Patent Application No. 2017-501541 dated Jan. 8, 2019.

Supplementary Partial European Search Report and Provisional Written Opinion received in connection with European Patent Application No. 15883072.9 dated Aug. 8, 2018.

Zhang, W.-L., and J.-H. Zhang, miR-181c Promotes Proliferation via Suppressing PTEN Expression in Inflammatory Breast Cancer, International Journal of Oncology 46:2011-2020, 2015.

MiRNA Entry for MI0000271, miRBase, www.mirbase.org/cgi-bin/mirna_entry.pl?acc-MI0000271, downloaded Jan. 16, 2019.

Notice of Reasons for Refusal issued in connection with Japanese Patent Application No. 2017-501541 dated Aug. 27, 2019.

* cited by examiner a b c

SEQUENCE LISTING

```
<160> NUMBER OF SEQ ID NOS: 17

<210> SEQ ID NO 1
<211> LENGTH: 22
<212> TYPE: RNA
<213> ORGANISM: Homo sapiens

<400> SEQUENCE: 1
aacauucaac cugucgguga gu                                              22

<210> SEQ ID NO 2
<211> LENGTH: 7243
<212> TYPE: DNA
<213> ORGANISM: Homo sapiens
<220> FEATURE:
<221> NAME/KEY: CDS
<222> LOCATION: (150)..(1820)

<400> SEQUENCE: 2
gcggcgccgg gggcgggggg cggcgggcga cggggcgggc gcaggatgag ggcggccatt       60
gctggggctc cgcttcgggg aggaggacgc tgaggaggcg ccgagccgcg cagcgctgcg      120
ggggaggcgc ccgcgccgac gcggggccc atg gcc agg acc acc agc cag ctg        173
                                 Met Ala Arg Thr Thr Ser Gln Leu
                                   1               5 tat gac gcc gtg ccc atc cag tcc agc gtg gtg tta tgt tcc tgc cca        221
Tyr Asp Ala Val Pro Ile Gln Ser Ser Val Val Leu Cys Ser Cys Pro
     10                  15                  20 tcc cca tca atg gtg agg acc cag act gag tcc agc acg ccc cct ggc        269
Ser Pro Ser Met Val Arg Thr Gln Thr Glu Ser Ser Thr Pro Pro Gly
 25                  30                  35                  40 att cct ggt ggc agc agg cag ggc ccc gcc atg gac ggc act gca gcc        317
Ile Pro Gly Gly Ser Arg Gln Gly Pro Ala Met Asp Gly Thr Ala Ala
                 45                  50                  55 gag cct cgg ccc ggc gcc ggc tcc ctg cag cat gcc cag cct ccg ccg        365
Glu Pro Arg Pro Gly Ala Gly Ser Leu Gln His Ala Gln Pro Pro Pro
             60                  65                  70 cag cct cgg aag aag cgg cct gag gac ttc aag ttt ggg aaa atc ctt        413
Gln Pro Arg Lys Lys Arg Pro Glu Asp Phe Lys Phe Gly Lys Ile Leu
         75                  80                  85
```

```
ggg gaa ggc tct ttt tcc acg gtt gtc ctg gct cga gaa ctg gca acc    461
Gly Glu Gly Ser Phe Ser Thr Val Val Leu Ala Arg Glu Leu Ala Thr
     90              95                 100 tcc aga gaa tat gcg att aaa att ctg gag aag cga cat atc ata aaa    509
Ser Arg Glu Tyr Ala Ile Lys Ile Leu Glu Lys Arg His Ile Ile Lys
105                 110                 115                 120 gag aac aag gtc ccc tat gta acc aga gag cgg gat gtc atg tcg cgc    557
Glu Asn Lys Val Pro Tyr Val Thr Arg Glu Arg Asp Val Met Ser Arg
                125                 130                 135 ctg gat cac ccc ttc ttt gtt aag ctt tac ttc aca ttt cag gac gac    605
Leu Asp His Pro Phe Phe Val Lys Leu Tyr Phe Thr Phe Gln Asp Asp
        140                 145                 150 gag aag ctg tat ttc ggc ctt agt tat gcc aaa aat gga gaa cta ctt    653
Glu Lys Leu Tyr Phe Gly Leu Ser Tyr Ala Lys Asn Gly Glu Leu Leu
            155                 160                 165 aaa tat att cgc aaa atc ggt tca ttc gat gag acc tgt acc cga ttt    701
Lys Tyr Ile Arg Lys Ile Gly Ser Phe Asp Glu Thr Cys Thr Arg Phe
170                 175                 180 tac acg gct gag att gtg tct gct tta gag tac ttg cac ggc aag ggc    749
Tyr Thr Ala Glu Ile Val Ser Ala Leu Glu Tyr Leu His Gly Lys Gly
185                 190                 195                 200 atc att cac agg gac ctt aaa ccg gaa aac att ttg tta aat gaa gat    797
Ile Ile His Arg Asp Leu Lys Pro Glu Asn Ile Leu Leu Asn Glu Asp
                205                 210                 215 atg cac atc cag atc aca gat ttt gga aca gca aaa gtc tta tcc cca    845
Met His Ile Gln Ile Thr Asp Phe Gly Thr Ala Lys Val Leu Ser Pro
        220                 225                 230 gag agc aaa caa gcc agg gcc aac tca ttc gtg gga aca gcg cag tac    893
Glu Ser Lys Gln Ala Arg Ala Asn Ser Phe Val Gly Thr Ala Gln Tyr
            235                 240                 245 gtt tct cca gag ctg ctc acg gag aag tcc gcc tgt aag agt tca gac    941
Val Ser Pro Glu Leu Leu Thr Glu Lys Ser Ala Cys Lys Ser Ser Asp
250                 255                 260 ctt tgg gct ctt gga tgc ata ata tac cag ctt gtg gca gga ctc cca    989
Leu Trp Ala Leu Gly Cys Ile Ile Tyr Gln Leu Val Ala Gly Leu Pro
265                 270                 275                 280 cca ttc cga gct gga aac gag tat ctt ata ttt cag aag atc att aag   1037
Pro Phe Arg Ala Gly Asn Glu Tyr Leu Ile Phe Gln Lys Ile Ile Lys
                285                 290                 295 ttg gaa tat gac ttt cca gaa aaa ttc ttc cct aag gca aga gac ctc   1085
Leu Glu Tyr Asp Phe Pro Glu Lys Phe Phe Pro Lys Ala Arg Asp Leu
        300                 305                 310 gtg gag aaa ctt ttg gtt tta gat gcc aca aag cgg tta ggc tgt gag   1133
Val Glu Lys Leu Leu Val Leu Asp Ala Thr Lys Arg Leu Gly Cys Glu
            315                 320                 325 gaa atg gaa gga tac gga cct ctt aaa gca cac ccg ttc ttc gag tcc   1181
Glu Met Glu Gly Tyr Gly Pro Leu Lys Ala His Pro Phe Phe Glu Ser
330                 335                 340 gtc acg tgg gag aac ctg cac cag cag acg cct ccg aag ctc acc gct   1229
Val Thr Trp Glu Asn Leu His Gln Gln Thr Pro Pro Lys Leu Thr Ala
345                 350                 355                 360 tac ctg ccg gct atg tcg gaa gac gac gag gac tgc tat ggc aat tat   1277
Tyr Leu Pro Ala Met Ser Glu Asp Asp Glu Asp Cys Tyr Gly Asn Tyr
                365                 370                 375 gac aat ctc ctg agc cag ttt ggc tgc atg cag gtg tct tcg tcc tcc   1325
Asp Asn Leu Leu Ser Gln Phe Gly Cys Met Gln Val Ser Ser Ser Ser
        380                 385                 390 tcc tca cac tcc ctg tca gcc tcc gac acg ggc ctg ccc cag agg tca   1373
Ser Ser His Ser Leu Ser Ala Ser Asp Thr Gly Leu Pro Gln Arg Ser
            395                 400                 405
```

```
ggc agc aac ata gag cag tac att cac gat ctg gac tcg aac tcc ttt    1421
Gly Ser Asn Ile Glu Gln Tyr Ile His Asp Leu Asp Ser Asn Ser Phe
        410                 415                 420 gaa ctg gac tta cag ttt tcc gaa gat gag aag agg ttg ttg ttg gag    1469
Glu Leu Asp Leu Gln Phe Ser Glu Asp Glu Lys Arg Leu Leu Leu Glu
425                 430                 435                 440 aag cag gct ggc gga aac cct tgg cac cag ttt gta gaa aat aat tta    1517
Lys Gln Ala Gly Gly Asn Pro Trp His Gln Phe Val Glu Asn Asn Leu
                    445                 450                 455 ata cta aag atg ggc cca gtg gat aag cgg aag ggt tta ttt gca aga    1565
Ile Leu Lys Met Gly Pro Val Asp Lys Arg Lys Gly Leu Phe Ala Arg
                460                 465                 470 cga cag ctg ttg ctc aca gaa gga cca cat tta tat tat gtg gat        1613
Arg Gln Leu Leu Leu Thr Glu Gly Pro His Leu Tyr Tyr Val Asp
        475                 480                 485 cct gtc aac aaa gtt ctg aaa ggt gaa att cct tgg tca caa gaa ctt    1661
Pro Val Asn Lys Val Leu Lys Gly Glu Ile Pro Trp Ser Gln Glu Leu
        490                 495                 500 cga cca gag gcc aag aat ttt aaa act ttc ttt gtc cac acg cct aac    1709
Arg Pro Glu Ala Lys Asn Phe Lys Thr Phe Phe Val His Thr Pro Asn
505                 510                 515                 520 agg acg tat tat ctg atg gac ccc agc ggg aac gca cac aag tgg tgc    1757
Arg Thr Tyr Tyr Leu Met Asp Pro Ser Gly Asn Ala His Lys Trp Cys
                    525                 530                 535 agg aag atc cag gag gtt tgg agg cag cga tac cag agc cac ccg gac    1805
Arg Lys Ile Gln Glu Val Trp Arg Gln Arg Tyr Gln Ser His Pro Asp
                540                 545                 550 gcc gct gtg cag tga cgtggcctgc ggccgggctg cccttcgctg ccaggacacc    1860
Ala Ala Val Gln
            555 tgccccagcg cggcttggcc gccatccggg acgcttccag accacctgcc agccatcaca    1920 aggggaacgc agaggcggaa accttgcagc attttttattt aaaagaaaag aagaaaaaaa    1980 acacccaacc acacaaagaa caaaaccagt aacaaacaca aaggaattca gggtcgcttt    2040 gcttgctctc tgtgctccgt ggaggcctcc gtgtgccctc gttgccgtgg ggacccagct    2100 ccatgcacgt caacccagtc ccgcccagac tagtggacag acctggtgtc accagttttt    2160 cctagcatca gtccgaacca tgcgcccgcc ctgccccaac tgtgtgctgg tcctgctgtg    2220 gccgagggga ccgggtgtgt ttggctcttt atgcccctcc cgctgtggtc ctggaactct    2280 tcaccaggga gggagccctg cggggccgc agctttgtgg agggagccgc cgtgcttctg    2340 tcacctgctc cctttcttgc gtctcccgt gatgggccct taggcctggc tgggcccatt    2400 acatatccct gtggtggctc tggtggcagc tttctgtggc ccctgctgtg ttggcaggca    2460 ggtttgcgtg gtgaggagcg ggaggggttg gagtggtgcg ggagcaggct gccgagtgga    2520 gggtgccatc gagggctccg gatcccttat cctacttagc agtgttggtc tctggggctg    2580 gaagccgagc gcatgctggg agcggtactg tcagaagtga gcccagttag taccccgctg    2640 gctcactgca cgagagagtc ctgccccgag ccctaggtgg ggccaggagg tgccttggag    2700 aagccagcca gagcagagag ggctgctgac ttccgtgtgg agcagagagg cctgagggcc    2760 tcctaaaagg tttaaatgtc cacgcctctc cagttgctga agtagggtct gagagaaccc    2820 tggcatcagc agacccaggg tgcttctgtc tcctgcagac cacgccaggg agtgcagaca    2880 ccaccgtcac acacgcccct tttgtgtttt ggttcaagtt tctcagagcc cctcagagct    2940 tctacatctg tgcatcagaa atctcacagc cttctcatgc tgccggctca tctgggccca    3000 tagagtgggc tttgccagtt gctgttgcac aggaggcgag aacagcacac ttcaacccca    3060
```

```
gcttgctggt cggctttcct ctagagagag ccggttttgg ggccatttcc ctttgatgct    3120
ttggtggcct tgccccgctc tgcagcacag acaggccaga tgcatttgtc ctttgcctag    3180
ctactcccca ggtagagagt gctcctggtg gcctggcagg tctgggccct tctctccctg    3240
cccaggttgt ccctggaggg cagccctcac tcccttgggg ggagaggcag acattgctgc    3300
ccacagacct gcctctgact caactgtgtc caccctccct ggtccctacc cccaagtcac    3360
aggtgactca gcagtgaccc tgtgtgccag gccagatcca aactgagagg gaaggtgtcg    3420 ttttttacact gctaatgacg agagtggctc tttttagcta ggcgagtaca gacggggcct    3480 gggaggggc agagatgttc cccaggccct gcctgtggtt cctgcctggg ccttggctgc     3540
tgctgtgtga gagctgcatg tgagcctgtg accgtgagct ggggtgagct gggccgcacc    3600
taccctgggg ccccagggag caggacgctc cggggcccag cacgttgccc tgggcctgtg    3660
gccggagtcg gagtcctctc tcctcctcct ggcttttgga aaggcttggc tgtgttgggg    3720
agtctctctt agccctttca ggaatttctg ttcaggcttc ctcctcctca tcagctattt    3780
tacccatctc agaacgtcct gtgtctccat gtaggagagt ggctctctca gatctctcag    3840
ggcgtctggt tatagggaaa caagtggagc agggacgtgg ctttaattgg agcactcggc    3900
tgggctgctt ggggagactc ttccgtgcgt tcttcctctg gatagaacca ccacctcctg    3960
ggcgtcactg acaagctcca tcttaacctc caaagccaca gaactagggg ctcagagcca    4020
gagctggcag ccgccagcca aaatgatgcc attgcctgag ctgacagcca gcccttctg    4080 tgggtcacct ttctcctcac ccagccccttt gctcttccct tttgaaaggc ccgtgtgttt    4140
tctttcctta ccctgtgctt gctcatgtct actccggttt tctctaccac atccttagag    4200
ccatcacctg gcacgcaggc gccttacatt ctacggtaga acgtggggta ctgtgtgtgc    4260
acatagacac acttacgtgg aattacagtt gtgggtttat ccaagatgag gaagatttca    4320
cctgctgttt aatagacttg gggccatgtg cctccccaca catgggcaag gacaggtgga    4380
atgtcgggac cacactgtgc ggcttctcgg cacaaagcgg agggaggctg tggtcgctgc    4440
cggcctaggt gtcccaggtg ccccgccttt ctctgggaca cagttggggg ctggcttctg    4500
agggattcct ttctcccctc tttgtgtggc cccagccagg gcggtgggca gtcctggtgt    4560
agagcacaag cctctccacc ctagagaaat gcctctgtac cacggctacc atgtggaacc    4620
ttaacttgca gaaggcttgt taacaattgt tttgagagag atggctggtc atgccacagc    4680
tgctggggac tccgcctact ccagccctct tgggacacac tgtgggattt gtggcccttc    4740
cccagaggaa ttgtggagac tgtcccatgg aacaaaccct caggcaccag cacagggctc    4800
tgggtgactc agtaaaacta acgtttgtct ctgacaagat cagctgtagg ctcaccggcc    4860
agagaagacc actgtgagca ttttgccgta tatcctgccc tgccatttgt tcacttttta    4920
aactaaaata ggaacatccg acacacaccg tttgcatcgt cttctcccett gatatttaa    4980 gcatttcccc atgtcatgag tttctcagaa acatgttttt aacaattgta ctatttagtc    5040
attgtccatt tactataatt tatctgacca tttcccctact gtaaaatact taagacggtt    5100
tctgattttt ccactatttta aataatgctg tgatgaatat cttttaaaatc ttctgatttc    5160 ttactttttt cccccttaga tgcctggaag tggtattttg aggtgaaaga gtttgttcat    5220
tttgaagata tttctgtctc tctctcgacc tgatgtgtag acgctcactt ccagtagcag    5280 aaccaccta gttgtgtctt acagattctg aacaaatcgg tttctgataa gccatgtgtt    5340
ccaaagaatg tctgaataag accgctctttt atttaaatgc taagaggatg tcactactgc    5400
aatccatctg tggccgattt tttccaagag ccaatttcct tgttttggtt gcaagaacct    5460
```

-continued

```
ggctctgcct gcatgtcagc tctctgccct ccctgctgcc gtggctttca agcgcttggc    5520
agaatcttgt acttcgtgtc cacaatggta ctgaatttgc atctgcacag tcagcagaga    5580
taacaagtgt tgaactgacc ttgccacatg cttagtgagt gatttgtaat taagtttata    5640
gactcagaag gtatattagg acatttggaa tcagtagcag agcaaagcct ctttgaaaaa    5700
aaccacgtag ctgattgggt tttacaagag tgcatttgtc tcccccttcc acccgtgggg    5760
ccccaccttc aggtcttagt ggttcacaag agcccagcag ccaggctggc ttttcattg     5820 tagggcgtgg ttgtcccagc tggtgtagat ttcaggccgc ccccccaac tccctgccca     5880 cagtgttgca gattgcctgg ctggcagcaa gtccagacca cccaaatttg gttggattct    5940
tcatttctcc actgtagttg gggtccattg attgtgcagg ggaacgtgca ggaggttttt    6000
ctaggcaccg tgttcagtgc tgcttcactc taccagagat tatggccaaa ttgcacggaa    6060
tttggtttct tgccctctga agcctgaggg ccccccttg cctggctggt tgacagaccc     6120
ggggtggtca ctgctgagac ttcagagatc gcagctgctg tgagaatacg gtgaaggtac    6180
tttgttctgg aagatgttgt catacacttt tccccagtta ttttcaaact tgacatgagc    6240
ctatgttgac tcactgggtg ggggtcccctt cttacgcagc acacgtggca agtgcctgaa    6300
tcggggctgg aggcacttca gagcctctga ggggccacca cttctggccc aaaattgcag    6360
ggttgtagat gaggctgcct gtggagaact ggtgtgagga ggaagctgtt tccaacaaag    6420
agcactttca tctgttgaga tggctgtggt gagcaactga acgagcctac gtgtgtacct    6480
gaattttccc cgtaactcat ttcttccata tgaagaaaca ccaaactatg tacagagaac    6540 ttttttacaaa aggcagacct ttttttaagct gtgtaaccca catagcctaa ccacctggca   6600
gaatgactac gaatagggggt cattgtgctg gtaaaagcct ctattacgac tgtaagtaag   6660
ttggatgttg gcaaaattaa attgttacag tatttagagc tgctgtagct gttccttcac    6720
aacataaaat aggataaatg actagtacgt ctttcaggtg ggtggcaagc agaacatgcg    6780
taatattctc tacctggtct gtagctgtaa ctgtgatgta cagacaaagc aaaaattaaa    6840
agaacttatg aaaacaaatg caatgatact aggatataca cttttgtatt tttattctta    6900
tataaggtta tttgctggct attgttggcc tctagttcag tctgtgttat ttaaattcta    6960
atatatgaat tatttgaatt gaattcatgt tcggggccac gttgttgtat gtattgatgt    7020
acagccttga atgtgaataa ttattgtaaa ctatatttta caacttttttt tctggcttta    7080 ttatataaat tttctattgg gtcagtgatt taatcatata atttaatgaa tctgtttatc    7140 ctttttttt ttccaaatac ttgtgcttta ggtgtagtta ccagatgatg aattttcctc     7200
gtatggtcag tagtcttgta ataaaaagca tgtagagtgt aga                       7243
```

<210> SEQ ID NO 3
<211> LENGTH: 556
<212> TYPE: PRT
<213> ORGANISM: Homo sapiens

<400> SEQUENCE: 3

```
Met Ala Arg Thr Thr Ser Gln Leu Tyr Asp Ala Val Pro Ile Gln Ser
 1               5                  10                  15

Ser Val Val Leu Cys Ser Cys Pro Ser Pro Ser Met Val Arg Thr Gln
            20                  25                  30

Thr Glu Ser Ser Thr Pro Pro Gly Ile Pro Gly Gly Ser Arg Gln Gly
        35                  40                  45

Pro Ala Met Asp Gly Thr Ala Ala Glu Pro Arg Pro Gly Ala Gly Ser
    50                  55                  60
```

-continued

```
Leu Gln His Ala Gln Pro Pro Gln Pro Arg Lys Lys Arg Pro Glu
 65                  70                  75                  80

Asp Phe Lys Phe Gly Lys Ile Leu Gly Glu Gly Ser Phe Ser Thr Val
                 85                  90                  95

Val Leu Ala Arg Glu Leu Ala Thr Ser Arg Glu Tyr Ala Ile Lys Ile
                100                 105                 110

Leu Glu Lys Arg His Ile Ile Lys Glu Asn Lys Val Pro Tyr Val Thr
                115                 120                 125

Arg Glu Arg Asp Val Met Ser Arg Leu Asp His Pro Phe Phe Val Lys
                130                 135                 140

Leu Tyr Phe Thr Phe Gln Asp Asp Glu Lys Leu Tyr Phe Gly Leu Ser
145                 150                 155                 160

Tyr Ala Lys Asn Gly Glu Leu Leu Lys Tyr Ile Arg Lys Ile Gly Ser
                165                 170                 175

Phe Asp Glu Thr Cys Thr Arg Phe Tyr Thr Ala Glu Ile Val Ser Ala
                180                 185                 190

Leu Glu Tyr Leu His Gly Lys Gly Ile Ile His Arg Asp Leu Lys Pro
                195                 200                 205

Glu Asn Ile Leu Leu Asn Glu Asp Met His Ile Gln Ile Thr Asp Phe
210                 215                 220

Gly Thr Ala Lys Val Leu Ser Pro Glu Ser Lys Gln Ala Arg Ala Asn
225                 230                 235                 240

Ser Phe Val Gly Thr Ala Gln Tyr Val Ser Pro Glu Leu Leu Thr Glu
                245                 250                 255

Lys Ser Ala Cys Lys Ser Ser Asp Leu Trp Ala Leu Gly Cys Ile Ile
                260                 265                 270

Tyr Gln Leu Val Ala Gly Leu Pro Pro Phe Arg Ala Gly Asn Glu Tyr
                275                 280                 285

Leu Ile Phe Gln Lys Ile Ile Lys Leu Glu Tyr Asp Phe Pro Glu Lys
                290                 295                 300

Phe Phe Pro Lys Ala Arg Asp Leu Val Glu Lys Leu Leu Val Leu Asp
305                 310                 315                 320

Ala Thr Lys Arg Leu Gly Cys Glu Glu Met Glu Gly Tyr Gly Pro Leu
                325                 330                 335

Lys Ala His Pro Phe Phe Glu Ser Val Thr Trp Glu Asn Leu His Gln
                340                 345                 350

Gln Thr Pro Pro Lys Leu Thr Ala Tyr Leu Pro Ala Met Ser Glu Asp
                355                 360                 365

Asp Glu Asp Cys Tyr Gly Asn Tyr Asp Asn Leu Leu Ser Gln Phe Gly
                370                 375                 380

Cys Met Gln Val Ser Ser Ser Ser Ser His Ser Leu Ser Ala Ser
385                 390                 395                 400

Asp Thr Gly Leu Pro Gln Arg Ser Gly Ser Asn Ile Glu Gln Tyr Ile
                405                 410                 415

His Asp Leu Asp Ser Asn Ser Phe Glu Leu Asp Leu Gln Phe Ser Glu
                420                 425                 430

Asp Glu Lys Arg Leu Leu Leu Glu Lys Gln Ala Gly Gly Asn Pro Trp
                435                 440                 445

His Gln Phe Val Glu Asn Asn Leu Ile Leu Lys Met Gly Pro Val Asp
                450                 455                 460

Lys Arg Lys Gly Leu Phe Ala Arg Arg Arg Gln Leu Leu Leu Thr Glu
465                 470                 475                 480
```

```
Gly Pro His Leu Tyr Tyr Val Asp Pro Val Asn Lys Val Leu Lys Gly
            485                 490                 495

Glu Ile Pro Trp Ser Gln Glu Leu Arg Pro Glu Ala Lys Asn Phe Lys
        500                 505                 510

Thr Phe Phe Val His Thr Pro Asn Arg Thr Tyr Tyr Leu Met Asp Pro
            515                 520                 525

Ser Gly Asn Ala His Lys Trp Cys Arg Lys Ile Gln Glu Val Trp Arg
        530                 535                 540

Gln Arg Tyr Gln Ser His Pro Asp Ala Ala Val Gln
545                 550                 555

<210> SEQ ID NO 4
<211> LENGTH: 6862
<212> TYPE: DNA
<213> ORGANISM: Homo sapiens
<220> FEATURE:
<221> NAME/KEY: CDS
<222> LOCATION: (150)..(1439)

<400> SEQUENCE: 4
gcggcgccgg gggcgggggg cggcgggcga cggggcgggc gcaggatgag ggcggccatt      60 gctgggctc cgcttcgggg aggaggacgc tgaggaggcg ccgagccgcg cagcgctgcg     120
ggggaggcgc ccgcgccgac gcggggccc atg gcc agg acc acc agc cag ctg       173
                                 Met Ala Arg Thr Thr Ser Gln Leu
                                  1               5 tat gac gcc gtg ccc atc cag tcc agc gtg gtg tta tgt tcc tgc cca       221
Tyr Asp Ala Val Pro Ile Gln Ser Ser Val Val Leu Cys Ser Cys Pro
     10              15                  20 tcc cca tca atg gtg agg acc cag act gag tcc agc acg ccc cct ggc       269
Ser Pro Ser Met Val Arg Thr Gln Thr Glu Ser Ser Thr Pro Pro Gly
 25              30                  35                  40 att cct ggt ggc agc agg cag ggc ccc gcc atg gac ggc act gca gcc       317
Ile Pro Gly Gly Ser Arg Gln Gly Pro Ala Met Asp Gly Thr Ala Ala
                 45                  50                  55 gag cct cgg ccc ggc gcc ggc tcc ctg cag cat gcc cag cct ccg ccg       365
Glu Pro Arg Pro Gly Ala Gly Ser Leu Gln His Ala Gln Pro Pro Pro
             60                  65                  70 cag cct cgg aag aag cgg cct gag gac ttc aag ttt ggg aaa atc ctt       413
Gln Pro Arg Lys Lys Arg Pro Glu Asp Phe Lys Phe Gly Lys Ile Leu
         75                  80                  85 ggg gaa ggc tct ttt tcc acg gtt gtc ctg gct cga gaa ctg gca acc       461
Gly Glu Gly Ser Phe Ser Thr Val Val Leu Ala Arg Glu Leu Ala Thr
 90                  95                 100 tcc aga gaa tat gcg acc agg gcc aac tca ttc gtg gga aca gcg cag       509
Ser Arg Glu Tyr Ala Thr Arg Ala Asn Ser Phe Val Gly Thr Ala Gln
105                 110                 115                 120 tac gtt tct cca gag ctg ctc acg gag aag tcc gcc tgt aag agt tca       557
Tyr Val Ser Pro Glu Leu Leu Thr Glu Lys Ser Ala Cys Lys Ser Ser
                125                 130                 135 gac ctt tgg gct ctt gga tgc ata ata tac cag ctt gtg gca gga ctc       605
Asp Leu Trp Ala Leu Gly Cys Ile Ile Tyr Gln Leu Val Ala Gly Leu
            140                 145                 150 cca cca ttc cga gct gga aac gag tat ctt ata ttt cag aag atc att       653
Pro Pro Phe Arg Ala Gly Asn Glu Tyr Leu Ile Phe Gln Lys Ile Ile
        155                 160                 165 aag ttg gaa tat gac ttt cca gaa aaa ttc ttc cct aag gca aga gac       701
Lys Leu Glu Tyr Asp Phe Pro Glu Lys Phe Phe Pro Lys Ala Arg Asp
    170                 175                 180
```

```
ctc gtg gag aaa ctt ttg gtt tta gat gcc aca aag cgg tta ggc tgt       749
Leu Val Glu Lys Leu Leu Val Leu Asp Ala Thr Lys Arg Leu Gly Cys
185                 190                 195                 200 gag gaa atg gaa gga tac gga cct ctt aaa gca cac ccg ttc ttc gag       797
Glu Glu Met Glu Gly Tyr Gly Pro Leu Lys Ala His Pro Phe Phe Glu
                205                 210                 215 tcc gtc acg tgg gag aac ctg cac cag cag acg cct ccg aag ctc acc       845
Ser Val Thr Trp Glu Asn Leu His Gln Gln Thr Pro Pro Lys Leu Thr
            220                 225                 230 gct tac ctg ccg gct atg tcg gaa gac gac gag gac tgc tat ggc aat       893
Ala Tyr Leu Pro Ala Met Ser Glu Asp Asp Glu Asp Cys Tyr Gly Asn
        235                 240                 245 tat gac aat ctc ctg agc cag ttt ggc tgc atg cag gtg tct tcg tcc       941
Tyr Asp Asn Leu Leu Ser Gln Phe Gly Cys Met Gln Val Ser Ser Ser
    250                 255                 260 tcc tcc tca cac tcc ctg tca gcc tcc gac acg ggc ctg ccc cag agg       989
Ser Ser Ser His Ser Leu Ser Ala Ser Asp Thr Gly Leu Pro Gln Arg
265                 270                 275                 280 tca ggc agc aac ata gag cag tac att cac gat ctg gac tcg aac tcc      1037
Ser Gly Ser Asn Ile Glu Gln Tyr Ile His Asp Leu Asp Ser Asn Ser
                285                 290                 295 ttt gaa ctg gac tta cag ttt tcc gaa gat gag aag agg ttg ttg ttg      1085
Phe Glu Leu Asp Leu Gln Phe Ser Glu Asp Glu Lys Arg Leu Leu Leu
                300                 305                 310 gag aag cag gct ggc gga aac cct tgg cac cag ttt gta gaa aat aat      1133
Glu Lys Gln Ala Gly Gly Asn Pro Trp His Gln Phe Val Glu Asn Asn
            315                 320                 325 tta ata cta aag atg ggc cca gtg gat aag cgg aag ggt tta ttt gca      1181
Leu Ile Leu Lys Met Gly Pro Val Asp Lys Arg Lys Gly Leu Phe Ala
        330                 335                 340 aga cga cga cag ctg ttg ctc aca gaa gga cca cat tta tat tat gtg      1229
Arg Arg Arg Gln Leu Leu Leu Thr Glu Gly Pro His Leu Tyr Tyr Val
345                 350                 355                 360 gat cct gtc aac aaa gtt ctg aaa ggt gaa att cct tgg tca caa gaa      1277
Asp Pro Val Asn Lys Val Leu Lys Gly Glu Ile Pro Trp Ser Gln Glu
                365                 370                 375 ctt cga cca gag gcc aag aat ttt aaa act ttc ttt gtc cac acg cct      1325
Leu Arg Pro Glu Ala Lys Asn Phe Lys Thr Phe Phe Val His Thr Pro
                380                 385                 390 aac agg acg tat tat ctg atg gac ccc agc ggg aac gca cac aag tgg      1373
Asn Arg Thr Tyr Tyr Leu Met Asp Pro Ser Gly Asn Ala His Lys Trp
            395                 400                 405 tgc agg aag atc cag gag gtt tgg agg cag cga tac cag agc cac ccg      1421
Cys Arg Lys Ile Gln Glu Val Trp Arg Gln Arg Tyr Gln Ser His Pro
        410                 415                 420 gac gcc gct gtg cag tga cgtggcctgc ggccgggctg cccttcgctg             1469
Asp Ala Ala Val Gln
425 ccaggacacc tgccccagcg cggcttggcc gccatccggg acgcttccag accacctgcc    1529 agccatcaca aggggaacgc agaggcggaa accttgcagc atttttattt aaaagaaaag    1589 aagaaaaaaa acacccaacc acacaaagaa caaaaccagt aacaaacaca aggaattca     1649 gggtcgcttt gcttgctctc tgtgctccgt ggaggcctcc gtgtgccctc gttgccgtgg    1709 ggacccagct ccatgcacgt caacccagtc ccgcccagac tagtggacag acctggtgtc    1769 accagttttt cctagcatca gtccgaacca tgccccgcc ctgccccaac tgtgtgctgg     1829 tcctgctgtg gccgagggga ccgggtgtgt ttggctcttt atgcccctcc cgctgtggtc    1889 ctggaactct tcaccaggga gggagccctg cgggggccgc agctttgtgg agggagccgc    1949
```

```
cgtgcttctg tcacctgctc cctttcttgc gtctccctgt gatgggccct taggcctggc    2009
tgggcccatt acatatccct gtggtggctc tggtggcagc tttctgtggc ccctgctgtg    2069
ttggcaggca ggtttgcgtg gtgaggagcg ggaggggttg gagtggtgcg ggagcaggct    2129
gccgagtgga gggtgccatc gagggctccg gatcccttat cctacttagc agtgttggtc    2189
tctggggctg gaagccgagc gcatgctggg agcggtactg tcagaagtga gcccagttag    2249
taccccgctg gctcactgca cgagagagtc ctgccccgag ccctaggtgg ggccaggagg    2309
tgccttggag aagccagcca gagcagagag ggctgctgac ttccgtgtgg agcagagagg    2369
cctgagggcc tcctaaaagg tttaaatgtc cacgcctctc cagttgctga agtagggtct    2429
gagagaaccc tggcatcagc agacccaggg tgcttctgtc cctgcagac cacgccaggg     2489 agtgcagaca ccaccgtcac acacgcccct tttgtgtttt ggttcaagtt tctcagagcc    2549
cctcagagct tctacatctg tgcatcagaa atctcacagc cttctcatgc tgccggctca    2609
tctgggccca tagagtgggc tttgccagtt gctgttgcac aggaggcgag aacagcacac    2669 ttcaaccca gcttgctggt cggctttcct ctagagagag ccggttttgg ggccatttcc     2729
ctttgatgct ttggtggcct tgccccgctc tgcagcacag acaggccaga tgcatttgtc    2789 cttttgcctag ctactcccca ggtagagagt gctcctggtg gcctggcagg tctgggccct   2849
tctctccctg cccaggttgt ccctggaggg cagccctcac tccctttggg ggagaggcag    2909
acattgctgc ccacagacct gcctctgact caactgtgtc caccctccct ggtccctacc    2969
cccaagtcac aggtgactca gcagtgaccc tgtgtgccag gccagatcca aactgagagg    3029
gaaggtgtcg ttttttacact gctaatgacg agagtggctc ttttttagcta ggcgagtaca   3089 gacggggcct gggagggggc agagatgttc cccaggccct gcctgtggtt cctgcctggg    3149
ccttggctgc tgctgtgtga gagctgcatg tgagcctgtg accgtgagct ggggtgagct    3209
gggccgcacc taccctgggg ccccagggag caggacgctc cggggcccag cacgttgccc    3269
tgggcctgtg gccggagtcg gagtcctctc tcctcctcct ggcttttgga aaggcttggc    3329
tgtgttgggg agtctctctt agccctttca ggaatttctg ttcaggcttc ctcctcctca    3389 tcagctatt tacccatctc agaacgtcct gtgtctccat gtaggagagt ggctctctca     3449
gatctctcag ggcgtctggt tatagggaaa caagtggagc agggacgtgg ctttaattgg    3509
agcactcggc tgggctgctt ggggagactc ttccgtgcgt tcttcctctg gatagaacca    3569
ccacctcctg ggcgtcactg acaagctcca tcttaacctc caaagccaca gaactagggg    3629
ctcagagcca gagctggcag ccgccagcca aaatgatgcc attgcctgag ctgacagcca    3689
agcccttctg tgggtcacct ttctcctcac ccagcccctt gctcttccct tttgaaaggc    3749
ccgtgtgttt tctttcctta ccctgtgctt gctcatgtct actccggttt tctctaccac    3809
atccttagag ccatcacctg gcacgcaggc gccttacatt ctacggtaga acgtggggta    3869
ctgtgtgtgc acatagacac acttacgtgg aattacagtt gtgggtttat ccaagatgag    3929
gaagatttca cctgctgttt aatagacttg gggccatgtg cctccccaca catgggcaag    3989
gacaggtgga atgtcgggac cacactgtgc ggcttctcgg cacaaagcgg agggaggctg    4049
tggtcgctgc cggcctaggt gtcccaggtg ccccgccttt ctctgggaca cagttggggg    4109
ctggcttctg agggattcct ttctcccctc tttgtgtggc cccagccagg gcggtgggca    4169
gtcctggtgt agagcacaag cctctccacc ctagagaaat gcctctgtac cacggctacc    4229
atgtggaacc ttaacttgca gaaggcttgt taacaattgt tttgagagag atggctggtc    4289
atgccacagc tgctggggac tccgcctact ccagccctct tgggacacac tgtgggattt    4349
```

```
gtggcccttc cccagaggaa ttgtggagac tgtcccatgg aacaaaccct caggcaccag    4409
cacagggctc tgggtgactc agtaaaacta acgtttgtct ctgacaagat cagctgtagg    4469
ctcaccggcc agagaagacc actgtgagca ttttgccgta tatcctgccc tgccatttgt    4529
tcacttttta aactaaaata ggaacatccg acacacaccg tttgcatcgt cttctccctt    4589
gatattttaa gcattttccc atgtcatgag tttctcagaa acatgttttt aacaattgta    4649
ctatttagtc attgtccatt tactataatt tatctgacca tttccctact gtaaatact    4709 taagacggtt tctgattttt ccactattta ataatgctg tgatgaatat ctttaaaatc     4769
ttctgatttc ttactttttt cccccttaga tgcctggaag tggtattttg aggtgaaaga    4829
gtttgttcat tttgaagata tttctgtctc tctctcgacc tgatgtgtag acgctcactt    4889
ccagtagcag aaccaccta gttgtgtctt acagattctg aacaaatcgg tttctgataa     4949
gccatgtgtt ccaagaatg tctgaataag accgctcttt atttaaatgc taagaggatg     5009
tcactactgc aatccatctg tggccgattt tttccaagag ccaatttcct tgttttggtt    5069
gcaagaacct ggctctgcct gcatgtcagc tctctgccct ccctgctgcc gtggctttca    5129
agcgcttggc agaatcttgt acttcgtgtc cacaatggta ctgaatttgc atctgcacag    5189
tcagcagaga taacaagtgt tgaactgacc ttgccacatg cttagtgagt gatttgtaat    5249
taagtttata gactcagaag gtatattagg acatttggaa tcagtagcag agcaaagcct    5309 cttt gaaaaa aaccacgtag ctgattgggt tttacaagag tgcatttgtc tccccttcc    5369 acccgtgggg ccccaccttc aggtcttagt ggttcacaag agcccagcag ccaggctggc    5429
tttttcattg tagggcgtgg ttgtcccagc tggtgtagat ttcaggccgc ccccccaac     5489 tccctgccca cagtgttgca gattgctggg ctggcagcaa gtccagacca cccaaatttg    5549
gttggattct tcatttctcc actgtagttg gggtccattg attgtgcagg gaacgtgca    5609 ggaggttttt ctaggcaccg tgttcagtgc tgcttcactc taccagagat tatggccaaa     5669
ttgcacggaa tttggtttct tgccctctga agcctgaggg ccccccttg cctggctggt     5729 tgacagaccc ggggtggtca ctgctgagac ttcagagatc gcagctgctg tgagaatacg    5789
gtgaaggtac tttgttctgg aagatgttgt catacacttt tccccagtta ttttcaaact    5849
tgacatgagc ctatgttgac tcactgggtg ggggtcccctt cttacgcagc acacgtggca    5909
agtgcctgaa tcgggctgg aggcacttca gagcctctga ggggccacca cttctggccc     5969
aaaattgcag ggttgtagat gaggctgcct gtggagaact ggtgtgagga ggaagctgtt    6029
tccaacaaag agcactttca tctgttgaga tggctgtggt gagcaactga acgagcctac    6089
gtgtgtacct gaattttccc cgtaactcat ttcttccata tgaagaaaca ccaaactatg    6149
tacagagaac ttttta caaa aggcagacct tttttaagct gtgtaaccca catagcctaa    6209
ccacctggca gaatgactac gaataggggt cattgtgctg gtaaaagcct ctattacgac    6269
tgtaagtaag ttggatgttg gcaaaattaa attgttacag tatttagagc tgctgtagct    6329
gttccttcac aacataaaat aggataaatg actagtacgt ctttcaggtg ggtggcaagc    6389
agaacatgcg taatattctc tacctggtct gtagctgtaa ctgtgatgta cagacaaagc    6449
aaaaattaaa agaacttatg aaaacaaatg caatgatact aggatataca cttttgtatt    6509
tttattctta tataaggtta tttgctggct attgttggcc tctagttcag tctgtgttat    6569
ttaaattcta atatatgaat tatttgaatt gaattcatgt tcggggccac gttgttgtat    6629
gtattgatgt acagccttga atgtgaataa ttattgtaaa ctatatttta caactttttt    6689
tctggcttta ttatataaat tttctattgg gtcagtgatt taatcatata atttaatgaa    6749
```

-continued

```
tctgtttatc cttttttttt ttccaaatac ttgtgcttta ggtgtagtta ccagatgatg    6809
aattttcctc gtatggtcag tagtcttgta ataaaaagca tgtagagtgt aga           6862
```

<210> SEQ ID NO 5
<211> LENGTH: 429
<212> TYPE: PRT
<213> ORGANISM: Homo sapiens

<400> SEQUENCE: 5

Met Ala Arg Thr Thr Ser Gln Leu Tyr Asp Ala Val Pro Ile Gln Ser
1               5                   10                  15

Ser Val Val Leu Cys Ser Cys Pro Ser Pro Ser Met Val Arg Thr Gln
            20                  25                  30

Thr Glu Ser Ser Thr Pro Pro Gly Ile Pro Gly Gly Ser Arg Gln Gly
        35                  40                  45

Pro Ala Met Asp Gly Thr Ala Ala Glu Pro Arg Pro Gly Ala Gly Ser
    50                  55                  60

Leu Gln His Ala Gln Pro Pro Gln Pro Arg Lys Lys Arg Pro Glu
65                  70                  75                  80

Asp Phe Lys Phe Gly Lys Ile Leu Gly Glu Gly Ser Phe Ser Thr Val
                85                  90                  95

Val Leu Ala Arg Glu Leu Ala Thr Ser Arg Glu Tyr Ala Thr Arg Ala
            100                 105                 110

Asn Ser Phe Val Gly Thr Ala Gln Tyr Val Ser Pro Glu Leu Leu Thr
        115                 120                 125

Glu Lys Ser Ala Cys Lys Ser Ser Asp Leu Trp Ala Leu Gly Cys Ile
130                 135                 140

Ile Tyr Gln Leu Val Ala Gly Leu Pro Pro Phe Arg Ala Gly Asn Glu
145                 150                 155                 160

Tyr Leu Ile Phe Gln Lys Ile Ile Lys Leu Glu Tyr Asp Phe Pro Glu
                165                 170                 175

Lys Phe Phe Pro Lys Ala Arg Asp Leu Val Glu Lys Leu Leu Val Leu
            180                 185                 190

Asp Ala Thr Lys Arg Leu Gly Cys Glu Glu Met Glu Gly Tyr Gly Pro
        195                 200                 205

Leu Lys Ala His Pro Phe Phe Glu Ser Val Thr Trp Glu Asn Leu His
    210                 215                 220

Gln Gln Thr Pro Pro Lys Leu Thr Ala Tyr Leu Pro Ala Met Ser Glu
225                 230                 235                 240

Asp Asp Glu Asp Cys Tyr Gly Asn Tyr Asp Asn Leu Leu Ser Gln Phe
                245                 250                 255

Gly Cys Met Gln Val Ser Ser Ser Ser His Ser Leu Ser Ala
            260                 265                 270

Ser Asp Thr Gly Leu Pro Gln Arg Ser Gly Ser Asn Ile Glu Gln Tyr
        275                 280                 285

Ile His Asp Leu Asp Ser Asn Ser Phe Glu Leu Asp Leu Gln Phe Ser
    290                 295                 300

Glu Asp Glu Lys Arg Leu Leu Leu Glu Lys Gln Ala Gly Gly Asn Pro
305                 310                 315                 320

Trp His Gln Phe Val Glu Asn Asn Leu Ile Leu Lys Met Gly Pro Val
                325                 330                 335

Asp Lys Arg Lys Gly Leu Phe Ala Arg Arg Arg Gln Leu Leu Leu Thr
            340                 345                 350

-continued

```
Glu Gly Pro His Leu Tyr Tyr Val Asp Pro Val Asn Lys Val Leu Lys
            355                 360                 365

Gly Glu Ile Pro Trp Ser Gln Glu Leu Arg Pro Glu Ala Lys Asn Phe
370                 375                 380

Lys Thr Phe Phe Val His Thr Pro Asn Arg Thr Tyr Tyr Leu Met Asp
385                 390                 395                 400

Pro Ser Gly Asn Ala His Lys Trp Cys Arg Lys Ile Gln Glu Val Trp
                405                 410                 415

Arg Gln Arg Tyr Gln Ser His Pro Asp Ala Ala Val Gln
            420                 425

<210> SEQ ID NO 6
<211> LENGTH: 7032
<212> TYPE: DNA
<213> ORGANISM: Homo sapiens
<220> FEATURE:
<221> NAME/KEY: CDS
<222> LOCATION: (150)..(1514)

<400> SEQUENCE: 6
gcggcgccgg gggcgggggg cggcgggcga cggggcgggc gcaggatgag ggcggccatt    60 gctgggctc cgcttcgggg aggaggacgc tgaggaggcg ccgagccgcg cagcgctgcg   120
ggggaggcgc ccgcgccgac gcggggccc atg gcc agg acc acc agc cag ctg   173
                                Met Ala Arg Thr Thr Ser Gln Leu
                                  1               5 tat gac gcc gtg ccc atc cag tcc agc gtg gtg tta tgt tcc tgc cca   221
Tyr Asp Ala Val Pro Ile Gln Ser Ser Val Val Leu Cys Ser Cys Pro
 10                  15                  20 tcc cca tca atg gtg agg acc cag act gag tcc agc acg ccc cct ggc   269
Ser Pro Ser Met Val Arg Thr Gln Thr Glu Ser Ser Thr Pro Pro Gly
 25                  30                  35                  40 att cct ggt ggc agc agg cag ggc ccc gcc atg gac ggc act gca gcc   317
Ile Pro Gly Gly Ser Arg Gln Gly Pro Ala Met Asp Gly Thr Ala Ala
                 45                  50                  55 gag cct cgg ccc ggc gcc ggc tcc ctg cag cat gcc cag cct ccg ccg   365
Glu Pro Arg Pro Gly Ala Gly Ser Leu Gln His Ala Gln Pro Pro Pro
             60                  65                  70 cag cct cgg aag aag cgg cct gag gac ttc aag ttt ggg aaa atc ctt   413
Gln Pro Arg Lys Lys Arg Pro Glu Asp Phe Lys Phe Gly Lys Ile Leu
         75                  80                  85 ggg gaa ggc tct ttt tcc acg gtt gtc ctg gct cga gaa ctg gca acc   461
Gly Glu Gly Ser Phe Ser Thr Val Val Leu Ala Arg Glu Leu Ala Thr
 90                  95                 100 tcc aga gaa tat gcg att aaa att ctg gag aag cga cat atc ata aaa   509
Ser Arg Glu Tyr Ala Ile Lys Ile Leu Glu Lys Arg His Ile Ile Lys
105                 110                 115                 120 gag aac aag gtc ccc tat gta acc aga gag cgg gat gtc atg tcg cgc   557
Glu Asn Lys Val Pro Tyr Val Thr Arg Glu Arg Asp Val Met Ser Arg
                125                 130                 135 ctg gat cac ccc ttc ttt gtt aag ctt tac ttc aca ttt cag gac gac   605
Leu Asp His Pro Phe Phe Val Lys Leu Tyr Phe Thr Phe Gln Asp Asp
            140                 145                 150 gag aag ctg tat ttc ggc ctt agt tat gcc aaa aat gga gaa cta ctt   653
Glu Lys Leu Tyr Phe Gly Leu Ser Tyr Ala Lys Asn Gly Glu Leu Leu
        155                 160                 165 aaa tat att cgc aaa atc ggt tca ttc gat gag acc tgt acc cga ttt   701
Lys Tyr Ile Arg Lys Ile Gly Ser Phe Asp Glu Thr Cys Thr Arg Phe
    170                 175                 180
```

-continued

| | |
|---|---|
| tac acg gct gag att gtg tct gct tta gag tac ttg cac ggc aag ggc<br>Tyr Thr Ala Glu Ile Val Ser Ala Leu Glu Tyr Leu His Gly Lys Gly<br>185                         190                       195                     200 | 749 |
| atc att cac agg gac ctt aaa ccg gaa aac att ttg tta aat gaa gat<br>Ile Ile His Arg Asp Leu Lys Pro Glu Asn Ile Leu Leu Asn Glu Asp<br>                  205                       210                     215 | 797 |
| atg cac atc cag atc aca gat ttt gga aca gca aaa gtc tta tcc cca<br>Met His Ile Gln Ile Thr Asp Phe Gly Thr Ala Lys Val Leu Ser Pro<br>        220                     225                     230 | 845 |
| gag agc aaa caa gcc agg gcc aac tca ttc gtg gga aca gcg cag tac<br>Glu Ser Lys Gln Ala Arg Ala Asn Ser Phe Val Gly Thr Ala Gln Tyr<br>235                       240                       245 | 893 |
| gtt tct cca gag ctg ctc acg gag aag tcc gcc tgt aag agt tca gac<br>Val Ser Pro Glu Leu Leu Thr Glu Lys Ser Ala Cys Lys Ser Ser Asp<br>     250                     255                     260 | 941 |
| ctt tgg gct ctt gga tgc ata ata tac cag ctt gtg gca gga ctc cca<br>Leu Trp Ala Leu Gly Cys Ile Ile Tyr Gln Leu Val Ala Gly Leu Pro<br>265                       270                     275                     280 | 989 |
| cca ttc cga gct gga aac gag tat ctt ata ttt cag aag atc att aag<br>Pro Phe Arg Ala Gly Asn Glu Tyr Leu Ile Phe Gln Lys Ile Ile Lys<br>                  285                     290                     295 | 1037 |
| ttg gaa tat gac ttt cca gaa aaa ttc ttc cct aag gca aga gac ctc<br>Leu Glu Tyr Asp Phe Pro Glu Lys Phe Phe Pro Lys Ala Arg Asp Leu<br>        300                     305                     310 | 1085 |
| gtg gag aaa ctt ttg gtt tta gat gcc aca aag cgg tta ggc tgt gag<br>Val Glu Lys Leu Leu Val Leu Asp Ala Thr Lys Arg Leu Gly Cys Glu<br>315                       320                       325 | 1133 |
| gaa atg gaa gga tac gga cct ctt aaa gca cac ccg ttc ttc gag tcc<br>Glu Met Glu Gly Tyr Gly Pro Leu Lys Ala His Pro Phe Phe Glu Ser<br>     330                     335                     340 | 1181 |
| gtc acg tgg gag aac ctg cac cag cag acg cct ccg aag ctc acc gct<br>Val Thr Trp Glu Asn Leu His Gln Gln Thr Pro Pro Lys Leu Thr Ala<br>345                       350                       355                     360 | 1229 |
| tac ctg ccg gct atg tcg gaa gac gac gag gac tgc tat ggc aat tat<br>Tyr Leu Pro Ala Met Ser Glu Asp Asp Glu Asp Cys Tyr Gly Asn Tyr<br>                  365                     370                     375 | 1277 |
| gac aat ctc ctg agc cag ttt ggc tgc atg cag gtg tct tcg tcc tcc<br>Asp Asn Leu Leu Ser Gln Phe Gly Cys Met Gln Val Ser Ser Ser Ser<br>        380                     385                     390 | 1325 |
| tcc tca cac tcc ctg tca gcc tcc gac acg ggc ctg ccc cag agg tca<br>Ser Ser His Ser Leu Ser Ala Ser Asp Thr Gly Leu Pro Gln Arg Ser<br>395                       400                       405 | 1373 |
| ggc agc aac ata gag cag tac att cac gat ctg gac tcg aac tcc ttt<br>Gly Ser Asn Ile Glu Gln Tyr Ile His Asp Leu Asp Ser Asn Ser Phe<br>     410                     415                     420 | 1421 |
| gaa ctg gac tta cag ttt tcc gaa gat gag aag agg ttg ttg ttg gag<br>Glu Leu Asp Leu Gln Phe Ser Glu Asp Glu Lys Arg Leu Leu Leu Glu<br>425                       430                       435                     440 | 1469 |
| aag cag gct ggc gga aac cct tgc cta aca gga cgt att atc tga<br>Lys Gln Ala Gly Gly Asn Pro Cys Leu Thr Gly Arg Ile Ile<br>                  445                     450 | 1514 |
| tggaccccag cgggaacgca cacaagtggt gcaggaagat ccaggaggtt tggaggcagc | 1574 |
| gataccagag ccacccggac gccgctgtgc agtgacgtgg cctgcggccg ggctgccctt | 1634 |
| cgctgccagg acacctgccc cagcgcggct tggccgccat ccgggacgct tccagaccac | 1694 |
| ctgccagcca tcacaagggg aacgcagagg cggaaacctt gcagcatttt tatttaaaag | 1754 |
| aaaagaagaa aaaaaacacc caaccacaca aagaacaaaa ccagtaacaa acacaaagga | 1814 |
| attcagggtc gctttgcttg ctctctgtgc tccgtggagg cctccgtgtg ccctcgttgc | 1874 |

```
cgtggggacc cagctccatg cacgtcaacc cagtcccgcc cagactagtg gacagacctg    1934
gtgtcaccag ttttttcctag catcagtccg aaccatgcgc ccgccctgcc ccaactgtgt    1994
gctggtcctg ctgtggccga ggggaccggg tgtgtttggc tctttatgcc cctcccgctg    2054
tggtcctgga actcttcacc agggaggag ccctgcgggg gccgcagctt tgtggaggga     2114
gccgccgtgc ttctgtcacc tgctccctt cttgcgtctc cctgtgatgg gcccttaggc    2174
ctggctgggc ccattacata tccctgtggt ggctctggtg gcagctttct gtggccctg    2234
ctgtgttggc aggcaggttt gcgtggtgag gagcgggagg ggttggagtg gtgcgggagc    2294
aggctgccga gtggagggtg ccatcgaggg ctccggatcc cttatcctac ttagcagtgt    2354
tggtctctgg ggctggaagc cgagcgcatg ctgggagcgg tactgtcaga agtgagccca    2414
gttagtaccc cgctggctca ctgcacgaga gagtcctgcc ccgagcccta ggtggggcca    2474
ggaggtgcct tggagaagcc agccagagca gagagggctg ctgacttccg tgtggagcag    2534
agaggcctga gggcctccta aaaggtttaa atgtccacgc ctctccagtt gctgaagtag    2594
ggtctgagag aaccctggca tcagcagacc cagggtgctt ctgtctcctg cagaccacgc    2654
cagggagtgc agacaccacc gtcacacacg cccctttttgt gttttggttc aagtttctca    2714
gagcccctca gagcttctac atctgtgcat cagaaatctc acagccttct catgctgccg    2774
gctcatctgg gcccatagag tgggcttttgc cagttgctgt tgcacaggag gcgagaacag    2834
cacacttcaa ccccagcttg ctggtcggct ttcctctaga gagagccggt tttgggggcca    2894
tttcccttg atgctttggt ggccttgccc cgctctgcag cacagacagg ccagatgcat    2954
ttgtcctttg cctagctact ccccaggtag agagtgctcc tggtggcctg gcaggtctgg    3014
gcccttctct ccctgcccag gttgtccctg gagggcagcc ctcactccct ttgggggaga    3074
ggcagacatt gctgcccaca gacctgcctc tgactcaact gtgtccaccc tccctggtcc    3134
ctaccccaa gtcacaggtg actcagcagt gaccctgtgt gccaggccag atccaaactg    3194
agagggaagg tgtcgttttt acactgctaa tgacgagagt ggctcttttt agctaggcga    3254
gtacagacgg ggcctgggag ggggcagaga tgttccccag gccctgcctg tggttcctgc    3314
ctgggccttg gctgctgctg tgtgagagct gcatgtgagc ctgtgaccgt gagctggggt    3374
gagctgggcc gcacctaccc tggggcccca gggagcagga cgctccgggg cccagcacgt    3434
tgccctgggc ctgtggccgg agtcggagtc ctctctcctc ctcctggctt ttggaaaggc    3494
ttggctgtgt tggggagtct ctcttagccc tttcaggaat ttctgttcag gcttcctcct    3554
cctcatcagc tattttaccc atctcagaac gtcctgtgtc tccatgtagg agagtggctc    3614
tctcagatct ctcagggcgt ctggttatag ggaaacaagt ggagcaggga cgtggcttta    3674
attggagcac tcggctgggc tgcttgggga gactcttccg tgcgttcttc ctctggatag    3734
aaccaccacc tcctgggcgt cactgacaag ctccatctta acctccaaag ccacagaact    3794
aggggctcag agccagagct ggcagccgcc agccaaaatg atgccattgc ctgagctgac    3854
agccaagccc ttctgtgggt cacctttctc ctcacccagc cccttgctct tccctttga    3914
aaggcccgtg tgttttcttt ccttaccctg tgcttgctca tgtctactcc ggttttctct    3974
accacatcct tagagccatc acctggcacg caggcgcctt acattctacg gtagaacgtg    4034
gggtactgtg tgtgcacata gacacactta cgtggaatta cagttgtggg tttatccaag    4094
atgaggaaga tttcacctgc tgtttaatag acttggggcc atgtgcctcc ccacacatgg    4154
gcaaggacag gtggaatgtc gggaccacac tgtgcggctt ctcggcacaa agcggaggga    4214
ggctgtggtc gctgccggcc taggtgtccc aggtgccccg cctttctctg ggacacagtt    4274
```

```
gggggctggc ttctgaggga ttcctttctc ccctctttgt gtggcccag ccagggcggt      4334 gggcagtcct ggtgtagagc acaagcctct ccaccctaga gaaatgcctc tgtaccacgg      4394
ctaccatgtg gaaccttaac ttgcagaagg cttgttaaca attgttttga gagagatggc      4454
tggtcatgcc acagctgctg gggactccgc ctactccagc cctcttggga cacactgtgg      4514
gatttgtggc ccttccccag aggaattgtg gagactgtcc catggaacaa accctcaggc      4574
accagcacag ggctctgggt gactcagtaa aactaacgtt tgtctctgac aagatcagct      4634
gtaggctcac cggccagaga agaccactgt gagcattttg ccgtatatcc tgccctgcca      4694
tttgttcact ttttaaacta aaataggaac atccgacaca caccgtttgc atcgtcttct      4754
cccttgatat tttaagcatt tcccatgtc atgagtttct cagaaacatg ttttttaacaa      4814 ttgtactatt tagtcattgt ccatttacta taatttatct gaccatttcc ctactgtaaa      4874
atacttaaga cggtttctga ttttttccact atttaaataa tgctgtgatg aatatcttta      4934
aaatcttctg atttcttact tttttccccc ttagatgcct ggaagtggta ttttgaggtg      4994
aaagagtttg ttcattttga agatatttct gtctctctct cgacctgatg tgtagacgct      5054
cacttccagt agcagaacca ccttagttgt gtcttacaga ttctgaacaa atcggtttct      5114
gataagccat gtgttccaaa gaatgtctga ataagaccgc tctttattta aatgctaaga      5174
ggatgtcact actgcaatcc atctgtggcc gattttttcc aagagccaat ttccttgttt      5234
tggttgcaag aacctggctc tgcctgcatg tcagctctct gccctccctg ctgccgtggc      5294
tttcaagcgc ttggcagaat cttgtacttc gtgtccacaa tggtactgaa tttgcatctg      5354
cacagtcagc agagataaca agtgttgaac tgaccttgcc acatgcttag tgagtgattt      5414
gtaattaagt ttatagactc agaaggtata ttaggacatt tggaatcagt agcagagcaa      5474
agcctctttg aaaaaaacca cgtagctgat tgggttttac aagagtgcat ttgtctcccc      5534
cttccacccg tggggcccca ccttcaggtc ttagtggttc acaagagccc agcagccagg      5594
ctggcttttt cattgtaggg cgtggttgtc ccagctggtg tagatttcag gccgcccccc      5654
ccaactccct gcccacagtg ttgcagattg cctggctggc agcaagtcca gaccacccaa      5714
atttggttgg attcttcatt tctccactgt agttggggtc cattgattgt gcaggggaac      5774
gtgcaggagg ttttctagg caccgtgttc agtgctgctt cactctacca gagattatgg      5834
ccaaattgca cggaatttgg tttcttgccc tctgaagcct gagggccccc ccttgcctgg      5894
ctggttgaca gacccggggt ggtcactgct gagacttcag agatcgcagc tgctgtgaga      5954
atacggtgaa ggtactttgt tctggaagat gttgtcatac acttttcccc agttattttc      6014
aaacttgaca tgagcctatg ttgactcact gggtgggggt cccttcttac gcagcacacg      6074
tggcaagtgc ctgaatcggg gctggaggca cttcagagcc tctgagggc caccacttct      6134 ggcccaaaat tgcagggttg tagatgaggc tgcctgtgga gaactggtgt gaggaggaag      6194
ctgtttccaa caaagagcac tttcatctgt tgagatggct gtggtgagca actgaacgag      6254
cctacgtgtg tacctgaatt ttccccgtaa ctcatttctt ccatatgaag aaacaccaaa      6314
ctatgtacag agaacttttt acaaaaggca gaccttttt aagctgtgta acccacatag      6374
cctaaccacc tggcagaatg actacgaata ggggtcattg tgctggtaaa agcctctatt      6434
acgactgtaa gtaagttgga tgttggcaaa attaaattgt tacagtattt agagctgctg      6494
tagctgttcc ttcacaacat aaaataggat aaatgactag tacgtctttc aggtgggtgg      6554
caagcagaac atgcgtaata ttctctacct ggtctgtagc tgtaactgtg atgtacagac      6614
aaagcaaaaa ttaaaagaac ttatgaaaac aaatgcaatg atactaggat atacactttt      6674
```

-continued

```
gtatttttat tcttatataa ggttatttgc tggctattgt tggcctctag ttcagtctgt    6734
gttatttaaa ttctaatata tgaattattt gaattgaatt catgttcggg gccacgttgt    6794
tgtatgtatt gatgtacagc cttgaatgtg aataattatt gtaaactata ttttacaact    6854
ttttttctgg ctttattata taaattttct attgggtcag tgatttaatc atataattta    6914
atgaatctgt ttatcctttt ttttttttcca aatacttgtg ctttaggtgt agttaccaga    6974
tgatgaattt tcctcgtatg gtcagtagtc ttgtaataaa aagcatgtag agtgtaga      7032
```

<210> SEQ ID NO 7
<211> LENGTH: 454
<212> TYPE: PRT
<213> ORGANISM: Homo sapiens

<400> SEQUENCE: 7

```
Met Ala Arg Thr Thr Ser Gln Leu Tyr Asp Ala Val Pro Ile Gln Ser
1               5                   10                  15

Ser Val Val Leu Cys Ser Cys Pro Ser Pro Ser Met Val Arg Thr Gln
                20                  25                  30

Thr Glu Ser Ser Thr Pro Pro Gly Ile Pro Gly Gly Ser Arg Gln Gly
            35                  40                  45

Pro Ala Met Asp Gly Thr Ala Ala Glu Pro Arg Pro Gly Ala Gly Ser
        50                  55                  60

Leu Gln His Ala Gln Pro Pro Pro Gln Pro Arg Lys Lys Arg Pro Glu
65                  70                  75                  80

Asp Phe Lys Phe Gly Lys Ile Leu Gly Glu Gly Ser Phe Ser Thr Val
                85                  90                  95

Val Leu Ala Arg Glu Leu Ala Thr Ser Arg Glu Tyr Ala Ile Lys Ile
                100                 105                 110

Leu Glu Lys Arg His Ile Ile Lys Glu Asn Lys Val Pro Tyr Val Thr
            115                 120                 125

Arg Glu Arg Asp Val Met Ser Arg Leu Asp His Pro Phe Phe Val Lys
        130                 135                 140

Leu Tyr Phe Thr Phe Gln Asp Asp Glu Lys Leu Tyr Phe Gly Leu Ser
145                 150                 155                 160

Tyr Ala Lys Asn Gly Glu Leu Leu Lys Tyr Ile Arg Lys Ile Gly Ser
                165                 170                 175

Phe Asp Glu Thr Cys Thr Arg Phe Tyr Thr Ala Glu Ile Val Ser Ala
            180                 185                 190

Leu Glu Tyr Leu His Gly Lys Gly Ile Ile His Arg Asp Leu Lys Pro
        195                 200                 205

Glu Asn Ile Leu Leu Asn Glu Asp Met His Ile Gln Ile Thr Asp Phe
    210                 215                 220

Gly Thr Ala Lys Val Leu Ser Pro Glu Ser Lys Gln Ala Arg Ala Asn
225                 230                 235                 240

Ser Phe Val Gly Thr Ala Gln Tyr Val Ser Pro Glu Leu Leu Thr Glu
                245                 250                 255

Lys Ser Ala Cys Lys Ser Ser Asp Leu Trp Ala Leu Gly Cys Ile Ile
            260                 265                 270

Tyr Gln Leu Val Ala Gly Leu Pro Pro Phe Arg Ala Gly Asn Glu Tyr
        275                 280                 285

Leu Ile Phe Gln Lys Ile Ile Lys Leu Glu Tyr Asp Phe Pro Glu Lys
    290                 295                 300

Phe Phe Pro Lys Ala Arg Asp Leu Val Glu Lys Leu Leu Val Leu Asp
305                 310                 315                 320
```

```
Ala Thr Lys Arg Leu Gly Cys Glu Glu Met Glu Gly Tyr Gly Pro Leu
            325                 330                 335

Lys Ala His Pro Phe Phe Glu Ser Val Thr Trp Glu Asn Leu His Gln
        340                 345                 350

Gln Thr Pro Pro Lys Leu Thr Ala Tyr Leu Pro Ala Met Ser Glu Asp
            355                 360                 365

Asp Glu Asp Cys Tyr Gly Asn Tyr Asp Asn Leu Leu Ser Gln Phe Gly
        370                 375                 380

Cys Met Gln Val Ser Ser Ser Ser Ser His Ser Leu Ser Ala Ser
385                 390                 395                 400

Asp Thr Gly Leu Pro Gln Arg Ser Gly Ser Asn Ile Glu Gln Tyr Ile
                405                 410                 415

His Asp Leu Asp Ser Asn Ser Phe Glu Leu Asp Leu Gln Phe Ser Glu
            420                 425                 430

Asp Glu Lys Arg Leu Leu Leu Glu Lys Gln Ala Gly Gly Asn Pro Cys
        435                 440                 445

Leu Thr Gly Arg Ile Ile
    450

<210> SEQ ID NO 8
<211> LENGTH: 7337
<212> TYPE: DNA
<213> ORGANISM: Homo sapiens
<220> FEATURE:
<221> NAME/KEY: CDS
<222> LOCATION: (327)..(1916)

<400> SEQUENCE: 8
attgctgggg ctccgcttcg gggaggagga cgctgaggag gcgccgagcc gcgcagcgct        60 gcggggagg cgcccgcgcc gacgcgggc ccatggccag gaccaccagc cagctgattc       120
ttgatgacag tggtcgggaa aactcgcctt tcacggcccg gccaaggggc atttgggtgc       180
ttttgctgcc cgtggctgtg ctcagcgttg tgggaagccc ctgggaggcc gaatgtgcag       240
gatcaccgag gggaaagtga gcttgacagt atgacgccgt gcccatccag tccagcgtgg       300
tgttatgttc ctgcccatcc ccatca atg gtg agg acc cag act gag tcc agc        353
                              Met Val Arg Thr Gln Thr Glu Ser Ser
                                1               5 acg ccc cct ggc att cct ggt ggc agc agg cag ggc ccc gcc atg gac        401
Thr Pro Pro Gly Ile Pro Gly Gly Ser Arg Gln Gly Pro Ala Met Asp
 10              15                  20                  25 ggc act gca gcc gag cct cgg ccc ggc gcc ggc tcc ctg cag cat gcc        449
Gly Thr Ala Ala Glu Pro Arg Pro Gly Ala Gly Ser Leu Gln His Ala
             30                  35                  40 cag cct ccg ccg cag cct cgg aag aag cgg cct gag gac ttc aag ttt        497
Gln Pro Pro Pro Gln Pro Arg Lys Lys Arg Pro Glu Asp Phe Lys Phe
         45                  50                  55 ggg aaa atc ctt ggg gaa ggc tct ttt tcc acg gtt gtc ctg gct cga        545
Gly Lys Ile Leu Gly Glu Gly Ser Phe Ser Thr Val Val Leu Ala Arg
     60                  65                  70 gaa ctg gca acc tcc aga gaa tat gcg att aaa att ctg gag aag cga        593
Glu Leu Ala Thr Ser Arg Glu Tyr Ala Ile Lys Ile Leu Glu Lys Arg
 75                  80                  85 cat atc ata aaa gag aac aag gtc ccc tat gta acc aga gag cgg gat        641
His Ile Ile Lys Glu Asn Lys Val Pro Tyr Val Thr Arg Glu Arg Asp
 90                  95                 100                 105 gtc atg tcg cgc ctg gat cac ccc ttt ttt gtt aag ctt tac ttc aca        689
Val Met Ser Arg Leu Asp His Pro Phe Phe Val Lys Leu Tyr Phe Thr
             110                 115                 120
```

| | |
|---|---|
| ttt cag gac gac gag aag ctg tat ttc ggc ctt agt tat gcc aaa aat<br>Phe Gln Asp Asp Glu Lys Leu Tyr Phe Gly Leu Ser Tyr Ala Lys Asn<br>125                              130                         135 | 737 |
| gga gaa cta ctt aaa tat att cgc aaa atc ggt tca ttc gat gag acc<br>Gly Glu Leu Leu Lys Tyr Ile Arg Lys Ile Gly Ser Phe Asp Glu Thr<br>140                            145                       150 | 785 |
| tgt acc cga ttt tac acg gct gag att gtg tct gct tta gag tac ttg<br>Cys Thr Arg Phe Tyr Thr Ala Glu Ile Val Ser Ala Leu Glu Tyr Leu<br>155                              160                       165 | 833 |
| cac ggc aag ggc atc att cac agg gac ctt aaa ccg gaa aac att ttg<br>His Gly Lys Gly Ile Ile His Arg Asp Leu Lys Pro Glu Asn Ile Leu<br>170                            175                       180                  185 | 881 |
| tta aat gaa gat atg cac atc cag atc aca gat ttt gga aca gca aaa<br>Leu Asn Glu Asp Met His Ile Gln Ile Thr Asp Phe Gly Thr Ala Lys<br>190                            195                       200 | 929 |
| gtc tta tcc cca gag agc aaa caa gcc agg gcc aac tca ttc gtg gga<br>Val Leu Ser Pro Glu Ser Lys Gln Ala Arg Ala Asn Ser Phe Val Gly<br>205                             210                       215 | 977 |
| aca gcg cag tac gtt tct cca gag ctg ctc acg gag aag tcc gcc tgt<br>Thr Ala Gln Tyr Val Ser Pro Glu Leu Leu Thr Glu Lys Ser Ala Cys<br>220                            225                       230 | 1025 |
| aag agt tca gac ctt tgg gct ctt gga tgc ata ata tac cag ctt gtg<br>Lys Ser Ser Asp Leu Trp Ala Leu Gly Cys Ile Ile Tyr Gln Leu Val<br>235                            240                       245 | 1073 |
| gca gga ctc cca cca ttc cga gct gga aac gag tat ctt ata ttt cag<br>Ala Gly Leu Pro Pro Phe Arg Ala Gly Asn Glu Tyr Leu Ile Phe Gln<br>250                            255                       260                  265 | 1121 |
| aag atc att aag ttg gaa tat gac ttt cca gaa aaa ttc ttc cct aag<br>Lys Ile Ile Lys Leu Glu Tyr Asp Phe Pro Glu Lys Phe Phe Pro Lys<br>                            270                       275                       280 | 1169 |
| gca aga gac ctc gtg gag aaa ctt ttg gtt tta gat gcc aca aag cgg<br>Ala Arg Asp Leu Val Glu Lys Leu Leu Val Leu Asp Ala Thr Lys Arg<br>285                            290                       295 | 1217 |
| tta ggc tgt gag gaa atg gaa gga tac gga cct ctt aaa gca cac ccg<br>Leu Gly Cys Glu Glu Met Glu Gly Tyr Gly Pro Leu Lys Ala His Pro<br>300                            305                       310 | 1265 |
| ttc ttc gag tcc gtc acg tgg gag aac ctg cac cag cag acg cct ccg<br>Phe Phe Glu Ser Val Thr Trp Glu Asn Leu His Gln Gln Thr Pro Pro<br>315                            320                       325 | 1313 |
| aag ctc acc gct tac ctg ccg gct atg tcg gaa gac gac gag gac tgc<br>Lys Leu Thr Ala Tyr Leu Pro Ala Met Ser Glu Asp Asp Glu Asp Cys<br>330                            335                       340                  345 | 1361 |
| tat ggc aat tat gac aat ctc ctg agc cag ttt ggc tgc atg cag gtg<br>Tyr Gly Asn Tyr Asp Asn Leu Leu Ser Gln Phe Gly Cys Met Gln Val<br>                            350                       355                       360 | 1409 |
| tct tcg tcc tcc tcc tca cac tcc ctg tca gcc tcc gac acg ggc ctg<br>Ser Ser Ser Ser Ser Ser His Ser Leu Ser Ala Ser Asp Thr Gly Leu<br>                            365                       370                       375 | 1457 |
| ccc cag agg tca ggc agc aac ata gag cag tac att cac gat ctg gac<br>Pro Gln Arg Ser Gly Ser Asn Ile Glu Gln Tyr Ile His Asp Leu Asp<br>380                            385                       390 | 1505 |
| tcg aac tcc ttt gaa ctg gac tta cag ttt tcc gaa gat gag aag agg<br>Ser Asn Ser Phe Glu Leu Asp Leu Gln Phe Ser Glu Asp Glu Lys Arg<br>395                            400                       405 | 1553 |
| ttg ttg ttg gag aag cag gct ggc gga aac cct tgg cac cag ttt gta<br>Leu Leu Leu Glu Lys Gln Ala Gly Gly Asn Pro Trp His Gln Phe Val<br>410                            415                       420                  425 | 1601 |
| gaa aat aat tta ata cta aag atg ggc cca gtg gat aag cgg aag ggt<br>Glu Asn Asn Leu Ile Leu Lys Met Gly Pro Val Asp Lys Arg Lys Gly<br>                            430                       435                       440 | 1649 |

```
tta ttt gca aga cga cga cag ctg ttg ctc aca gaa gga cca cat tta    1697
Leu Phe Ala Arg Arg Arg Gln Leu Leu Leu Thr Glu Gly Pro His Leu
            445                 450                 455 tat tat gtg gat cct gtc aac aaa gtt ctg aaa ggt gaa att cct tgg    1745
Tyr Tyr Val Asp Pro Val Asn Lys Val Leu Lys Gly Glu Ile Pro Trp
        460                 465                 470 tca caa gaa ctt cga cca gag gcc aag aat ttt aaa act ttc ttt gtc    1793
Ser Gln Glu Leu Arg Pro Glu Ala Lys Asn Phe Lys Thr Phe Phe Val
    475                 480                 485 cac acg cct aac agg acg tat tat ctg atg gac ccc agc ggg aac gca    1841
His Thr Pro Asn Arg Thr Tyr Tyr Leu Met Asp Pro Ser Gly Asn Ala
490                 495                 500                 505 cac aag tgg tgc agg aag atc cag gag gtt tgg agg cag cga tac cag    1889
His Lys Trp Cys Arg Lys Ile Gln Glu Val Trp Arg Gln Arg Tyr Gln
                510                 515                 520 agc cac ccg gac gcc gct gtg cag tga cgtggcctgc ggccgggctg          1936
Ser His Pro Asp Ala Ala Val Gln
                525 ccct tcgctg ccaggacacc tgcccagcg cggcttggcc gccatccggg acgcttccag   1996
accacctgcc agccatcaca aggggaacgc agaggcggaa accttgcagc attttattt   2056 aaagaaaag aagaaaaaaa acacccaacc acacaagaa caaaaccagt aacaaacaca    2116
aaggaattca gggtcgcttt gcttgctctc tgtgctccgt ggaggcctcc gtgtgccctc   2176
gttgccgtgg ggaccagct ccatgcacgt caacccagtc ccgcccagac tagtggacag   2236
acctggtgtc accagttttt cctagcatca gtccgaacca tgcgcccgcc ctgccccaac   2296
tgtgtgctgg tcctgctgtg gccgagggga ccgggtgtgt ttggctcttt atgccctcc    2356 cgctgtggtc ctggaactct tcaccaggga gggagccctg cggggccgc agctttgtgg    2416 agggagccgc cgtgcttctg tcacctgctc cctttcttgc gtctccctgt gatgggccct   2476
taggcctggc tgggcccatt acatatccct gtggtggctc tggtggcagc tttctgtggc   2536
ccctgctgtg ttggcaggca ggtttgcgtg gtgaggagcg ggaggggttg gagtggtgcg   2596
ggagcaggct gccgagtgga gggtgccatc gagggctccg gatcccttat cctacttagc   2656
agtgttggtc tctggggctg gaagccgagc gcatgctggg agcggtactg tcagaagtga   2716
gcccagttag taccccgctg gctcactgca cgagagagtc ctgccccgag ccctaggtgg   2776
ggccaggagg tgccttggag aagccagcca gagcagagag ggctgctgac ttccgtgtgg   2836
agcagagagg cctgagggcc tcctaaaagg tttaaatgtc cacgcctctc cagttgctga   2896
agtagggtct gagagaaccc tggcatcagc agacccaggg tgcttctgtc tcctgcagac   2956
cacgccaggg agtgcagaca ccaccgtcac acacgcccct tttgtgtttt ggttcaagtt   3016
tctcagagcc cctcagagct tctacatctg tgcatcagaa atctcacagc cttctcatgc   3076
tgccggctca tctgggccca tagagtgggc tttgccagtt gctgttgcac aggaggcgag   3136
aacagcacac ttcaaccca gcttgctggt cggctttcct ctagagagag ccggttttgg   3196
ggccatttcc ctttgatgct ttggtggcct tgccccgctc tgcagcacag acaggccaga   3256
tgcatttgtc ctttgcctag ctactcccca ggtagagagt gctcctggtg gcctggcagg   3316
tctgggccct tctctccctg cccaggttgt cctggagggg cagccctcac tccctttggg   3376
ggagaggcag acattgctgc ccacagacct gcctctgact caactgtgtc caccctccct   3436
ggtccctacc cccaagtcac aggtgactca gcagtgaccc tgtgtgccag gccagatcca   3496
aactgagagg gaaggtgtcg tttttacact gctaatgacg agagtggctc ttttttagcta   3556 ggcgagtaca gacggggcct gggaggggc agagatgttc cccaggccct gcctgtggtt   3616
```

```
cctgcctggg ccttggctgc tgctgtgtga gagctgcatg tgagcctgtg accgtgagct    3676 gggtgagct gggccgcacc taccctgggg ccccagggag caggacgctc cggggcccag     3736
cacgttgccc tgggcctgtg gccggagtcg gagtcctctc tcctcctcct ggcttttgga    3796
aaggcttggc tgtgttgggg agtctctctt agcccttcca ggaatttctg ttcaggcttc    3856
ctcctcctca tcagctattt tacccatctc agaacgtcct gtgtctccat gtaggagagt    3916
ggctctctca gatctctcag ggcgtctggt tataggaaa caagtggagc agggacgtgg     3976 cttttaattgg agcactcggc tgggctgctt ggggagactc ttccgtgcgt tcttcctctg   4036
gatagaacca ccacctcctg ggcgtcactg acaagctcca tcttaacctc caaagccaca    4096
gaactagggg ctcagagcca gagctggcag ccgccagcca aaatgatgcc attgcctgag    4156
ctgacagcca agcccttctg tgggtcacct ttctcctcac ccagccctt gctcttccct     4216 tttgaaaggc ccgtgtgttt tctttcctta ccctgtgctt gctcatgtct actccggttt    4276
tctctaccac atccttagag ccatcacctg gcacgcaggc gccttacatt ctacggtaga    4336 acgtgggta ctgtgtgtgc acatagacac acttacgtgg aattacagtt gtgggtttat    4396
ccaagatgag gaagatttca cctgctgttt aatagacttg gggccatgtg cctccccaca    4456
catgggcaag acaggtgga atgtcgggac cacactgtgc ggcttctcgg cacaaagcgg     4516
agggaggctg tggtcgctgc cggcctaggt gtcccaggtg cccgccttt ctctgggaca     4576 cagttggggg ctggcttctg agggattcct ttctcccctc tttgtgtggc cccagccagg    4636
gcggtgggca gtcctggtgt agagcacaag cctctccacc ctagagaat gcctctgtac     4696 cacggctacc atgtggaacc ttaacttgca gaaggcttgt taacaattgt tttgagagag    4756
atggctggtc atgccacagc tgctggggac tccgcctact ccagccctct tgggacacac    4816
tgtgggattt gtgccccttc cccagaggaa ttgtggagac tgtcccatgg aacaaaccct    4876
caggcaccag cacagggctc tgggtgactc agtaaaacta acgtttgtct ctgacaagat    4936
cagctgtagg ctcaccggcc agagaagacc actgtgagca ttttgccgta tatcctgccc    4996
tgccatttgt tcactttta aactaaaata ggaacatccg acacacaccg tttgcatcgt     5056
cttctccctt gatatttaa gcattttccc atgtcatgag tttctcagaa acatgttttt     5116
aacaattgta ctatttagtc attgtccatt tactataatt tatctgacca tttccctact    5176
gtaaaatact taagacggtt tctgattttt ccactattta aataatgctg tgatgaatat    5236
ctttaaaatc ttctgatttc ttactttttt ccccttaga tgcctggaag tggtattttg     5296
aggtgaaaga gtttgttcat tttgaagata tttctgtctc tctctcgacc tgatgtgtag    5356
acgctcactt ccagtagcag aaccaccta gttgtgtctt acagattctg aacaaatcgg     5416
tttctgataa gccatgtgtt ccaaagaatg tctgaataag accgctcttt atttaaatgc    5476
taagaggatg tcactactgc aatccatctg tggccgattt tttccaagag ccaatttcct    5536
tgttttggtt gcaagaacct ggctctgcct gcatgtcagc tctctgccct ccctgctgcc    5596
gtggctttca agcgcttggc agaatcttgt acttcgtgtc cacaatggta ctgaatttgc    5656
atctgcacag tcagcagaga taacaagtgt tgaactgacc ttgccacatg cttagtgagt    5716
gatttgtaat taagttttata gactcagaag gtatattagg acatttggaa tcagtagcag    5776
agcaaagcct cttttgaaaaa aaccacgtag ctgattgggt tttacaagag tgcatttgtc    5836 tccccccttcc acccgtgggg ccccaccttc aggtcttagt ggttcacaag agcccagcag    5896
ccaggctggc ttttttcattg tagggcgtgg ttgtcccagc tggtgtagat ttcaggccgc     5956 ccccccaac tccctgccca cagtgttgca gattgcctgg ctggcagcaa gtccagacca    6016
```

-continued

```
cccaaatttg gttggattct tcatttctcc actgtagttg gggtccattg attgtgcagg   6076
ggaacgtgca ggaggttttt ctaggcaccg tgttcagtgc tgcttcactc taccagagat   6136
tatggccaaa ttgcacggaa tttggtttct tgccctctga agcctgaggg cccccccttg   6196
cctggctggt tgacagaccc ggggtggtca ctgctgagac ttcagagatc gcagctgctg   6256
tgagaatacg gtgaaggtac tttgttctgg aagatgttgt catacacttt tccccagtta   6316
ttttcaaact tgcatgagc ctatgttgac tcactgggtg ggggtcccctt cttacgcagc    6376 acacgtggca agtgcctgaa tcggggctgg aggcacttca gagcctctga ggggccacca   6436
cttctggccc aaaattgcag ggttgtagat gaggctgcct gtggagaact ggtgtgagga   6496
ggaagctgtt tccaacaaag agcactttca tctgttgaga tggctgtggt gagcaactga   6556
acgagcctac gtgtgtacct gaattttccc cgtaactcat tcttccata tgaagaaaca    6616 ccaaactatg tacagagaac tttttacaaa aggcagacct ttttaagct gtgtaaccca    6676 catagcctaa ccacctggca gaatgactac gaatagggt cattgtgctg gtaaaagcct    6736
ctattacgac tgtaagtaag ttggatgttg gcaaaattaa attgttacag tatttagagc   6796
tgctgtagct gttccttcac aacataaaat aggataaatg actagtacgt ctttcaggtg   6856
ggtggcaagc agaacatgcg taatattctc tacctggtct gtagctgtaa ctgtgatgta   6916
cagacaaagc aaaaattaaa agaacttatg aaaacaaatg caatgatact aggatataca   6976
cttttgtatt tttattctta tataaggtta tttgctggct attgttggcc tctagttcag   7036
tctgtgttat ttaaattcta atatatgaat tatttgaatt gaattcatgt tcggggccac    7096
gttgttgtat gtattgatgt acagccttga atgtgaataa ttattgtaaa ctatatttta    7156
caactttttt tctggcttta ttatataaat tttctattgg gtcagtgatt taatcatata   7216
atttaatgaa tctgtttatc cttttttttt ttccaaatac ttgtgcttta ggtgtagtta   7276
ccagatgatg aattttcctc gtatggtcag tagtcttgta ataaaaagca tgtagagtgt   7336
a                                                                   7337
```

<210> SEQ ID NO 9
<211> LENGTH: 529
<212> TYPE: PRT
<213> ORGANISM: Homo sapiens

<400> SEQUENCE: 9

```
Met Val Arg Thr Gln Thr Glu Ser Ser Thr Pro Pro Gly Ile Pro Gly
  1               5                  10                  15

Gly Ser Arg Gln Gly Pro Ala Met Asp Gly Thr Ala Ala Glu Pro Arg
             20                  25                  30

Pro Gly Ala Gly Ser Leu Gln His Ala Gln Pro Pro Gln Pro Arg
         35                  40                  45

Lys Lys Arg Pro Glu Asp Phe Lys Phe Gly Lys Ile Leu Gly Glu Gly
     50                  55                  60

Ser Phe Ser Thr Val Val Leu Ala Arg Glu Leu Ala Thr Ser Arg Glu
 65                  70                  75                  80

Tyr Ala Ile Lys Ile Leu Glu Lys Arg His Ile Ile Lys Glu Asn Lys
                 85                  90                  95

Val Pro Tyr Val Thr Arg Glu Arg Asp Val Met Ser Arg Leu Asp His
            100                 105                 110

Pro Phe Phe Val Lys Leu Tyr Phe Thr Phe Gln Asp Asp Glu Lys Leu
        115                 120                 125
```

```
Tyr Phe Gly Leu Ser Tyr Ala Lys Asn Gly Glu Leu Leu Lys Tyr Ile
    130                 135                 140

Arg Lys Ile Gly Ser Phe Asp Glu Thr Cys Thr Arg Phe Tyr Thr Ala
145                 150                 155                 160

Glu Ile Val Ser Ala Leu Glu Tyr Leu His Gly Lys Gly Ile Ile His
                165                 170                 175

Arg Asp Leu Lys Pro Glu Asn Ile Leu Leu Asn Glu Asp Met His Ile
            180                 185                 190

Gln Ile Thr Asp Phe Gly Thr Ala Lys Val Leu Ser Pro Glu Ser Lys
        195                 200                 205

Gln Ala Arg Ala Asn Ser Phe Val Gly Thr Ala Gln Tyr Val Ser Pro
    210                 215                 220

Glu Leu Leu Thr Glu Lys Ser Ala Cys Lys Ser Ser Asp Leu Trp Ala
225                 230                 235                 240

Leu Gly Cys Ile Ile Tyr Gln Leu Val Ala Gly Leu Pro Pro Phe Arg
                245                 250                 255

Ala Gly Asn Glu Tyr Leu Ile Phe Gln Lys Ile Ile Lys Leu Glu Tyr
            260                 265                 270

Asp Phe Pro Glu Lys Phe Phe Pro Lys Ala Arg Asp Leu Val Glu Lys
        275                 280                 285

Leu Leu Val Leu Asp Ala Thr Lys Arg Leu Gly Cys Glu Glu Met Glu
    290                 295                 300

Gly Tyr Gly Pro Leu Lys Ala His Pro Phe Phe Glu Ser Val Thr Trp
305                 310                 315                 320

Glu Asn Leu His Gln Gln Thr Pro Pro Lys Leu Thr Ala Tyr Leu Pro
                325                 330                 335

Ala Met Ser Glu Asp Asp Glu Asp Cys Tyr Gly Asn Tyr Asp Asn Leu
            340                 345                 350

Leu Ser Gln Phe Gly Cys Met Gln Val Ser Ser Ser Ser Ser Ser His
        355                 360                 365

Ser Leu Ser Ala Ser Asp Thr Gly Leu Pro Gln Arg Ser Gly Ser Asn
    370                 375                 380

Ile Glu Gln Tyr Ile His Asp Leu Asp Ser Asn Ser Phe Glu Leu Asp
385                 390                 395                 400

Leu Gln Phe Ser Glu Asp Glu Lys Arg Leu Leu Leu Glu Lys Gln Ala
                405                 410                 415

Gly Gly Asn Pro Trp His Gln Phe Val Glu Asn Asn Leu Ile Leu Lys
            420                 425                 430

Met Gly Pro Val Asp Lys Arg Lys Gly Leu Phe Ala Arg Arg Arg Gln
        435                 440                 445

Leu Leu Leu Thr Glu Gly Pro His Leu Tyr Tyr Val Asp Pro Val Asn
    450                 455                 460

Lys Val Leu Lys Gly Glu Ile Pro Trp Ser Gln Glu Leu Arg Pro Glu
465                 470                 475                 480

Ala Lys Asn Phe Lys Thr Phe Phe Val His Thr Pro Asn Arg Thr Tyr
                485                 490                 495

Tyr Leu Met Asp Pro Ser Gly Asn Ala His Lys Trp Cys Arg Lys Ile
            500                 505                 510

Gln Glu Val Trp Arg Gln Arg Tyr Gln Ser His Pro Asp Ala Ala Val
        515                 520                 525

Gln
```

```
<210> SEQ ID NO 10
<211> LENGTH: 1968
<212> TYPE: DNA
<213> ORGANISM: Homo sapiens
<220> FEATURE:
<221> NAME/KEY: CDS
<222> LOCATION: (1)..(1968)

<400> SEQUENCE: 10 atg gtt ttg tac acg acc ccc ttt cct aac agc tgt ctg tcc gcc ctg        48
Met Val Leu Tyr Thr Thr Pro Phe Pro Asn Ser Cys Leu Ser Ala Leu
1               5                  10                  15 cac tgt gtg tcc tgg gcc ctt atc ttt cca tgc tac tgg ctg gtg gac        96
His Cys Val Ser Trp Ala Leu Ile Phe Pro Cys Tyr Trp Leu Val Asp
            20                  25                  30 cgg ctc gct gcc tcc ttc ata ccc acc acc tac gag aag cgc cag cgg       144
Arg Leu Ala Ala Ser Phe Ile Pro Thr Thr Tyr Glu Lys Arg Gln Arg
        35                  40                  45 gca gac gac ccg tgc tgc ctg cag ctg ctc tgc act gcc ctc ttc acg       192
Ala Asp Asp Pro Cys Cys Leu Gln Leu Leu Cys Thr Ala Leu Phe Thr
    50                  55                  60 ccc atc tac ctg gcc ctc ctg gtg gcc tcg ctg ccc ttt gcg ttt ctc       240
Pro Ile Tyr Leu Ala Leu Leu Val Ala Ser Leu Pro Phe Ala Phe Leu
65                  70                  75                  80 ggc ttt ctc ttc tgg tcc cca ctg cag tcg gcc cgg ccc tac atc           288
Gly Phe Leu Phe Trp Ser Pro Leu Gln Ser Ala Arg Arg Pro Tyr Ile
                85                  90                  95 tat tca cgg ctg gaa gac aag ggc ctg gcc ggt ggg gca gcc ctg ctc       336
Tyr Ser Arg Leu Glu Asp Lys Gly Leu Ala Gly Gly Ala Ala Leu Leu
            100                 105                 110 agt gaa tgg aag ggc acg ggg cct ggg aaa agc ttc tgc ttt gcc act       384
Ser Glu Trp Lys Gly Thr Gly Pro Gly Lys Ser Phe Cys Phe Ala Thr
        115                 120                 125 gcc aac gtc tgc ctc ctg ccc gac tca ctc gcc agg gtc aac aac ctt       432
Ala Asn Val Cys Leu Leu Pro Asp Ser Leu Ala Arg Val Asn Asn Leu
    130                 135                 140 ttt aac acc caa gcg cgg gcc aag gag atc ggg cag aga atc cgc aat       480
Phe Asn Thr Gln Ala Arg Ala Lys Glu Ile Gly Gln Arg Ile Arg Asn
145                 150                 155                 160 ggg gcc gcc cgg ccc cag atc aaa att tac atc gac tcc ccc acc aat       528
Gly Ala Ala Arg Pro Gln Ile Lys Ile Tyr Ile Asp Ser Pro Thr Asn
                165                 170                 175 acc tcc atc agc gcc gct agc ttc agc agc ctg gtg tca cca cag ggc       576
Thr Ser Ile Ser Ala Ala Ser Phe Ser Ser Leu Val Ser Pro Gln Gly
            180                 185                 190 ggc gat ggg gtg gcc cgg gcc gtc ccc ggg agc att aag agg aca gcc       624
Gly Asp Gly Val Ala Arg Ala Val Pro Gly Ser Ile Lys Arg Thr Ala
        195                 200                 205 tct gtg gag tac aag ggt gac ggt ggg cgg cac ccc ggt gac gag gct       672
Ser Val Glu Tyr Lys Gly Asp Gly Gly Arg His Pro Gly Asp Glu Ala
    210                 215                 220 gcc aac ggc cca gcc tct ggg gac cct gtc gac agc agc ccg gag           720
Ala Asn Gly Pro Ala Ser Gly Asp Pro Val Asp Ser Ser Ser Pro Glu
225                 230                 235                 240 gat gcc tgc atc gtg cgc atc ggt ggc gag gag ggc cgg cca cct           768
Asp Ala Cys Ile Val Arg Ile Gly Gly Glu Glu Gly Gly Arg Pro Pro
                245                 250                 255 gaa gct gac gac cct gtg cct ggg ggc cag gcc agg aac gga gct ggc       816
Glu Ala Asp Asp Pro Val Pro Gly Gly Gln Ala Arg Asn Gly Ala Gly
            260                 265                 270
```

| | | |
|---|---|---|
| ggg ggc cca agg ggc cag acg ccc aac cat aat cag cag gac ggg gat<br>Gly Gly Pro Arg Gly Gln Thr Pro Asn His Asn Gln Gln Asp Gly Asp<br>              275                            280                          285 | 864 |
| tca ggg agc ctg ggc agc ccc tcg gcc tcc cgg gag tcc ctg gtg aag<br>Ser Gly Ser Leu Gly Ser Pro Ser Ala Ser Arg Glu Ser Leu Val Lys<br>    290                          295                          300 | 912 |
| ggg cga gct ggg cca gac acc agt gcc agc ggg gag cca ggt gcc aac<br>Gly Arg Ala Gly Pro Asp Thr Ser Ala Ser Gly Glu Pro Gly Ala Asn<br>305                            310                          315                      320 | 960 |
| agc aag ctc ctg tac aag gcc tcg gtg gtg aag aag gcg gct gca cgc<br>Ser Lys Leu Leu Tyr Lys Ala Ser Val Val Lys Lys Ala Ala Ala Arg<br>                        325                            330                          335 | 1008 |
| agg agg cgg cac ccc gac gag gcc ttc gac cat gag gtc tcc gcc ttc<br>Arg Arg Arg His Pro Asp Glu Ala Phe Asp His Glu Val Ser Ala Phe<br>              340                            345                          350 | 1056 |
| ttc ccc gcc aac ctg gac ttc ctg tgc ctg cag gag gtg ttt gac aag<br>Phe Pro Ala Asn Leu Asp Phe Leu Cys Leu Gln Glu Val Phe Asp Lys<br>    355                          360                          365 | 1104 |
| cga gca gcc acc aaa ttg aaa gag cag ctg cac ggc tac ttc gag tac<br>Arg Ala Ala Thr Lys Leu Lys Glu Gln Leu His Gly Tyr Phe Glu Tyr<br>370                            375                          380 | 1152 |
| atc ctg tac gac gtc ggg gtc tac ggc tgc cag ggc tgc tgc agc ttc<br>Ile Leu Tyr Asp Val Gly Val Tyr Gly Cys Gln Gly Cys Cys Ser Phe<br>385                            390                          395                      400 | 1200 |
| aag tgt ctc aac agc ggc ctc ctc ttt gcc agc cgc tac ccc atc atg<br>Lys Cys Leu Asn Ser Gly Leu Leu Phe Ala Ser Arg Tyr Pro Ile Met<br>                        405                            410                          415 | 1248 |
| gac gtg gcc tat cac tgt tac ccc aac aag tgt aac gac gat gcc ctg<br>Asp Val Ala Tyr His Cys Tyr Pro Asn Lys Cys Asn Asp Asp Ala Leu<br>                      420                          425                          430 | 1296 |
| gcc tct aag gga gct ctg ttt ctc aag gtg cag gtg gga agc aca cct<br>Ala Ser Lys Gly Ala Leu Phe Leu Lys Val Gln Val Gly Ser Thr Pro<br>                        435                            440                          445 | 1344 |
| cag gac caa aga atc gtc ggg tac atc gcc tgc aca cac ctg cat gcc<br>Gln Asp Gln Arg Ile Val Gly Tyr Ile Ala Cys Thr His Leu His Ala<br>450                            455                          460 | 1392 |
| cca caa gag gac agc gcc atc cgg tgt ggg cag ctg gac ctg ctt cag<br>Pro Gln Glu Asp Ser Ala Ile Arg Cys Gly Gln Leu Asp Leu Leu Gln<br>465                            470                          475                      480 | 1440 |
| gac tgg ctg gct gat ttc cga aaa tct acc tcc tcg tcc agc gca gcc<br>Asp Trp Leu Ala Asp Phe Arg Lys Ser Thr Ser Ser Ser Ser Ala Ala<br>                        485                            490                          495 | 1488 |
| aac ccc gag gag ctg gtg gca ttt gac gtc gtc tgt gga gat ttc aac<br>Asn Pro Glu Glu Leu Val Ala Phe Asp Val Val Cys Gly Asp Phe Asn<br>                      500                          505                          510 | 1536 |
| ttt gat aac tgc tcc tct gac gac aag ctg gag cag caa cac tcc ctg<br>Phe Asp Asn Cys Ser Ser Asp Asp Lys Leu Glu Gln Gln His Ser Leu<br>                        515                            520                          525 | 1584 |
| ttc acc cac tac agg gac ccc tgc cgc ctg ggg cct ggt gag gag aag<br>Phe Thr His Tyr Arg Asp Pro Cys Arg Leu Gly Pro Gly Glu Glu Lys<br>530                            535                          540 | 1632 |
| ccg tgg gcc atc ggt act ctg ctg gac acg aac ggc ctg tac gat gag<br>Pro Trp Ala Ile Gly Thr Leu Leu Asp Thr Asn Gly Leu Tyr Asp Glu<br>545                            550                          555                      560 | 1680 |
| gat gtg tgc acc ccc gac aac ctg cag aag gtc ctg gag agt gag gag<br>Asp Val Cys Thr Pro Asp Asn Leu Gln Lys Val Leu Glu Ser Glu Glu<br>                        565                            570                          575 | 1728 |
| ggc cgc agg gag tac ctg gcg ttt ccc acc agc aag agc tcg ggc cag<br>Gly Arg Arg Glu Tyr Leu Ala Phe Pro Thr Ser Lys Ser Ser Gly Gln<br>                      580                          585                          590 | 1776 |

| | | | | | | | | | | | | | | | |
|---|---|---|---|---|---|---|---|---|---|---|---|---|---|---|---|
| aag | ggg | cgg | aag | gag | ctg | ctg | aag | ggc | aac | ggc | cgg | cgc | atc | gac | tac | 1824 |
| Lys | Gly | Arg | Lys | Glu | Leu | Leu | Lys | Gly | Asn | Gly | Arg | Arg | Ile | Asp | Tyr | |
| | 595 | | | | 600 | | | | | 605 | | | | | | |
| atg | ctg | cat | gca | gag | gag | ggg | ctg | tgc | cca | gac | tgg | aag | gcc | gag | gtg | 1872 |
| Met | Leu | His | Ala | Glu | Glu | Gly | Leu | Cys | Pro | Asp | Trp | Lys | Ala | Glu | Val | |
| 610 | | | | | 615 | | | | | 620 | | | | | | |
| gaa | gaa | ttc | agt | ttt | atc | acc | cag | ctg | tcc | ggc | ctg | acg | gac | cac | ctg | 1920 |
| Glu | Glu | Phe | Ser | Phe | Ile | Thr | Gln | Leu | Ser | Gly | Leu | Thr | Asp | His | Leu | |
| 625 | | | | | 630 | | | | | 635 | | | | | 640 | |
| cca | gta | gcc | atg | cga | ctg | atg | gtg | tct | tcg | ggg | gag | gag | gag | gca | tag | 1968 |
| Pro | Val | Ala | Met | Arg | Leu | Met | Val | Ser | Ser | Gly | Glu | Glu | Glu | Ala | | |
| | | | | 645 | | | | | 650 | | | | | 655 | | |

<210> SEQ ID NO 11
<211> LENGTH: 655
<212> TYPE: PRT
<213> ORGANISM: Homo sapiens

<400> SEQUENCE: 11

Met Val Leu Tyr Thr Thr Pro Phe Pro Asn Ser Cys Leu Ser Ala Leu
1               5                   10                  15

His Cys Val Ser Trp Ala Leu Ile Phe Pro Cys Tyr Trp Leu Val Asp
            20                  25                  30

Arg Leu Ala Ala Ser Phe Ile Pro Thr Thr Tyr Glu Lys Arg Gln Arg
        35                  40                  45

Ala Asp Asp Pro Cys Cys Leu Gln Leu Leu Cys Thr Ala Leu Phe Thr
    50                  55                  60

Pro Ile Tyr Leu Ala Leu Leu Val Ala Ser Leu Pro Phe Ala Phe Leu
65                  70                  75                  80

Gly Phe Leu Phe Trp Ser Pro Leu Gln Ser Ala Arg Arg Pro Tyr Ile
                85                  90                  95

Tyr Ser Arg Leu Glu Asp Lys Gly Leu Ala Gly Gly Ala Ala Leu Leu
            100                 105                 110

Ser Glu Trp Lys Gly Thr Gly Pro Gly Lys Ser Phe Cys Phe Ala Thr
        115                 120                 125

Ala Asn Val Cys Leu Leu Pro Asp Ser Leu Ala Arg Val Asn Asn Leu
    130                 135                 140

Phe Asn Thr Gln Ala Arg Ala Lys Glu Ile Gly Gln Arg Ile Arg Asn
145                 150                 155                 160

Gly Ala Ala Arg Pro Gln Ile Lys Ile Tyr Ile Asp Ser Pro Thr Asn
                165                 170                 175

Thr Ser Ile Ser Ala Ala Ser Phe Ser Ser Leu Val Ser Pro Gln Gly
            180                 185                 190

Gly Asp Gly Val Ala Arg Ala Val Pro Gly Ser Ile Lys Arg Thr Ala
        195                 200                 205

Ser Val Glu Tyr Lys Gly Asp Gly Gly Arg His Pro Gly Asp Glu Ala
    210                 215                 220

Ala Asn Gly Pro Ala Ser Gly Asp Pro Val Asp Ser Ser Ser Pro Glu
225                 230                 235                 240

Asp Ala Cys Ile Val Arg Ile Gly Gly Glu Gly Gly Arg Pro
                245                 250                 255

Glu Ala Asp Asp Pro Val Pro Gly Gly Gln Ala Arg Asn Gly Ala Gly
            260                 265                 270

Gly Gly Pro Arg Gly Gln Thr Pro Asn His Asn Gln Gln Asp Gly Asp
        275                 280                 285

```
Ser Gly Ser Leu Gly Ser Pro Ser Ala Ser Arg Glu Ser Leu Val Lys
    290                 295                 300
Gly Arg Ala Gly Pro Asp Thr Ser Ala Ser Gly Glu Pro Gly Ala Asn
305                 310                 315                 320
Ser Lys Leu Leu Tyr Lys Ala Ser Val Val Lys Lys Ala Ala Ala Arg
                325                 330                 335
Arg Arg Arg His Pro Asp Glu Ala Phe Asp His Glu Val Ser Ala Phe
                340                 345                 350
Phe Pro Ala Asn Leu Asp Phe Leu Cys Leu Gln Glu Val Phe Asp Lys
            355                 360                 365
Arg Ala Ala Thr Lys Leu Lys Glu Gln Leu His Gly Tyr Phe Glu Tyr
370                 375                 380
Ile Leu Tyr Asp Val Gly Val Tyr Gly Cys Gln Gly Cys Cys Ser Phe
385                 390                 395                 400
Lys Cys Leu Asn Ser Gly Leu Leu Phe Ala Ser Arg Tyr Pro Ile Met
                405                 410                 415
Asp Val Ala Tyr His Cys Tyr Pro Asn Lys Cys Asn Asp Asp Ala Leu
                420                 425                 430
Ala Ser Lys Gly Ala Leu Phe Leu Lys Val Gln Val Gly Ser Thr Pro
            435                 440                 445
Gln Asp Gln Arg Ile Val Gly Tyr Ile Ala Cys Thr His Leu His Ala
450                 455                 460
Pro Gln Glu Asp Ser Ala Ile Arg Cys Gly Leu Asp Leu Leu Gln
465                 470                 475                 480
Asp Trp Leu Ala Asp Phe Arg Lys Ser Thr Ser Ser Ser Ala Ala
                485                 490                 495
Asn Pro Glu Glu Leu Val Ala Phe Asp Val Val Cys Gly Asp Phe Asn
                500                 505                 510
Phe Asp Asn Cys Ser Ser Asp Asp Lys Leu Glu Gln Gln His Ser Leu
            515                 520                 525
Phe Thr His Tyr Arg Asp Pro Cys Arg Leu Gly Pro Gly Glu Glu Lys
530                 535                 540
Pro Trp Ala Ile Gly Thr Leu Leu Asp Thr Asn Gly Leu Tyr Asp Glu
545                 550                 555                 560
Asp Val Cys Thr Pro Asp Asn Leu Gln Lys Val Leu Glu Ser Glu Glu
                565                 570                 575
Gly Arg Arg Glu Tyr Leu Ala Phe Pro Thr Ser Lys Ser Ser Gly Gln
                580                 585                 590
Lys Gly Arg Lys Glu Leu Leu Lys Gly Asn Gly Arg Arg Ile Asp Tyr
            595                 600                 605
Met Leu His Ala Glu Glu Gly Leu Cys Pro Asp Trp Lys Ala Glu Val
610                 615                 620
Glu Glu Phe Ser Phe Ile Thr Gln Leu Ser Gly Leu Thr Asp His Leu
625                 630                 635                 640
Pro Val Ala Met Arg Leu Met Val Ser Ser Gly Glu Glu Glu Ala
                645                 650                 655
```

<210> SEQ ID NO 12
<211> LENGTH: 7003
<212> TYPE: DNA
<213> ORGANISM: Homo sapiens
<220> FEATURE:
<221> NAME/KEY: CDS
<222> LOCATION: (244)..(900)

<400> SEQUENCE: 12

```
actcgcagtc ctgacgggca ggggctgcgg accgcccggc cttggaccca tccggagcca       60
caggttggag gagataagta gctgtccccg tgctcatcgc cctgtggagc agatcctgtc      120
tccttgctga cggtggagcc cgggagttcc agggcttggg aaggggaagg aaacctctct      180
gaaatctgac acctgctctc ccggcaagga aacttcgcag gctgaccgac caagaccatc      240
```

| | | | | | | | | | | | | | | | |
|---|---|---|---|---|---|---|---|---|---|---|---|---|---|---|---|
| act | atg | acc | gat | gga | gac | tat | gat | tat | ctg | atc | aaa | ctc | ctg | gcc | ctc |   288 |
|  | Met | Thr | Asp | Gly | Asp | Tyr | Asp | Tyr | Leu | Ile | Lys | Leu | Leu | Ala | Leu |  |
|  | 1 |  |  | 5 |  |  |  |  | 10 |  |  |  |  | 15 |  |  |

| | | | | | | | | | | | | | | | |
|---|---|---|---|---|---|---|---|---|---|---|---|---|---|---|---|
| ggg | gat | tca | ggg | gtg | ggg | aag | aca | aca | ttt | ctt | tat | aga | tac | aca | gat |   336 |
| Gly | Asp | Ser | Gly | Val | Gly | Lys | Thr | Thr | Phe | Leu | Tyr | Arg | Tyr | Thr | Asp |  |
|  |  |  | 20 |  |  |  |  | 25 |  |  |  |  | 30 |  |  |  |

| | | | | | | | | | | | | | | | |
|---|---|---|---|---|---|---|---|---|---|---|---|---|---|---|---|
| aat | aaa | ttc | aat | ccc | aaa | ttc | atc | act | aca | gta | gga | ata | gac | ttt | cgg |   384 |
| Asn | Lys | Phe | Asn | Pro | Lys | Phe | Ile | Thr | Thr | Val | Gly | Ile | Asp | Phe | Arg |  |
|  |  | 35 |  |  |  |  | 40 |  |  |  |  | 45 |  |  |  |  |

| | | | | | | | | | | | | | | | |
|---|---|---|---|---|---|---|---|---|---|---|---|---|---|---|---|
| gaa | aaa | cgt | gtg | gtt | tat | aat | gca | caa | gga | ccg | aat | gga | tct | tca | ggg |   432 |
| Glu | Lys | Arg | Val | Val | Tyr | Asn | Ala | Gln | Gly | Pro | Asn | Gly | Ser | Ser | Gly |  |
|  | 50 |  |  |  |  | 55 |  |  |  |  | 60 |  |  |  |  |  |

| | | | | | | | | | | | | | | | |
|---|---|---|---|---|---|---|---|---|---|---|---|---|---|---|---|
| aaa | gca | ttt | aaa | gtg | cat | ctt | cag | ctt | tgg | gac | act | gcg | gga | caa | gag |   480 |
| Lys | Ala | Phe | Lys | Val | His | Leu | Gln | Leu | Trp | Asp | Thr | Ala | Gly | Gln | Glu |  |
| 65 |  |  |  |  | 70 |  |  |  |  | 75 |  |  |  |  |  |  |

| | | | | | | | | | | | | | | | |
|---|---|---|---|---|---|---|---|---|---|---|---|---|---|---|---|
| cgg | ttc | cgg | agt | ctc | acc | act | gca | ttt | ttc | aga | gac | gcc | atg | ggc | ttc |   528 |
| Arg | Phe | Arg | Ser | Leu | Thr | Thr | Ala | Phe | Phe | Arg | Asp | Ala | Met | Gly | Phe |  |
| 80 |  |  |  |  | 85 |  |  |  |  | 90 |  |  |  |  | 95 |  |

| | | | | | | | | | | | | | | | |
|---|---|---|---|---|---|---|---|---|---|---|---|---|---|---|---|
| tta | tta | atg | ttt | gac | ctc | acc | agt | caa | cag | agc | ttc | tta | aat | gtc | aga |   576 |
| Leu | Leu | Met | Phe | Asp | Leu | Thr | Ser | Gln | Gln | Ser | Phe | Leu | Asn | Val | Arg |  |
|  |  |  | 100 |  |  |  |  | 105 |  |  |  |  | 110 |  |  |  |

| | | | | | | | | | | | | | | | |
|---|---|---|---|---|---|---|---|---|---|---|---|---|---|---|---|
| aac | tgg | atg | agc | caa | ctg | caa | gca | aat | gct | tat | tgt | gaa | aat | cca | gat |   624 |
| Asn | Trp | Met | Ser | Gln | Leu | Gln | Ala | Asn | Ala | Tyr | Cys | Glu | Asn | Pro | Asp |  |
|  |  | 115 |  |  |  |  | 120 |  |  |  |  | 125 |  |  |  |  |

| | | | | | | | | | | | | | | | |
|---|---|---|---|---|---|---|---|---|---|---|---|---|---|---|---|
| ata | gta | tta | att | ggc | aac | aag | gca | gac | cta | cca | gat | cag | agg | gaa | gtc |   672 |
| Ile | Val | Leu | Ile | Gly | Asn | Lys | Ala | Asp | Leu | Pro | Asp | Gln | Arg | Glu | Val |  |
|  |  | 130 |  |  |  |  | 135 |  |  |  |  | 140 |  |  |  |  |

| | | | | | | | | | | | | | | | |
|---|---|---|---|---|---|---|---|---|---|---|---|---|---|---|---|
| aat | gaa | cgg | caa | gct | cgg | gaa | ctg | gct | gac | aaa | tat | ggc | ata | cca | tat |   720 |
| Asn | Glu | Arg | Gln | Ala | Arg | Glu | Leu | Ala | Asp | Lys | Tyr | Gly | Ile | Pro | Tyr |  |
|  | 145 |  |  |  |  | 150 |  |  |  |  | 155 |  |  |  |  |  |

| | | | | | | | | | | | | | | | |
|---|---|---|---|---|---|---|---|---|---|---|---|---|---|---|---|
| ttt | gaa | aca | agt | gca | gca | act | gga | cag | aat | gtg | gag | aaa | gct | gta | gaa |   768 |
| Phe | Glu | Thr | Ser | Ala | Ala | Thr | Gly | Gln | Asn | Val | Glu | Lys | Ala | Val | Glu |  |
| 160 |  |  |  |  | 165 |  |  |  |  | 170 |  |  |  |  | 175 |  |

| | | | | | | | | | | | | | | | |
|---|---|---|---|---|---|---|---|---|---|---|---|---|---|---|---|
| acc | ctt | ttg | gac | tta | atc | atg | aag | cga | atg | gaa | cag | tgt | gtg | gag | aag |   816 |
| Thr | Leu | Leu | Asp | Leu | Ile | Met | Lys | Arg | Met | Glu | Gln | Cys | Val | Glu | Lys |  |
|  |  |  | 180 |  |  |  |  | 185 |  |  |  |  | 190 |  |  |  |

| | | | | | | | | | | | | | | | |
|---|---|---|---|---|---|---|---|---|---|---|---|---|---|---|---|
| aca | caa | atc | cct | gat | act | gtc | aat | ggt | gga | aat | tct | gga | aac | ttg | gat |   864 |
| Thr | Gln | Ile | Pro | Asp | Thr | Val | Asn | Gly | Gly | Asn | Ser | Gly | Asn | Leu | Asp |  |
|  |  | 195 |  |  |  |  | 200 |  |  |  |  | 205 |  |  |  |  |

| | | | | | | | | | |
|---|---|---|---|---|---|---|---|---|---|
| ggg | gaa | aag | cca | cca | gag | aag | aaa | tgt | atc | tgc | tag | actctacata |   910 |
| Gly | Glu | Lys | Pro | Pro | Glu | Lys | Lys | Cys | Ile | Cys |  |  |  |
|  | 210 |  |  |  |  | 215 |  |  |  |  |  |  |

```
gaaactgaac atcaagaacc ccaccaaaat attacttttta aaaacaatga caaaccacac      970
aattgttgtt gagtaaaccca cgcacaatgg catgtctttc tttttctgcc agaaaatcta     1030
ttttaagaaa ccagaatagt caacagtgtt caaaagaatt gactagttat ccctgaggcc     1090
ctttcaaaca tgatcaaaga tttcccaatg tgatctcatc atcatggata ctcaatttgt     1150 ttttctcttat agagaaaatg agtatataag acaatataca agaagaaata tcagtgagtt     1210
ttaaatcaga acaagttacc tgtcacattg aagaaaggg taggcactaa agggagaaca     1270
cagaaagaag aatttctaaa atattggatt tacttcttat attgagtcag atgcatactt     1330
```

-continued

```
ttagatttgc attggggaaa atgtactagc taaaaatgga tacacaatga agaattctat    1390
ttggctaatt aagaatgata tactatgtac acccaataag ctgtactaga atgaataaat    1450
tactgataag gttacaaata ggtaaatgtc acacttctgt taaaatgcag gaggtagtgt    1510
cataatgccg tctttatatt cttaataaat agcactttga caagaacagg actgtaaatg    1570
atgaagtaca agacaaatac cctgggaaaa aaatgaaag tatgagaaat tggcatttct     1630
acagctgaaa ttcaatgtat ctgttagaga tgtctggaag ggttacttag ccaaatttta    1690
ctcaagccaa ttaggagctg atattatcag ttggaattaa gagaactcca gaggtttcca    1750
tttcaaacaa aattttagaa attggtttgg tgttcagctt cacatttcat tttttcttag    1810
cacatgttga taaaatagtc acaaggagaa attaccagtt acggtttatt aaatctcttt    1870
taaaatgcag tcaaggaaaa ctagccttga atttttttta gataaaataa gatggtgata    1930
tgaaacaaaa agtggcaatt attgcaggtt tccttttagt ttacaaaagt actgaaaact    1990
aaatcatatt tcttccctcc aaatttcacc cattcctgac tttgaatcaa ttgcagaaat    2050
gcaggtgtgt tactttgttg atcaataact ttggaacaat tatggatcaa ttctatggtc    2110
actctgaatt ttcatgtcat taatcacata aaaattgata atacctcatt ctgtattaca    2170
atatgatttt attttgccaa aggcaagaca cctatagttg agctgtattt tggggggattg   2230 ggtgaggaag gacttctgat cttatctcaa caaaaaactg gccagtattt ttgttaatgt    2290
aaagcttcct tttctttcta aaaaatagta acaaaattat ttttcattgg cctattctgt    2350
tcttgtgtct aaactaacat tacattaatt tttaatctta gtttctgata aacacaagcc    2410
attcctatca aaatattatt tatttcagtc aatttaccaa ataacaaag acaatatatt     2470 ttcgtttttt tttattatga gcatatgatt ttttgacagg ctgtttcctc gtcgtataga    2530
ttttttccaa tcaaacctac ttttttccata ctctgtgcat atttttgtg aagttataca    2590 cattgaagac cctaaaaatc ccagtccatc attcagctta cctctgcgaa cttctatctg    2650
gtattgaatc agtttcagaa acacagacag atccaaggaa atgtctcttt ataatgttct    2710
taggatggac tagacccata aatgtgccat gaatcaaaat attaataatt tgaaagcttt    2770
catgctgtta gcccctgatg aaattctcag cattaactgg ccagctcctc tgatttctgc    2830
agcatcgcaa caggttcgaa gatgggttgt ggctgggtat tccctcccat ggtgtttcct    2890
ctgggatgct cttcattatc tcaatgcctg tgccatgaag atagaaaact gtaagctaac    2950
atttaagatg tttcttctgg aaggaaagtg agcaggaaca agttatattg ccactgctgt    3010
ggcaaatttt ggtgaacttt tggggtcatt atatcaattt tttctttgga ttcaaattgt    3070
aatgtcccct gcatttcctt aatagggaat gtgaaacctt tataaaactc taaaagtatt    3130
ctgttttgat atgtcttttt gtttctattc attttcagtt atatgattga tttacttatg    3190
ccaagattct gtcactgtca gttatttaat gagtgttttt tcagggtctg ttttaagatc    3250
attatttgat agctgtagca tgaagcagag gttgatgatg cccataattg caagactatt    3310
cctgtaaaaa taacaattat tgggtaataa cttcaagagg aatgagaagt gacaaaattg    3370
atttaaaata ttgttctact tataaataaa tgcttgatat aaaaaatttt ctccataaag    3430
tttgacatct gaccccagat tctatgtaat cattattaga aattccttct ctcattattt    3490
caggattagt agttctgtgt aattcatttt acaatttcaa attgttctgg tgccataaag    3550
tatacagact actttaaaga tttccaaatc ccctaattta ccccacaaca gcatgtaatt    3610
ttagccaaga tatgtcctgt tactaagtat ctcccaatgc tttagtaaaa cgtatttagg    3670
agaaatgttg aaaatgtaca tgaagctcct ttctgatata gaaaccattt ctggagtatt    3730
```

```
tacactggtt tgatgtttac attgctctaa ctcggtgcct cagatacctc tgtgaccaaa    3790
tttgtctcca accacatagc tcatttccta taatgttata tcataggaag ccctcacaga    3850
gacactaaca cagctaaaga tcttctgata ttatcagcaa gggatgcaag gactttattg    3910
gaatctggag agtttaactg ccttctcttg gtctcctcac ttacttctta tgaagttggc    3970
attacctgag actcttagct gtgattaggt acaagcttac cttttagggt agaaaaagaa    4030
agatcatttg aaaaatgtat ctaaaataat ccagagaaca taatgtttgt cttggtctga    4090
taatgataag aagtcaagga ttggcagaga aaatactaaa cgccaagagt tgagcctgtg    4150
ggtctctcca taagagtttt aaaactcttg ccagttacca ctttatccaa tttgctatca    4210
ttttcgtatt atcagctatc gccctgtaaa atattcaaaa ctagctattt ctaaagtaaa    4270
cattttatct gttacttttta accagatagg tgtctttgtc atccttctac tataaattgt    4330
tctttgccaa cctgtacagg tagatgaacc aggcgagagt tttaatcagc cttttcttgt    4390
cccctttgta agaaagagat gcttgccata gagaaggaca tgagtacatt aaaaataatt    4450
taatagccac aatatgatgt tctttaagct gcaaattgag tacactggga atcaacaaat    4510
ttgatgaagc ctgtctgtct cttcaccagt ggagtgagtg cagcagttag aaagagaagc    4570
aatattgtgc aactggtgca gtggtgagtt aatcatagtg tataaccttg tgttcatgaa    4630
acaggttgtt cattgttctg catctctctt catttaaaaa ggatacacaa ttctttcctc    4690
attgcatatt acaccaaacg tttgagggaa aaatcctcat tcgtaaagga ttttggatgt    4750
ataatctaaa actcaacaat aaagaaataa tattccaagt ctctggtttc ctaagataca    4810
taataactgt ttataaagaa ggtctaagag ctgatatttg ccaaagtgat agaagagttg    4870 tttttttcctc tctactacca agctttaaga cattaaaaga agtctagtgt atttgaatat    4930
tttagagaaa gctttatcat tttttaagat gccaagatgc tgcctacgtt tgcaaaagtt    4990
gtctaagaat tcaccatgag ctatattttc ttctggatct ttgaccaagg tgatgtcagc    5050
ttatttctgg ggaaggtgtt gagctcttat acatgaaaat ggatataggc tattctctgg    5110
gatgagtgtc atttcaatgc tttataaatc catgaagctg cttgtctcat aaagtagaac    5170
tgatacaaat tttggttgga tatatagaga atttttataaa tgtattgcct tagaatttct    5230
gggtggagac ccaactacaa tgacattgtc atgccagaac tataaagata attagagtta    5290
aaagttgttt aaattgtgcc cttaaataca gcagaacctg gagaaggtca tacttcaaag    5350
gtcgattttg agtccgaata aagaaagacc tagtaacaga tagtttttttt ttgttcattt    5410 tcttctacca agtagaggtt tatgccctca gaactaaact agtaaaaata tctgaacaaa    5470
aaacctttcg ttgttggcat aaaaatgtga tacacttaga gacattttgt ttattgcata    5530
taaatctaat ttttccataa attagattta tgatattttc ataaagcact tgattagttt    5590
ttcaaggcgt accatcacaa agatgctttc ctgcagagtt ctttgtatca acagcctatg    5650
gttgagatgt tttctcattt cctgtagaga gagaatacca ctaacaaaca aacaaaaact    5710
ttagtgccaa aatagtggaa ctattttgtc atcttttgag aaaaaaatat acaaagaagt    5770
catcttttca ttaagtggat tccctggttc cttttccagct ggttgtggaa gtaatggcta    5830
acatccttca gctgactttg tctacaagga ttattagcaa attctgtagg agcaagcatg    5890
tctgacctta acttaatgga tcccttattc aatcagtggc ttctgtcttt atgtctgttg    5950
gcatatcaaa atggtttctg ttcctagaaa agtaataaca tatgcttatc tttattcttt    6010
ttccaggtga ttttgttttc aaatgctcct tgtgaaaaca cctagtgttg tagaaaggaa    6070
agtggccaga aagaacaact tgggaccatg agtaggtcat taaatagctt agtgatttat    6130
```

```
cctcatatag ggcttataaa ccctgtatgt gtttatatgt gcttcacaga gttcgtgtca    6190
ggctcaaagg agatatgtat aagaaagtgg tttgtaaatt atgttccatt tcataaatag    6250
acactattca caaactaaaa tctaataaaa aaccacagtt gtaatttaaa ctgcttgata    6310 taaaagagg tatcatagca gggaaaacac actaattttc atacagtaga ggtattgaaa    6370
actgaaaatg ggaaggcaac ttgaagtcat tgtatttgat tgaaaatgtt taatacatct    6430
cattattgac aaaatatgtc atcttgtatt tatttcaagg aaaccaatga attctaggta    6490
gtatattaca agttggtcaa atattccat gtacaaatag ggcttctgtg tccatagcct     6550
tgtaagagat actgattgta tctgaaatta ttttttaaaa aaataaatta tcctgcttta    6610
gttagtgtgt taaaagtaga cgatgttcta atataacact gaagtgcttc attgtatccc    6670
aacagtttac cttcaagtaa tattatcttt attttaggc taagcacgtt tgattatttt     6730
gtctgtctcc tatatagatc tgttttgtct agtgctatga atgtaactta aaactataaa    6790
cttgaagttt ttattctata tgccccttaa tagactgtgg ttcctgacgc acactgttag    6850
gtcattattt tgttgtacca agttctagt ggcttcagaa atcatagcat ccaatgattt     6910
tttggtgtct ggctatgaat actatggttg agaattgtat tcagtgattg tttctgcaca    6970
cttttcaaat aaaaaatgaa tttttatcaa tta                                 7003

<210> SEQ ID NO 13
<211> LENGTH: 218
<212> TYPE: PRT
<213> ORGANISM: Homo sapiens

<400> SEQUENCE: 13

Met Thr Asp Gly Asp Tyr Asp Tyr Leu Ile Lys Leu Leu Ala Leu Gly
1               5                   10                  15

Asp Ser Gly Val Gly Lys Thr Thr Phe Leu Tyr Arg Tyr Thr Asp Asn
            20                  25                  30

Lys Phe Asn Pro Lys Phe Ile Thr Thr Val Gly Ile Asp Phe Arg Glu
        35                  40                  45

Lys Arg Val Val Tyr Asn Ala Gln Gly Pro Asn Gly Ser Ser Gly Lys
    50                  55                  60

Ala Phe Lys Val His Leu Gln Leu Trp Asp Thr Ala Gly Gln Glu Arg
65                  70                  75                  80

Phe Arg Ser Leu Thr Thr Ala Phe Phe Arg Asp Ala Met Gly Phe Leu
                85                  90                  95

Leu Met Phe Asp Leu Thr Ser Gln Gln Ser Phe Leu Asn Val Arg Asn
            100                 105                 110

Trp Met Ser Gln Leu Gln Ala Asn Ala Tyr Cys Glu Asn Pro Asp Ile
        115                 120                 125

Val Leu Ile Gly Asn Lys Ala Asp Leu Pro Asp Gln Arg Glu Val Asn
    130                 135                 140

Glu Arg Gln Ala Arg Glu Leu Ala Asp Lys Tyr Gly Ile Pro Tyr Phe
145                 150                 155                 160

Glu Thr Ser Ala Ala Thr Gly Gln Asn Val Glu Lys Ala Val Glu Thr
                165                 170                 175

Leu Leu Asp Leu Ile Met Lys Arg Met Glu Gln Cys Val Glu Lys Thr
            180                 185                 190

Gln Ile Pro Asp Thr Val Asn Gly Gly Asn Ser Gly Asn Leu Asp Gly
        195                 200                 205

Glu Lys Pro Pro Glu Lys Lys Cys Ile Cys
    210                 215
```

```
<210> SEQ ID NO 14
<211> LENGTH: 43
<212> TYPE: DNA
<213> ORGANISM: Macaca arctoides

<400> SEQUENCE: 14
ttgatgtaca gccttgaatg tgaataatta ttgtaaacta tat          43

<210> SEQ ID NO 15
<211> LENGTH: 43
<212> TYPE: DNA
<213> ORGANISM: Homo sapiens

<400> SEQUENCE: 15
ttgatgtaca gccttgaatg tgaataatta ttgtaaacta tat          43

<210> SEQ ID NO 16
<211> LENGTH: 30
<212> TYPE: DNA
<213> ORGANISM: Artificial Sequence
<220> FEATURE:
<223> OTHER INFORMATION: forward primer

<400> SEQUENCE: 16
aactcgagaa tgctggctat tgttggcctc                         30

<210> SEQ ID NO 17
<211> LENGTH: 34
<212> TYPE: DNA
<213> ORGANISM: Artificial Sequence
<220> FEATURE:
<223> OTHER INFORMATION: Reverse primer

<400> SEQUENCE: 17
aagcggccgc aagattaaat cactgaccca atag                    34
```

METHOD FOR DIAGNOSING AND TREATING CANCER BRAIN METASTASIS AND DRUG DELIVERY SYSTEM FOR ENABLING PASSAGE THROUGH BLOOD-BRAIN BARRIER

TECHNICAL FIELD

The present invention relates to the permeability control of the blood-brain barrier and particularly to a technique for increasing the permeability of the blood-brain barrier. The present invention further relates to the field of brain metastasis of cancer. More specifically, the present invention relates to the fields of diagnosis or risk assessment of brain metastasis and treatment or prevention of brain metastasis.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 2019-02-01_Substitute Sequence Listing_PRZ005001APC.TXT, the date of creation of the ASCII text file is Feb. 1, 2019, and the size of the ASCII text file is 103 KB.

BACKGROUND ART

Brain metastasis in cancer patient is known to relate to poor prognoses. Moreover, it also is known that passage of cancer cells through the blood-brain barrier (BBB) is an important event in brain metastasis, that main constituent cells of the BBB are brain microvascular endothelial cells (BMECs), and that BMECs are connected each other by tight junctions between cells and thereby have very selective permeability. Moreover, the proteins junctional adhesion molecules (JAM-1, JAM-2 and JAM-3), Occludin, Claudins, and Zonula Occludin proteins (ZO-1 and ZO-2) are known to constitute the tight junction. Furthermore, cyclooxygenase-2 (COX-2), the epidermal growth factor receptor (EGFR) ligand HB-EGF, and α 2,6-sialyltransferase (ST6GALNAC5) have been identified as mediators involved in the BBB invasion of cancer cells. However, the early stage molecule mechanisms of cancer cells passing through the BBB have not been revealed (Non Patent Literature 1). A study using a highly metastatic breast cancer cell line MDA-MB-231 has shown that vascular endothelial growth factor (VEGF) is highly expressed in breast cancer cells and increases the permeability of endothelial cells as well as adhesion of cancer cells onto endothelial cells, and thus VEGF is involved in the brain metastasis (Non Patent Literature 2). Although the expression of VEGF has been reported to be necessary for brain metastasis, it has been also reported that the expression of VEGF is not sufficient for brain metastasis, and the destruction mechanism of the BBB in brain metastasis has not been sufficiently explained by VEGF (Non Patent Literature 3).

A mechanism of BBB passage of *Cryptococcus neoformans* which infects the central nervous system (CNS) has been studied. It has been reported that the adhesion of *Cryptococcus* to human BMECs causes dephosphorylation of Cofilin, which results in actin rearrangement. This report further indicates that the dephosphorylation of Cofilin by *Cryptococcus* is controlled via the Rho kinase-LIM kinase-Cofilin pathway (Non Patent Literature 4).

Extracellular vesicles (EVs) including exosomes are known to mediate communication between cells by transporting protein, mRNA, and microRNA (miRNA) contained therein (Non Patent Literature 5). Moreover, it has been reported that extracellular vesicles released from cancer cells are involved in the malignancy of cancer cells in various ways (Non Patent Literature 8), for example, they inhibit the function of natural killer cells (Non Patent Literature 6) and increase the expression of the oncogene protein MET in bone marrow progenitor cells to change the bone marrow progenitor cells toward a pro-metastatic phenotype (Non Patent Literature 7). As seen above, the relation between EVs and cancer metastasis has been suggested. However, little was known about the relation between EVs (and substances contained therein) and the BBB.

CITATION LIST

Non Patent Literature

Non Patent Literature 1: Arshad, F. et al, Patholog Res Int 2011: 920509 (2010).
Non Patent Literature 2: Lee, T. H. et al, J Biol Chem 278: 5277-5284 (2003).
Non Patent Literature 3: Yano, S. et al, Cancer Res 60: 4959-4967 (2000).
Non Patent Literature 4: Chen, H. M. Steven, et al, Journal of Medical Microbiology 52: 961-970 (2003).
Non Patent Literature 5: Valadi, H. et al, Nat Cell Biol 9:654-659 (2007).
Non Patent Literature 6: Liu, Cunren, et al, The Journal of Immunology 176: 1375-1385 (2006):
Non Patent Literature 7: Peinado, H. et al, Nat Med 18: 883-891 (2012).
Non Patent Literature 8: Yang, C. et al, Clin Dev Immunol 2011: 842-849 (2011).

SUMMARY OF INVENTION

An object of the present invention is to elucidate mechanisms of the destruction of the BBB in brain metastasis, and to provide new methods for diagnosis/risk assessment and for treatment/prevention of brain metastasis of cancer. Another object of the present invention is to provide a novel method for agent delivery into brain using the mechanism of the BBB destruction. A further object of the present invention is to provide an agent, a composition, and a kit to be used in these methods.

To elucidate the mechanism of brain metastasis, the present inventors transplanted a highly metastatic human breast cancer cell line to mice, and analyzed EVs obtained from cancer cells metastasized to the brain. As a result, it was found that cancer cell-derived EVs are taken in brain microvascular endothelial cells and destruct the blood-brain barrier (BBB). The present inventors then searched for a substance related to the destruction of the blood-brain barrier from the substances contained in the EVs, and found that miR-181c, a microRNA specifically contained in the EVs derived from the brain metastatic cancer cells, has an effect to destruct the blood-brain barrier. The present inventors further examined the effect of miR-181c in brain microvascular endothelial cells, and found that miR-181c binds to a noncoding region of 3-phosphoinositide dependent protein kinase-1 (hereinafter referred to as "PDPK1") and decreases expression of PDPK1. The present inventors further examined the relation between the decreased expression of PDPK1 and the disruption of the blood-brain barrier (BBB), and found that the inhibition of PDPK1 expression changes the localization of tight junction proteins. Thus, the present inventors have found that cancer cell-derived EVs release miR-181c contained therein in brain microvascular endothelial cells, which inhibits the expression of PDPK1, and thereby change the localization of tight junction proteins to destruct the blood-brain barrier.

miR-181c has been reported to be involved in the aggravation of cells, but has not been known in relation with the blood-brain barrier.

Moreover, PDPK1 has been known to mainly target protein kinase B (PKB/AKT1, PKB/AKT2, PKB/AKT3), p70 ribosomal protein S6 kinase (RPS6KB1), p90 ribosomal protein S6 kinase (RPS6KA1, RPS6KA and RPS6KA3), cyclic AMP-dependent protein kinase (PRKACA), protein kinase C (PRKCD and PRKCZ), serum- and glucocorticoid-inducible kinase (SGK1, SGK2 and SGK3), P21 activated kinase-1 (PAK1), and protein kinase PKN (PKN1 and PKN2), and known to be involved in the regulation of cell proliferation and survival as well as intake and storage of glucose and amino acids. However, there has been no report on PDPK1 in relation with the blood-brain barrier.

Accordingly, the present invention is based on the elucidation of the mechanism for destruction of the blood-brain barrier by brain metastatic cancer cells, and specifically relates to the following inventions:

(1) A method for providing information for diagnosing brain metastasis, comprising measuring miR-181c level in a sample from a subject cancer patient.
(2) A method for providing information for diagnosing brain metastasis in a subject cancer patient, comprising the steps of:
determining miR-181c level in a sample from the subject cancer patient, and
judging brain metastasis in the subject cancer patient from the determined miR-181c level,
wherein when the miR-181c level of the sample from the subject cancer patient is higher than that from a negative control, information that the subject cancer patient has brain metastasis is provided.
(3) The method of (1) or (2), wherein the subject cancer patient is a Stage IV cancer patient.
(4) A method for providing information for diagnosing brain metastasis, comprising measuring miR-181c level in a sample from a subject cancer patient.
(5) A method for providing information for assessing risk of brain metastasis in a subject cancer patient, comprising the steps of:
determining miR-181c level in a sample from the subject cancer patient,
assessing risk of brain metastasis in the subject cancer patient from the determined miR-181c level,
wherein when the miR-181c level of the sample from the subject cancer patient is higher than that from a negative control, information that risk of brain metastasis is high in the subject cancer patient is provided.
(6) The method of (4) or (5), wherein the subject cancer patient is a Stage I to III cancer patient.
(7) The method of any one of (1) to (6), wherein the subject cancer patient is a breast cancer patient.
(8) The method of any one of (1) to (7), wherein the negative control is a cancer patient with no brain metastasis or a healthy subject.
(9) The method of any one of (1) to (8), wherein the sample is blood.
(10) The method of any one of (1) to (9), wherein the miR-181c in the sample is miR-181c extracted from EVs in the sample.
(11) An in vitro diagnostic reagent or an in vitro diagnostic measuring apparatus for diagnosis or risk assessment of brain metastasis by measuring miR181c, which is for use in a method of any one of (1) to (10).
(12) An agent for diagnosis or risk assessment of brain metastasis, comprising a substance that specifically binds to miR-181c.
(13) The agent of (12), wherein the substance that specifically binds to miR-181c is a nucleic acid that specifically binds to miR-181c.
(14) The agent of (13), wherein the nucleic acid that specifically binds to miR-181c is a nucleic acid at least partially having an artificially designed sequence.
(15) The agent of any one of (12) to (14), wherein the substance that specifically binds to miR-181c is labelled.
(16) A pharmaceutical composition for suppressing brain metastasis, comprising one or more agents selected from the group consisting of an miR-181c expression inhibitor, an miR-181c activity inhibitor, and an exosome secretion inhibitor as an active ingredient.
(17) The pharmaceutical composition of (16), wherein the one or more agents selected from the group consisting of an miR-181c expression inhibitor, an miR-181c activity inhibitor, and an exosome secretion inhibitor is an agent selected from:
(i) an antisense oligonucleotide, aptamer, or siRNA against pri-miR-181c or pre-miR-181c;
(ii) an antisense oligonucleotide to miR-181c, an aptamer that specifically binds to miR-181c, siRNA against miR-181c, or miRNA mimetics of miR-181c;
(iii) an antisense oligonucleotide, aptamer, or siRNA against the nSMase2 and/or RAB27B gene; or
(iv) an antibody or an immunoreactive fragment thereof against nSMase2 and/or RAB27B; peptide mimetics or an aptamer that specifically binds to nSMase2 and/or RAB27B; or an antagonist of nSMase2 and/or RAB27B.
(18) A pharmaceutical composition for increasing permeability of blood-brain barrier, comprising a PDPK1 expression inhibitor or PDPK1 activity inhibitor as an active ingredient.
(19) The pharmaceutical composition of (18), wherein the PDPK1 expression inhibitor or activity inhibitor is an antisense oligonucleotide against the PDPK1 gene, an aptamer that specifically binds to the PDPK1 gene, siRNA against the PDPK1 gene, or miRNA capable of suppressing the PDPK1 gene expression; or an antibody against PDPK1 or the immunoreactive fragment thereof; peptide mimetics or an aptamer that specifically binds to PDPK1; or an antagonist of PDPK1.
(20) The pharmaceutical composition of (19), wherein the miRNA capable of suppressing the PDPK1 gene expression is miR-181c.
(21) An agent-delivery composition for delivering a desired active ingredient into brain, comprising a PDPK1 expression inhibitor or PDPK1 activity inhibitor as an active ingredient.
(22) The agent-delivery composition of (21), comprising the desired active ingredient in addition to the PDPK1 expression inhibitor or activity inhibitor.
(23) The agent-delivery composition of (21) or (22), wherein the PDPK1 expression inhibitor or activity inhibitor is an antisense oligonucleotide against the PDPK1 gene, an aptamer that specifically binds to the PDPK1 gene, siRNA against the PDPK1 gene, or miRNA capable of suppressing the PDPK1 gene expression; or an antibody against PDPK1 or the immunoreactive fragment thereof; peptide mimetics or an aptamer that specifically binds to PDPK1; or an antagonist of PDPK1.

(24) The agent-delivery composition of (23), wherein the miRNA capable of suppressing the PDPK1 gene expression is miR-181c.

(25) An apparatus for judging brain metastasis in a subject cancer patient, comprising:

miR-181c-measuring means for measuring a polynucleotide having a nucleotide sequence of miR-181c or a part thereof in a sample from the subject cancer patient, miR-181c level-determining means for determining miR-181c level in the sample from the measurement by the miR-181c-measuring means, and metastasis-judging means for judging brain metastasis in the subject cancer patient from the determined miR-181c level by the miR-181c level-determining means;

wherein the metastasis-judging means judges that the subject cancer patient has brain metastasis when the miR-181c level in the sample from the subject cancer patient is higher than the miR-181c level in a sample from a negative control.

(26) An apparatus for assessing risk of brain metastasis in a subject cancer patient, comprising:

miR-181c-measuring means for measuring a polynucleotide having a nucleotide sequence of miR-181c or a part thereof in a sample from the subject cancer patient, miR-181c level-determining means for determining miR-181c level in the sample from the measurement by the miR-181c-measuring means, and risk-assessing means for assessing risk of brain metastasis in the subject cancer patient from the determined miR-181c level by the miR-181c level-determining means;

wherein the risk-assessing means assesses that the subject cancer patient has a high risk of brain metastasis when the miR-181c level in the sample from the subject cancer patient is higher than the miR-181c level in a sample from a negative control.

(27) A computer program to be installed in an apparatus for providing information for diagnosing brain metastasis in a subject cancer patient, wherein the computer program directs the apparatus for diagnosing brain metastasis in a cancer patient to execute:

an miR-181c-measuring procedure for measuring a polynucleotide having a nucleotide sequence of miR-181c or a part thereof in a sample from the subject cancer patient, an miR-181c level-determining procedure for determining an miR-181c level in the sample from the measurement by the miR-181c-measuring procedure, a metastasis-judging procedure for judging brain metastasis in the subject cancer patient from the determined miR-181c level by the miR-181c level-determining procedure, and a judgment-output procedure of outputting the judgment by the metastasis-judging procedure; and the metastasis-judging procedure judges that the subject cancer patient has brain metastasis when the miR-181c level in the sample from the subject cancer patient is higher than the miR-181c level in a sample from a negative control.

(28) A computer program to be installed in an apparatus for assessing risk of brain metastasis in a subject cancer patient, wherein the computer program directs the apparatus for diagnosing brain metastasis in a cancer patient to execute:

an miR-181c-measuring procedure for measuring a polynucleotide having a nucleotide sequence of miR-181c or a part thereof in a sample from the subject cancer patient, an miR-181c level-determining procedure for determining an miR-181c level in the sample from the measurement by the miR-181c-measuring procedure, a risk-assessing procedure for assessing risk of brain metastasis in the subject cancer patient from the determined miR-181c level by the miR-181c level-determining procedure;

an assessment-output procedure of outputting the assessment by the risk-assessing procedure; and the risk-assessing procedure assesses that the subject cancer patient has a high risk of brain metastasis when the miR-181c level in the sample from the subject cancer patient is higher than the miR-181c level in a sample from a negative control.

As used herein, the term "cancer" includes epithelial malignant tumors, hematopoietic malignant tumors derived from spinal cord, and the like, and particularly includes ovarian cancer (non-mucinous ovarian cancers and the like), uterine cancer, endometrial cancer, breast cancer, breast adenocarcinoma, prostate cancer, testicular cancer (testicular choriocarcinoma and the like), brain cancer (ependymoma and the like), throat cancer, lung cancer, lung adenocarcinoma, kidney cancer (renal cell cancer and the like), liver cancer, large bowel cancer (colon cancer), pleural mesothelioma, sarcoma, chronic and acute myeloid leukemia, and metastatic cancers such as lung metastatic cancer. As used herein, a "cancer patient" means a patient having cancer (at a site except the brain) with or without metastasis and may be a patient with, for example, hematopoietic cell malignant tumors such as leukemia, lymphomas (Hodgkin's disease and non-Hodgkin's lymphom, and the like), multiple myeloma; breast cancer; endometrial cancer; cervical cancer; ovarian cancer; esophageal cancer; gastric cancer; appendiceal cancer; large bowel cancer (colon cancer, rectal cancer, and the like); liver cancer (hepatocellular cancer, and the like); gallbladder cancer; bile duct cancer; pancreatic cancer; adrenal cancer; gastrointestinal stromal tumor; mesothelioma; head and neck cancers such as laryngeal cancer, oral cancers (oral floor cancer, gingival cancer, tongue cancer, buccal mucosa cancer, and the like); salivary gland cancer; nasal sinus cancers (maxillary sinus cancer, frontal sinus cancer, ethmoid cancer, sphenoidal sinus cancer, and the like); thyroid cancer; kidney cancer; lung cancer; osteosarcoma; prostate cancer; testicular tumor (testicular cancer); renal cell cancer; bladder cancer; rhabdomyosarcoma; skin cancer; or anal cancer.

The stage of cancer is determined according to a stage classification (clinical advanced stage classification). The detailed criteria for the stage classification of each cancer (organ) has been established, based on, for example, the size of cancer (T), metastasis to nearby lymph nodes (N) and metastasis to a distant organ (M) (TNM classification), which has been widely known in the art (see the website "Cancer staging" of U.S. National Cancer Center, on the World-Wide-Web at cancer.gov/cancertopics/factsheet/detection/staging; the latest edition of AJCC Cancer Staging Manual (American Joint Commitee on Cancer)). For example, the staging criteria for breast cancer is as follows. Stage 0: non-invasive cancer: the breast cancer stays in the mammary gland where it has developed (including the Paget's disease); Stage I: lump size of 2 cm or smaller without metastasis to the lymph nodes; Stage IIA: lump size of 2 cm or smaller with metastasis to the axillary lymph nodes, or lump size of 2.1-5 cm without metastasis to the lymph nodes; Stage IIB: lump size of 2.1-5 cm with metastasis to the axillary lymph, or lump size of 5.1 cm or larger without metastasis to the lymph nodes; Stage IIIA: lump size of 5.1 cm or larger with metastasis to the axillary lymph, any size of lump with heavy metastasis to the axillary lymph nodes, or any size of lump without metastasis to the axillary lymph nodes but with metastasis to parasternal lymph nodes; Stage IIIB: any size of lump with infiltration to the chest wall and/or skin; Stage IIIC: any size of lump with metastasis spread to infraclavicular or supraclavicular lymph nodes; Stage IV: metastasis to organs distant from the breast.

Patients at Stage IV in the cancer staging usually have metastasis to distant organs. Accordingly, in such patients, cancer cells have already invaded into the blood vessels, and therefore brain metastasis is very highly possible if miR-181c level in blood (in EVs contained in the blood) is high and the blood-brain barrier is open. On the other hand, in Stage I to III patients who do not have metastasis to distant organs, since cancer cell is not likely to invade into blood vessels, brain metastasis does not occur immediately even if the miR-181c level in blood (in EVs contained in blood) is high and the blood-brain barrier is open. However, these Stage I to III patients have high possibility (risk) of brain metastasis in the future invasion of cancer cells into the blood. Accordingly, whether a method, agent, apparatus, computer program or the like according to the present invention is used for diagnosis of brain metastasis or for risk assessment of brain metastasis can be determined according to a state of the patient from which the measured sample is derived. When the cancer staging is employed as the state, risk assessment of brain metastasis can be conducted for Stage I to III patients, and diagnosis of brain metastasis can be conducted for Stage IV patients. Instead of cancer staging, the presence or absence of metastasis to a distant organ or the presence or absence of infiltration of cancer cell into the blood may be employed as the state to select either of diagnosis of brain metastasis or risk assessment of brain metastasis. In this case, when there is metastasis to a distant organ or when there is infiltration of cancer cell into the blood, the present invention can be used for a diagnosis of brain metastasis, while when there is no metastasis to a distant organ or when there is no infiltration of cancer cell into the blood, the present invention is used for risk assessment of brain metastasis. Accordingly, as used herein, the "Stage IV patients" may be replaced with patients with metastasis to a distant organ or patients with infiltration of cancer cell into the blood. Also, the "Stage I to III patients" may be replaced with patients with no metastasis to a distant organ or patients with no infiltration of cancer cell into the blood.

As used herein, the "brain metastasis" and "metastasis to the brain" mean that cancer cells leave the primary lesion developed in other sites than brain, infiltrate into the brain, and grow in the brain, or the state that such infiltrated cancer cells have grown in the brain. Whether there is brain metastasis or not in a cancer patient having a primary lesion other than brain can be determined by a method of diagnostic imaging well known in the art. For example, when tumorigenesis in the brain is confirmed in images such as CT or MRI image for a cancer patient having a primary lesion other than brain to which a gadolinium contrast agent or the like has been administered, it can be determined that there is brain metastasis.

As used herein, the "healthy subject" means a human having no cancer development. The healthy subject herein is not necessary to have no disease other than cancer, but is preferably a healthy human having no disease even which is not cancer.

According to the present invention, miR-181c serves to open the BBB and promote brain metastasis in cancer patients. Accordingly, information about brain metastasis in a cancer patient can be obtained by measuring the miR-181c levels in the cancer patient. As used herein, the "miR-181c" is a human miRNA consisting of approximately 22 nucleotides (SEQ ID NO: 1) (Lim L P, et al. (2003) Science, 299: 1540; Landgraf P, et al. (2007) Cell, 129:1401-1414).

The miR-181c levels are measured by using a substance that specifically binds to miR-181c. As used herein, the "substance that specifically binds to miR-181c" is not particularly limited as long as it is a substance that can specifically bind to miR-181c. Since a nucleic acid usually bind specifically to a nucleic acid having its complementary sequence, a preferable substance that specifically binds to miR-181c is a nucleic acid that specifically binds to miR-181c.

The "nucleic acid that specifically binds to miR-181c" means a nucleic acid molecule that can specifically bind to miR-181c. Such a nucleic acid molecule usually has a complementary sequence to miR-181c. The "nucleic acid" as used herein comprises a DNA, an RNA, or an artificially generated nucleic acid (including bridged nucleic acids such as locked nucleic acids (2',4'-BNA)), or a combination thereof. For example, the nucleic acid that specifically binds to miR-181c includes, but is not limited to, a primer or a probe. The "primer" is usually a nucleic acid molecule of 10-30 mer (preferably, 17-25 mer, 15-20 mer, or the like) that is used for the amplification of nucleic acid and has, at least in a part (preferably, 7 mer or more, 8 mer or more, 9 mer or more, 10 mer or more, 11 mer or more, 12 mer or more, 13 mer or more, 14 mer or more, 15 mer or more, 20 mer or more, 25 mer or more, or 30 mer or more) thereof, a sequence complementary to a sequence located at an end of the sequence to be amplified. The "probe" is a nucleic acid molecule of 10-200 mer (preferably 10-100 mer, 10-50 mer, 10-30 mer, 10-20 mer, and the like) that has a sequence complementary to a target sequence, and can specifically bind to a target sequence, and has a complementary to a sequence, in at least a part (preferably, 7 mer or more, 8 mer or more, 9 mer or more, 10 mer or more, 11 mer or more, 12 mer or more, 13 mer or more, 14 mer or more, 15 mer or more, 20 mer or more, 25 mer or more, 30 mer or more, 50 mer or more, 100 mer or more) thereof. Methods for designing primers and probes for a target sequence are well known in the art. Preferably, the nucleic acid that specifically binds to miR-181c comprises at least partially an artificially designed sequence (for example, sequences for labeling and tagging).

As used herein, a substance "specifically binds" means that the substance binds to the target sequence or structure with a substantially higher affinity than binding to other nucleotide sequences or amino acid sequences or structures thereof. The "substantially higher affinity" means a sufficiently high affinity to allow the detection of the target sequence or structure with distinguishing from other sequences or structures in using a desired measuring apparatus or method. For example, the substantially higher affinity may mean that the molecules number of the (miR-181c specifically binding) substances that bind to miR-181c is 3 times or more, 4 times or more, 5 times or more, 6 times or more, 7 times or more, 8 times or more, 9 times or more, 10 times or more, 15 times or more, 20 times or more, 30 times or more, 50 times or more of the molecules number of the (miR-181c specifically binding) substances that bind to other sequences or structures. The binding constant (Ka) in the binding between the miR-181c specifically binding substance of the present invention and miR-181c may be, for example, at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$.

The "substance that specifically binds to miR-181c (miR-181c specifically binding substances)" (including the nucleic acid that specifically binds to miR-181c) herein may be labelled as needed. Examples of methods for labeling include the radioisotope (RI) labeling, fluorescent labeling, and enzymatic labeling. Examples of a radioisotope used in the RI labelling include 32P, 131I, 35S, 45Ca, 3H, and 14C. Examples of a fluorescent dye used in the fluorescent labeling include DAPI, SYTOX® Green, SYTO® 9, TO-PRO®-3, Propidium Iodide, Alexa Fluor® 350, Alexa Fluor® 647, Oregon Green®, Alexa Fluor® 405, Alexa Fluor® 680, Fluorescein (FITC), Alexa Fluor® 488, Alexa Fluor® 750, Cy® 3, Alexa Fluor® 532, Pacific Blue™, Pacific Orange™, Alexa Fluor® 546, Coumarin, Tetramethylrhodamine (TRITC), Alexa Fluor® 555, BODIPY® FL, Texas Red®, Alexa Fluor® 568, Pacific Green™, Cy® 5, and Alexa Fluor® 594. Available enzymatic labeling include biotin (biotin-16-dUTP, biotin-11-dUTP), digoxigenin (DIG: a steroid based natural product) (deoxyuridine 5'-triphosphate), and alkaline phosphatase.

According to the present invention, PDPK1 is one of the substances playing major roles in maintaining the structure of the BBB. Therefore, the BBB can be opened by suppressing the expression or inhibiting activity of PDPK1. Accordingly, a PDPK1 expression inhibitor or a PDPK1 activity inhibitor can be used as a DDS agent for an agent intended to be delivered into the brain. As used herein, "PDPK1" is an abbreviation of 3-phosphoinositide dependent protein kinase-1. PDPK1 is a serine/threonine kinase that phosphorylates and activates the AGC family of protein kinases. It is known that there are plural variants of the PDPK1 mRNA and protein. The nucleotide sequence of the mRNA of PDPK1 vulariant1, and the amino acid sequence of the PDPK1 vulariant1 protein are set forth in SEQ ID NO: 2 and SEQ ID NO: 3, respectively. The nucleotide sequence of the mRNA of PDPK1 vulariant2, and the amino acid sequence of the PDPK1 vulariant2 protein are set forth in SEQ ID NO: 4 and SEQ ID NO: 5, respectively. The nucleotide sequence of the mRNA of PDPK1 vulariant3, and the amino acid sequence of the PDPK1 vulariant3 protein is set forth in SEQ ID NO: 6 and SEQ ID NO: 7, respectively. The nucleotide sequence of the mRNA of PDPK1 vulariantX1, and the amino acid sequence of the PDPK1 vulariantX1 protein is set forth in SEQ ID NO: 8 and SEQ ID NO: 9, respectively. The PDPK1 herein may be any of these variants or one of their mutants that may occur in the body.

The present inventors have also found that, in cancer patients, miR-181c is contained in exosomes during traveling through the blood, and when the exosomes have reached the BBB, the exosomes are incorporated into the BBB constituting cells and open the blood-brain barrier. Accordingly, the inhibition of secretion of exosomes in cancer patients can prevent the opening of the blood-brain barrier and thereby can suppress brain metastasis. Thus, in one aspect, the present invention relates to suppression of brain metastasis using an exosome secretion inhibitor. As used herein, the "exosome secretion inhibitor" is not particularly limited as long as it is an agent that can inhibit the exosome secretion from cancer cells. It is known that neutral sphingomyelinase (hereinafter, referred to as the "nSMase2") (the cDNA sequence is set forth in SEQ ID NO: 10 and the amino acid sequence is set forth in SEQ ID NO: 11) and RAB27B (the cDNA sequence is set forth in SEQ ID NO: 12 and the amino acid sequence is set forth in SEQ ID NO: 13) are involved in the secretion of exosomes. Accordingly, the secretion of exosomes can be inhibited by suppressing the expression or inhibiting the activity of nSMase2 or RAB27B. Thus, an expression or activity inhibitor of nSMase2 or RAB27B can be used as an exosome secretion inhibitor in the present invention.

As used herein, the "expression inhibitor" of a gene, a protein, or an miRNA is not particularly limited, as long as it is an agent that suppresses the expression of the gene, protein, or miRNA. It is well-understood in the art that an expression inhibitor of a target gene can be obtained and used by designing and/or selecting, for example, an antisense to the gene sequence or to the mRNA sequence generated by transcription of the gene, dsRNA to the mRNA generated by the transcription of the gene, an aptamer to the mRNA generated by the transcription of the gene, or miRNA (including pri-miRNA and pre-miRNA) that can bind to a nucleotide sequence which is located upstream of a coding region and is essential for the expression of the gene.

It is well-understood in the art that an expression inhibitor of a target protein can be obtained or used by designing and/or selecting, for example, an antisense to a gene sequence encoding the protein or to an mRNA sequence generated by the transcription of the gene, dsRNA to an mRNA generated by the transcription of a gene encoding the protein, an aptamer to a gene sequence encoding the protein or to an mRNA generated by the transcription of the gene, or miRNA (including pri-miRNA and pre-miRNA) that can bind to a nucleotide sequence which is located upstream of a coding region and is essential for the expression of a gene encoding the protein.

It is well-understood in the art that an expression inhibitor of miRNA can be obtained or used by designing and/or selecting, for example, an antisense to a gene encoding the miRNA, pri-miR of the miRNA, or pre-miR of the miRNA; dsRNA to pri-miR of the miRNA or pre-miR of the miRNA; an aptamer to the pri-miR of the miRNA or pre-miR of the miRNA; or another miRNA (including pri-miRNA and pre-miRNA) that can bind to a nucleotide sequence which is located upstream of a coding region and is essential for the expression of a gene encoding the miRNA.

For example, the present inventors have found that expression inhibitors of PDPK1 include pri-miR-181c, pre-miR-181c, miR-181c and derivatives thereof.

As used herein, the derivatives of pri-miRNA, pre-miRNA and miRNA are molecules that have at least a seed sequence (the 7 nucleotides at positions 2 to 8 from the 5' end: ACUUACA) in the miRNA and that act to suppress the expression of the gene (or protein) of interest (PDPK1 in the case of miR-181c). The function of such a derivative is not necessarily quantitatively same as that of the original miRNA, but the derivative may have stronger or weaker activity than the original miRNA as long as it achieves an object of the present invention. Furthermore, the derivatives have a nucleotide sequence having an identity of about 70% or more and less than 100%, about 75% or more and less than 100%, about 80% or more and less than 100%, about 85% or more and less than 100%, about 90% or more and less than 100%, about 95% or more and less than 100% with the pri-miRNA, pre-miRNA and miRNA. The higher sequence identity means the more similarity in the structures between the pri-miRNA, pre-miRNA, or miRNA and the derivative thereof. The derivatives of the pri-miRNA, pre-miRNA, and miRNA may have a sequence that the original pri-miRNA, pre-miRNA, and miRNA do not have. Moreover, the nucleotide lengths of the derivative of pri-miRNA, pre-miRNA, and miRNA may be different from the original nucleotide length as long as they can exhibit the function of the miRNA and may be, for example, 10-50 mer, 15-30 mer, or 20-25 mer.

Moreover, the derivatives of the pri-miRNA, pre-miRNA, and miRNA include a nucleic acid molecule which has a seed sequence of the pri-miRNA, pre-miRNA and miRNA, and has one or more of addition, substitution, deletion, and modification selected from the following (i) to (iv) (at other than the seed sequence):

(i) addition of one or more (for example, 1-10, 1-5, 1-3, 1-2, or 1) nucleotide(s) to the wildtype sequence of pri-miR-181c, pre-miR-181c, or miR-181c;

(ii) substitution of one or more (for example, 1-10, 1-5, 1-3, 1-2, or 1) nucleotide(s) in the wildtype sequence of pri-miR-181c, pre-miR-181c, or miR-181c with other nucleotide(s);

(iii) deletion of one or more (for example, 1-10, 1-5, 1-3, 1-2, or 1) nucleotide(s) in the wildtype sequence of pri-miR-181c, pre-miR-181c, or miR-181c; and (iv) modification of one or more (for example, 1-10, 1-5, 1-3, 1-2, or 1) nucleotide(s) in the wildtype sequence of pri-miR-181c, pre-miR-181c, or miR-181c.

As used herein, the "activity inhibitor" of a protein or miRNA is not particularly limited as long as it is an agent that makes the protein or miRNA incapable of exhibiting its activity. For example, the activity inhibitor may be a substance that binds to the protein or miRNA, or a substance that binds to a substance to which the protein or miRNA binds. Known activity inhibitors of proteins are mimetics, antibodies or immunoreactive fragments thereof, aptamers, receptor derivatives, or antagonists. Known activity inhibitors of miRNA are mimetics, antisense DNA/RNA or dsRNA having a sequence complementary to at least a partial sequence of the miRNA, or aptamers to the miRNA.

As used herein, the "antisense" is a nucleic acid having a complementary sequence of the target sequence (for example, the sequence of pri-miR-181c, pre-miR-181c, or miR-181c or a DNA encoding pri-miR-181c) and may be DNA or RNA. The antisense is not required to be 100% complementary to the target sequence and may contain non-complementary nucleotides as long as it can specifically hybridize under stringent conditions (Sambrook et al., 1989, Molecular Cloning, A Laboratory Manual, Cold Spring Harbor Press, N.Y., and Ausubel et al. (eds.), 1995, Current Protocols in Molecular Biology, (John Wiley & Sons. N.Y.) at Unit 2.10). Once introduced into cells, the antisense binds to the target sequence and inhibits the transcription, the processing of RNA, the translation, or the stability thereof. The antisense includes antisense polynucleotides as well as polynucleotide mimetics and those that contain a modified back bone. Such an antisense can be designed and produced (for example, chemically synthesized) appropriately using a method well known in the art based on the target sequence information.

The "dsRNA" is RNA containing double strand RNA structure that has at least partially a sequence complementary to the target sequence. The dsRNA binds to mRNA having the target sequence, and thereby degrades the mRNA to suppress the translation (expression) of the target sequence by RNA interference (RNAi). The dsRNA includes siRNA (short interfering RNA) and shRNA (short hairpin RNA). The dsRNA is not required to have 100% identity with the target sequence as long as it can suppress the expression of the target gene. Moreover, a part of the dsRNA may be substituted with DNA for stabilization or another purpose. The siRNA is preferably double strand RNA having 21-23 nucleotide each. The siRNA can be obtained by a method well known in the art, for example, by chemical synthesis or as an analog of naturally occurring RNA. The shRNA is a RNA short chain having a hairpin turn structure. The shRNA can be obtained by a method well known in the art, for example, by chemical synthesis or introducing a gene encoding the shRNA into cells and expressing the gene.

The "aptamer" are nucleic acids that bind to a substance such as protein or nucleic acid. The aptamers may be constituted of RNA or DNA. The form of the nucleic acids may be a double strand or a single strand. The length of the aptamer is not particularly limited as long as it can specifically bind to the target molecule, but is for example, 10-200 nucleotides, preferably 10-100 nucleotides, more preferably 15-80 nucleotides, or further preferably 15-50 nucleotides. The aptamers can be selected using a method well known in the art and, for example, the SELEX (Systematic Evolution of Ligands by Exponential Enrichment) method (Tuerk, C. and Gold, L., 1990, Science, 249: 505-510).

As used herein, the "mimetics" are substances that have a structure similar to that of the protein or the miRNA. The mimetics can bind to the binding partners of the protein or the miRNA or can compete with the protein or miRNA, without exhibiting the activity of the protein or miRNA.

The "antibody" as used herein may be polyclonal antibody or monoclonal antibody and includes a non-human animal antibody, antibody having both of an amino acid sequence of a non-human animal antibody and an amino acid sequence of a human antibody (chimeric antibody and humanized antibody), and a human antibody. The immune globulin class of the antibodies may be any immune globulin class (isotype), IgG, IgM, IgA, IgE, IgD, or IgY, and, in the case of IgG, may be any subclass (IgG1, IgG2, IgG3, or IgG4). Furthermore, the antibody may be monospecific, bispecific (bispecific antibody), or trispecific (trispecific antibody) (for example, WO1991/003493). The immunoreactive fragments of an antibody mean proteins or peptides containing a part (partial fragment) of the antibody with maintaining the antibody's activity (immunoreactivity, binding activity) to the antigen. Examples of such immunoreactive fragment includes F(ab')$_2$, Fab', Fab, Fab$_3$, single strand Fv (hereinafter, referred to as the "scFv"), (tandem) bispecific single strand Fv (sc(Fv)$_2$), single strand triple bodies, nanobodies, divalent V$_H$Hs, pentavalent V$_H$Hs, minibodies, (double strand) diabodies, tandem diabodies, bispecific tribodies, bispecific bibodies, dual affinity retargeting molecules (DART), triabodies (or tribodies), tetrabodies (or [sc(Fv)$_2$]$_2$) or (scFv-SA)$_4$), disulfide linked Fv (hereinafter, referred to as "dsFv"), compact IgGs, heavy chain antibodies or polymers thereof (see Nature Biotechnology, 29 (1): 5-6 (2011); Maneesh Jain et al., TRENDS in Biotechnology, 25 (7) (2007): 307-316; and Christoph stein et al., Antibodies (1): 88-123 (2012)). As used herein, the immunoreactive fragments may be any of monopecific, bispecific, trispecific, and multispecific antibodies. The aptamers are nucleic acid molecules capable of binding to a specific nucleic acid or protein. The receptor derivative means a substance having a binding region structure of a receptor to which the protein of interest binds. The receptor derivative includes a conjugate of the constant region of an antibody with a receptor and a membrane protein receptor solubilized by deleting the transmembrane region. The antagonist includes a wide range of substances that competes with the protein or miRNA of interest and inhibits the function thereof.

Herein, when the activity inhibitor binds to the protein or miRNA or when the activity inhibitor binds to a substance to which the protein or miRNA binds to, the binding is preferably specific and the binding constant (Ka) thereof may be for example, at least $10^7$ M$^{-1}$, at least $10^8$ M$^{-1}$, at least $10^9$ M$^{-1}$, at least $10^{10}$ M$^{-1}$, at least $10^{11}$ M$^{-1}$, at least $10^{12}$ M$^{-1}$, or at least $10^{13}$ M$^{-1}$.

As used herein, the "agent" is a substance mainly used as an active ingredient, and includes a small molecule, a nucleic acid molecule (DNA and/or RNA), a protein, and a fusion thereof. As used herein, the "composition" comprises at least an agent that serves as an active ingredient and optionally comprises water, a solvent, and other additives as needed. The composition herein may comprise only one substance or 2 or more substances as an active ingredient(s). As used herein, the "active ingredient" is not particularly limited, as long as it can exhibit a desired biological activity, and includes a substance capable of exhibiting a therapeutic effect or preventive effect as well as a substance exhibiting a function as DDS. Whether a substance is an active ingredient or not can be determined not only depending on whether the substance has a biological action or not, but also depending on whether the amount of the substance contained in the composition can allow the substance to exhibit the biological action.

The "composition for diagnosis or risk assessment of brain metastasis" is a composition to be used in a method for diagnosing brain metastasis or a method for assessing risk of brain metastasis as described below, and includes a diagnostic composition (including an extracorporeal diagnostic composition). The composition for diagnosis or risk assessment of brain metastasis may be used for in vivo, ex vivo, or in vitro diagnosis, but preferably is for ex vivo or in vitro use. Compositions for in vivo diagnosis or risk assessment may be formulated to be administered to a patient in accordance with the formulation of pharmaceutical compositions as described below. Examples of the composition for diagnosis or risk assessment herein include an X-ray contrast agent, a reagent for general examination, a reagent for blood test, a reagent for biochemical test, a reagent for immunoserologic examination, an agent for bacteriological examination, and a reagent for functional examination. Since the composition for diagnosis or risk assessment herein needs to determine miR-181c level in a sample, the composition comprises the substance that specifically binds to miR-181c described above.

In another aspect, the composition for diagnosis or risk assessment herein may be provided as a kit for diagnosis or risk assessment comprising the composition as an active ingredient. The kit can be constituted by any materials as long as miRNA levels can be determined. For example, the kit for diagnosis or risk assessment herein may be a kit comprising a primer that can bind to miR-181c (a kit for measuring miRNA levels by using gene amplification technique such as PCR) or a kit comprising a probe that can bind to miR-181c (a kit for measuring miRNA levels by using a nucleic acid binding detection technique such as hybridization).

Alternatively, the kit for diagnosis or risk assessment herein may be a kit which determines the miRNA level utilizing an expression inhibitory effect of miRNA as indicator. In this case, the kit may comprise, for example, a nucleic acid encoding a label (luciferase, or the like) having an mRNA 3'UTR that can specifically bind to miR-181c (a kit for measuring miRNA levels by detecting the expression of the label in the reporter assay or the like).

As used herein, the "pharmaceutical composition" is a composition to be used for treatment or prevention and comprises a therapeutic or preventive agent. The pharmaceutical composition is preferably prepared into a unit dosage form comprising a suitable dose of the active ingredient. Moreover, any oral or parenteral formulation may be employed as long as it can be administered to a patient. Examples of compositions for parenteral administration include injections, nasal drops, suppositories, patches, ointments, and the like, and are preferably injections. Examples of the dosage form of the pharmaceutical composition of the present invention include solutions or lyophilized formulations. When the pharmaceutical composition of the present invention is used as an injection, an excipient (see "Japanese Pharmaceutical Excipients Directory" Yakuji Nippo Limited; "Handbook of Pharmaceutical Excipients Fifth Edition" APhA Publications) including a solubilizing agent such as propylene glycol or ethylenediamine, a buffer such as phosphate, an isotonizing agent such as sodium chloride or glycerin, a stabilizer such as sulfite, a preservative such as phenol, or a soothing agent such as lidocaine may be added as needed. Moreover, when the pharmaceutical composition of the present invention is used as an injection, a storage container therefor may be an ampoule, a vial, a prefilled syringe, a cartridge for pen type syringes, a bag for infusion, and the like. For example, the pharmaceutical composition may usually contain 5-500 mg, 5-100 mg, 10-250 mg of the active ingredient per unit dosage form.

As used herein, the pharmaceutical composition for suppressing brain metastasis may comprise one or more agents selected from an miR-181c expression inhibitor, an miR-181c activity inhibitor, and an exosome secretion inhibitor as an active ingredient. Moreover, the pharmaceutical composition for suppressing brain metastasis may comprise one or more agents selected from an miR-181c expression inhibitor, an miR-181c activity inhibitor, and an exosome secretion inhibitor as active ingredient(s), or further comprise other agent(s) to be used in combination as active ingredient(s). Examples of such other agents include other cancer metastasis inhibitors and anticancer agents.

Examples of the other cancer metastasis inhibitors or anticancer agents that can be included in the pharmaceutical composition for suppressing brain metastasis include alkylating agents including nitrogen mustards such as cyclophosphamide, ifosfamide, melphalan, busulfan, and thiotepa, and nitrosoureas such as nimustine, ranimustine, Dacarbazine, procarbazine, temozolomide, carmustine, Streptozotocin, bendamustine; platinum compounds such as cisplatin, carboplatin, oxaliplatin, and nedaplatin; antimetabolites such as enocitabine, capecitabine, carmofur, cladribine, gemcitabine, cytarabine, cytarabine ocfosphate, tegafur, tegafur/uracil, tegafur/gimeracil/oteracil potassium, doxifluridine, nelarabine, hydroxycarbamide, 5-fluorouracil (5-FU), fludarabine, pemetrexed, pentostatin, mercaptopurine, and methotrexate; plant alkaloids or microtubule inhibitors such as irinotecan, etoposide, eribulin, sobuzoxane, docetaxel, nogitecan, paclitaxel, vinorelbine, vincristine, vindesine, and vinblastine: antitumor antibiotics such as actinomycin D, aclarubicin, amrubicin, idarubicin, epirubicin, zinostatin stimalamer, daunorubicin, doxorubicin, pirarubicin, bleomycin, peplomycin, mitomycin C, mitoxantrone, and liposomal doxorubicin; cancer vaccines such as Sipuleucel-T; molecular target drugs such as ibritumomab tiuxetan, imatinib, everolimus, erlotinib, gefitinib, gemtuzumab ozogamicin, sunitinib, cetuximab, sorafenib, dasatinib, tamibarotene, trastuzumab, tretinoin, panitumumab, bevacizumab, bortezomib, lapatinib, and rituximab; hormone preparations such as anastrozole, exemestane, estramustine, ethinyl estradiol, chlormadinone, goserelin, tamoxifen, dexamethasone, toremifene, bicalutamide, flutamide, predonisolone, fosfestrol, mitotane, methyltestosterone, medroxyprogesterone, mepitiostane, leuprorelin, and letrozole; biological response modifiers such as interferon α, interferon β, interferon γ, interleukin, ubenimex, freeze-dried BCG, and lentinan.

As used herein, the pharmaceutical composition for increasing permeability of the blood-brain barrier may comprise one or more PDPK1 expression inhibitors or PDPK1 activity inhibitors as an active ingredient(s). The pharmaceutical composition for increasing permeability of the blood-brain barrier may solely comprise the PDPK1 expression inhibitor and/or PDPK1 activity inhibitor as active ingredient(s), or may further comprise another agent to be used in combination as an active ingredient. Examples of such another agent include drugs that act on and increase the permeability of the blood-brain barrier as well as agents intended to be delivered to the brain. Herein, when the pharmaceutical composition for increasing permeability of the blood-brain barrier is used particularly for delivering a desired agent to the brain, such a pharmaceutical composition is referred to as the "agent-delivery composition". In the agent-delivery composition herein, the "agent intended to be delivered to the brain" may be referred to as the "medicinal component" to be distinguished from the agent (PDPK1 expression inhibitor or PDPK1 activity inhibitor) intended to open the BBB.

As used herein, the "agent-delivery composition" comprises at least a PDPK1 expression inhibitor or activity inhibitor as an active ingredient. The agent-delivery composition is preferably prepared into a unit dosage form comprising a suitable dose of the medicinal component. An example of such a unit dosage form is an injection (ampoule, vial, prefilled syringe). Usually 5-500 mg, 5-100 mg, or 10-250 mg of the PDPK1 expression inhibitor or activity inhibitor may be contained per unit dosage form.

Moreover, the agent-delivery composition may comprise, in addition to the PDPK1 expression inhibitor or activity inhibitor, an agent intended to be delivered to the brain, a medicinal component. The PDPK1 expression inhibitor or activity inhibitor and the medicinal component may be contained in one formulation or provided as separate formulations to be used in combination.

As used herein, the "medicinal component" is a medicine intended to be delivered into the brain, and includes, for example, a therapeutic or preventive agent for a target disease such as neurosurgical diseases such as cerebrovascular disorders (such as cerebral infarction/cerebral hemorrhage/cerebral aneurysm), brain tumor (such as meningioma, pituitary adenoma, including brain metastasis), infectious diseases (such as meningitis), functional brain diseases (such as trigeminal neuralgia), the spinal cord disease (such as disc herniation, spinal stenosis); neurological diseases such as Parkinson's disease, spinocerebellar degeneration, and epilepsy; and mental diseases such as Alzheimer's disease, non-Alzheimer type degenerative dementia, insomnia, and depression. For example, when the target disease is brain tumor, the anticancer agents described above may be used and, particularly when it is glioma, Avastin or Gliadel may be preferably used.

In another aspect, the agent-delivery composition herein may be provided as a kit for treatment or prevention, comprising the composition as an active ingredient. The constitution of the kit is not limited as long as it comprises the PDPK1 expression inhibitor or activity inhibitor, and the kit may comprise, for example, the PDPK1 expression inhibitor or activity inhibitor and the medicinal component. In this case, the PDPK1 expression inhibitor or activity inhibitor and the medicinal component may be provided in a form to be administered simultaneously or separately.

Throughout the description, the "level" means a numerical value indicating the quantity of miR-181c, which includes, for example, the concentration, the amount, or any alternative numerically value indicating the quantity to be used instead thereof. Accordingly, the level may be a measurement itself of such as fluorescence or may be a value converted into the concentration or the amount. The level may be absolute numerical value (abundance, abundance per unit area) or a numerical value relative to a control provided as needed. The level may be the mean or median when the same sample is measured plural times (at the same time or at different times).

As used herein, the "kit" may comprise, in addition to the active ingredient, a package storing components of the kit, such as a paper box or a plastic case, an ampoule, a vial, a tube, a syringe, or the like storing each component, an instruction manual, and the like.

In another aspect, the present invention involves an apparatus for judging brain metastasis in a cancer patient, an apparatus for assessing risk of brain metastasis in a cancer patient, and a computer program used in these apparatuses (FIG. 23). These apparatuses provide information for diagnosis to a person (usually a doctor) who diagnoses whether there is brain metastasis or not. The apparatus for judging brain metastasis of the present invention comprises miR-181c-measuring means. The "miR-181c-measuring means" is an apparatus that conducts the measurement of a polynucleotide having the nucleotide sequence of miR-181c (SEQ ID NO: 1) in a sample derived from a subject, which processes the sample from the subject cancer patient as prescribed to convert information about the miR-181c levels in the sample into digits or electrical signals. The miR-181c-measuring means allows to contact the agent for diagnosis or risk assessment of brain metastasis described above and the sample from the subject cancer patient and to react them if necessary, and measures generated parameters such as a strength of a light (fluorescence, luminescence) which reflects the miR-181c levels. The contact between the agent for diagnosis or risk assessment of brain metastasis and the sample from the subject cancer patient usually takes place in a container (reaction vessel) such as a plate or a tube.

The computer program of the present invention includes a computer program that can make an existing apparatus to be used for judging brain metastasis or for assessing risk of brain metastasis in a cancer patient by installing, even if the existing apparatus is widely used and can be used for other measurement or judgment. The computer program of the present invention is not required to be installed in the apparatus for judging brain metastasis and the apparatus for assessing risk of brain metastasis. The computer program of the present invention may be provided, for example, in such a form to be stored on a recording medium. The "recording medium" is a medium that can carry a program without occupying space, and includes a flexible disk, a hard disk, CD-R, CD-RW, MO (magneto-optical disk), DVD-R, DVD-RW, a flash memory, and the like. Moreover, the computer program of the present invention can be transmitted from the computer program storing computer to other computers or other apparatuses through a communication line. The computer program of the present invention includes those stored on such a computer and being transmitted.

Advantageous Effects of Invention miR-181c contributes to brain metastasis by destructing the BBB. Since expression of miR-181c is specifically increased in cancer patients with brain metastasis, miR-181c can be used as indicator for diagnosis or risk assessment of brain metastasis. A brain metastasis can be suppressed by inhibiting the expression or activity of miR-181c or inhibiting secretion of EVs (containing miR-181c). PDPK1 expression inhibitors and PDPK1 activity inhibitors including miR-181c increases the permeability of the BBB, and thus can be used as DDS of agents desired to be delivered into the brain.

BRIEF DESCRIPTION OF DRAWINGS

FIG. 1a illustrates the protocol for in vivo-selection of brain metastatic derivatives. (b) The left photograph shows bioluminescence imaging of a mouse with BMD2a cell brain metastasis; and the right photographs shows bioluminescence imaging of a mouse brain with cancer cell metastasis. (c) Photographs of hematoxylin and eosin (HE)-stained sections from a mouse brain cerebral cortex and midbrain. The upper panels show cerebral cortex and the lower panels show the midbrain. The left panels (Normal) show sections from a mouse without cancer cell metastasis, and the middle panels (Metastasis) show sections from a mouse with cancer cell metastasis. The arrowheads indicate metastatic cancer cells. The right photographs are higher magnification photographs. The bar at the lower right corner in each photograph indicates 100 μm.

FIG. 2a illustrates in vitro blood-brain barrier model constructed from primary culture cells of monkey brain capillary endothelial cells, pericytes, and astrocytes. (b) Representative photographs of endothelial cells, pericytes, and astrocytes. The astrocytes were visualized using a fluorescence microscope. The bar at the lower right corner in each photograph indicates 100 μm. (c) Photographs of the results of immunofluorescence staining of tight junction proteins (Claudin-5, Occludin, and ZO-1) and the N-cadherin. The bar at the lower right corner in each photograph indicates 20 μm. (d) A graph of the change of TEER after thawing until the start of the experiment. The value of TEER increased to a maximum of 869.55 $\Omega \times cm^2$ after thawing the BBB in vitro model. The error bars represent standard deviation (SD).

FIG. 4a illustrates the invasive test of PKH-67 labeled cancer cells using the in vitro BBB model. (b) The left panel is a graph showing the ratio (folds) of the number of D3H2LN, BMD2a, and BMD2b cells that migrated across the in vitro BBB model relative to the number of D3H1 cells that migrated across the BBB model. The error bars represent standard deviation (SD), and * indicates P<0.01 and ** indicates P<0.01. The right panel is photographs of D3H1, D3H2LN, BMD2a, and BMD2b cells that migrated across the in vitro BBB model.

DESCRIPTION OF EMBODIMENTS

Figure 1:
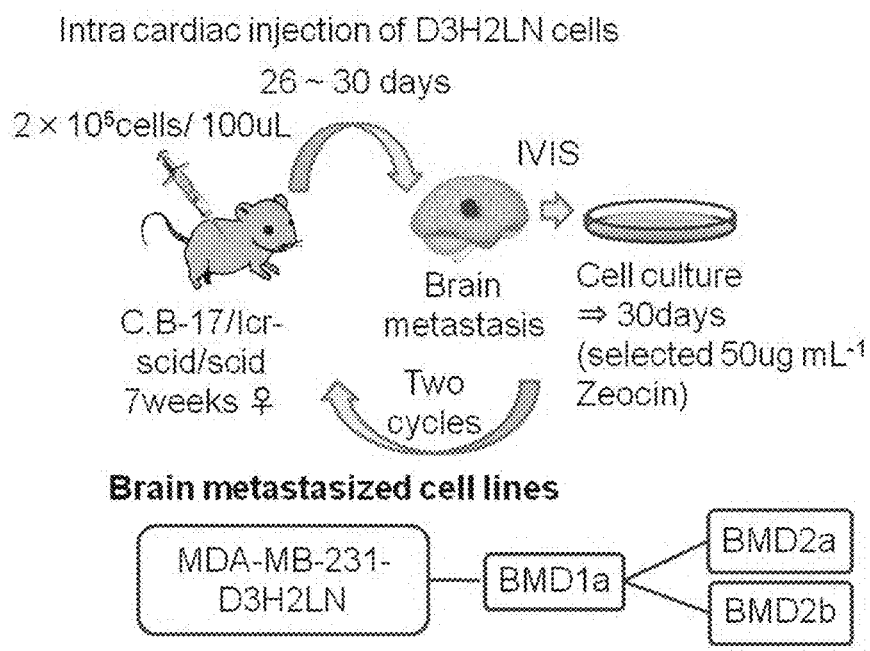
FIG. 1 (a)
Figure 1:
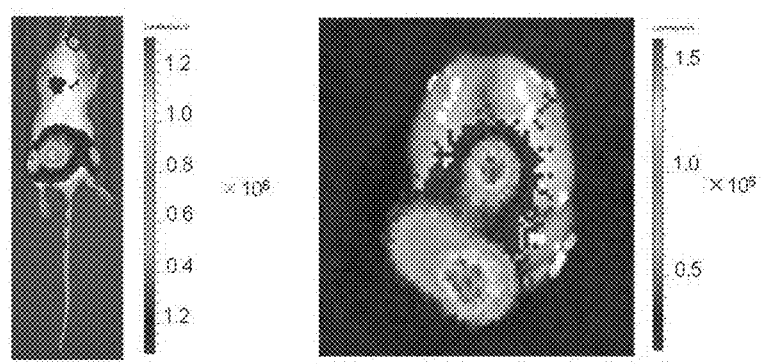
Figure 1:
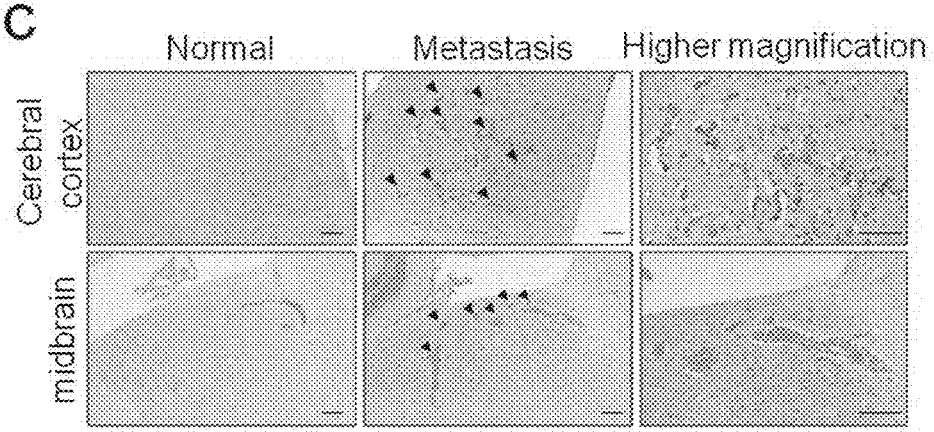

1. Method for Diagnosis or Risk Assessment of Brain Metastasis in Cancer Patient In one aspect, the present invention relates to a method for diagnosing brain metastasis or a method for assessing risk of brain metastasis, comprising measuring an miR-181c level in a sample from a subject cancer patient. In one aspect, the present invention relates to a method for diagnosing brain metastasis in a subject cancer patient (or a method for assessing risk of brain metastasis), comprising: determining an miR-181c level in a sample from the subject cancer patient, and judging the presence or absence of brain metastasis (or assessing risk of brain metastasis) in the subject cancer patient from the determined miR-181c level, wherein the subject cancer patient is judged to have metastasis to brain (or assessed to have a high risk of brain metastasis) when the miR-181c level in the sample from the subject cancer patient is higher than the miR-181c level in a sample from a negative control.

Alternatively, in one aspect, the present invention relates to a method for providing information for diagnosing brain metastasis, comprising measuring an miR-181c level in a sample from a subject cancer patient. The present invention relates to a method for providing information for diagnosing brain metastasis (or for assessing risk of brain metastasis) in a subject cancer patient, comprising: a step of determining an miR-181c level in a sample from the subject cancer patient, and a step comprising providing information for judging the presence or absence of brain metastasis (or assessing a risk of brain metastasis) in the subject cancer patient from the determined miR-181c level, wherein information that the subject cancer patient has brain metastasis (or has a high risk of brain metastasis) is provided when the miR-181c level in the sample from the subject cancer patient is higher than the miR-181c level in a sample from a negative control.

The step of determining an miR-181c level is conducted by measuring a polynucleotide having the nucleotide sequence of miR-181c (SEQ ID NO: 1) in the sample from the subject. The polynucleotide may be measured by a method utilizing detection of nucleic acid binding such as hybridization; a method utilizing amplification of nucleic acids such as PCR; a method utilizing the expression inhibitory activity of miR-181c such as a reporter assay; or decoding the sequence of miRNA or cDNA transcribed from miRNA.

Examples of the method utilizing hybridization include Southern hybridization, Northern hybridization, dot hybridization, fluorescence in situ hybridization (FISH), microarray, and the ASO method.

For example, the "step of determining an miR-181c level" in the present invention may comprise the following steps:
(a) a step of contacting a sample from a subject cancer patient with at least one nucleic acid construct (probe) that binds to the nucleotide sequence of miR-181c (SEQ ID NO: 1);
(b) a step of measuring the binding between the probe and miR-181c in the sample; and
(c) a step of determining the miR-181c level in the sample from the measured binding between the probe and miR-181c.

In the description above, the "binding between the probe and miR-181c" to be measured may be a bound amount, the number of binding, or a percentage of the bound substances. The step of determining the miR-181c level in the sample from the measured binding between the probe and miR-181c may be conducted, for example, by the following procedures. Binding between the probe and miR-181c in a standard sample which is a serial dilution series of miR-181c is measured to generate a standard curve. The miR-181c level in a sample from a subject cancer patient can be calculated by comparing a measurement of the binding between the probe and miR-181c measured in the sample from the subject cancer patient with the standard curve. The standard curve may be determined by measuring standard samples simultaneously with the sample from the subject cancer patient, or alternatively by measuring standard samples separately from (at different time from) the samples from the subject cancer patient. Accordingly, the standard curve may be pre-obtained from the measurements of standard samples which is measured before the measurement of a sample from a subject cancer patient. Instead of directly binding the miRNA with the probe, cDNA may be synthesized from miRNA in a sample from a patient, and the binding of the synthesized cDNA and probe may be measured.

Examples of the method utilizing PCR include ARMS (amplification refractory mutation system), RT-PCR (reverse transcriptase-PCR), and nested PCR.

For example, the determination of a miR-181c level in the present invention may comprise the following steps:
(a) a step of amplifying a nucleic acid molecule having miR-181c (SEQ ID NO: 1) in a sample from a subject cancer patient by using at least one nucleic acid construct (primer) that binds to the nucleotide sequence of miR-181c (SEQ ID NO: 1);
(b) a step of measuring the amount of the amplified nucleic acid molecule; and
(c) a step of determining the miR-181c level in the sample from the measured amount of the amplified nucleic acid.

The above step of determining the miR-181c level in the sample from the measured amount of the amplified nucleic acid may be conducted, for example, by the following procedures. As standard samples, predetermined copy number of nucleic acids are used to obtain the amplified amount, from which a standard curve is generated. The miR-181c level in a sample from a subject cancer patient can be calculated by comparing the measurement of the amplified nucleic acid in the sample from the subject cancer patient with the standard curve. The standard curve may be determined by measuring standard samples simultaneously with the sample from the subject cancer patient, or alternatively by measuring standard samples separately from (at different time from) the sample from the subject cancer patient. The standard curve may be pre-obtained by measuring standard samples before the measurement of a sample from a subject cancer patient. Instead of directly amplifying the miRNA, cDNA may be synthesized using miRNA obtained from a patient sample, which can be used for amplification.

As a method for determining the level of miRNA utilizing the expression inhibitory function of miR-181c, a method involving a marker gene of a fluorescence protein (such as luciferase) or the like is widely known. For example, the miR-181c level can be determined by designing a marker gene which generates mRNA having a 3'UTR sequence (for example, SEQ ID NO: 14 or SEQ ID NO: 15) that can bind to the seed sequence (ACUUACA) of miR-181c, and treating the gene transformed cells with a sample under the conditions that allow the expression of the gene.

For example, the determination of a miR-181c level in the present invention may comprise the following steps:
(a) a step of contacting a sample from a subject cancer patient with cells transformed with a polynucleotide encoding the following (i) and (ii):
(i) a marker gene,
(ii) a 3'UTR sequence that binds to the seed sequence (ACUUACA) of miR-181c in mRNA;
(b) a step of expressing the polynucleotide in the cells; and
(c) a step of determining the miR-181c level in the sample from the amount of the expressed marker gene product.

In the above method, the step of determining the miR-181c level in the sample from the amount of the expressed marker gene product can be conducted by, for example, generating a standard curve from the measurements of standard samples which contain the predetermined amount of the marker gene product, and calculating the miR-181c level by applying the measurements for the amount of the marker gene product to the standard curve.

When the sequence of miRNA or cDNA is decoded, the level of miR-181c can be determined by synthesizing cDNA from the RNA as needed, decoding the sequence of synthesized cDNA with a sequencer, and determining the level of miR-181c from the amount of the decoded miR-181c.

When cDNA is synthesized from miRNA in the description above, it may be conducted with a cDNA synthesis kit (RNA-Quant cDNA Synthesis Kit, System Biosciences, LLC, San Francisco, USA) or the like.

The "step of judging or assessing" and the "step comprising providing information for judging or assessing" (collectively, referred to as the "judging step" in this paragraph) in the method for diagnosis of the present invention and the like can be conducted using the determined miR-181c level. The judging step can be conducted by comparing the determined miR-181c level of the subject with the miR-181c level of a negative control. When the miR-181c level in the sample from the subject is higher than the miR-181c level in the sample from the negative control, the miR-181c level is determined to be high and the subject can be judged possibly to have brain metastasis (or assessed possibly to have a high risk of brain metastasis). When the miR-181c level in the sample from the subject is not higher than (that is, equal to or lower than) the miR-181c level in the sample from the negative control, the miR-181c level is determined not high and the subject can be judged possibly not to have brain metastasis (or assessed possibly to have a low risk of brain metastasis).

As used herein, the "negative control" means healthy subjects or cancer patients having no brain metastasis (for example, Stage 1 and/or Stage 2 cancer patients and/or Stage 3 and/or Stage 4 cancer patients having no brain metastasis). The "miR-181c level of the negative control" can be obtained by measuring the miR-181c level in such a negative control according to the method described above. Alternatively, when there is predetermined information about the miR-181c level already measured for such a negative control, such a level can be used as the miR-181c level of the "negative control". Moreover, a standard comparative sample containing the same amount of miR-181c as the miR-181c level of the "negative control" may be measured simultaneously with the sample from the subject cancer patient.

Throughout the description, whether the miR-181c level in a subject sample is higher than the miR-181c level in a sample to be compared or not can be determined by a statistical analysis. The statistical significance can be determined by comparing 2 or more samples and determining a confidence interval and/or a p value (Dowdy and Wearden, Statistics for Research, John Wiely & Sons, NewYork, 1983). The confidence interval of the present invention may be, for example, 90%, 95%, 98%, 99%, 99.5%, 99.9%, or 99.99%. Moreover, the p value of the present invention may be, for example, 0.1, 0.05, 0.025, 0.02, 0.01, 0.005, 0.001, 0.0005, 0.0002, or 0.0001.

Throughout the description, the "method for diagnosis" and the "method for assessing risk" comprises a method for monitoring the state or change of brain metastasis or a method for monitoring the risk of brain metastasis unless such interpretation is inconsistent. Accordingly, the word of "diagnosis" or "risk assessment", as used herein, may be interpreted as monitoring the state or change of brain metastasis or the risk of brain metastasis unless such interpretation in particular is inconsistent. Moreover, when the method for diagnosis or the method for risk assessment herein means monitoring, the diagnosis or risk assessment may be conducted continually or intermittently. Moreover, the method for diagnosis and the method for assessing risk of the present invention may be conducted in vivo, ex vivo, or in vitro, but preferably conducted ex vivo or in vitro.

As used herein, the "sample" may be selected depending on the purpose of use as appropriate. For example, the sample may be a cell culture supernatant, a cell lysate, a tissue specimen collected from a subject as biopsy, or a liquid collected from a subject. Examples of the sample include tissue, blood, plasma, serum, lymph fluid, urine, stool, serosity, spinal fluid, cerebrospinal fluid, synovial fluid, aqueous humor, lacrimal fluid, saliva, or a fraction or processed product thereof. The sample is preferably blood, plasma, serum, or lymph fluid.

The risk assessment of brain metastasis means a method for predicting the progress or outcome of the condition of a patient thereby and does not mean that the progress or outcome of the condition can be predicted at 100% of accuracy. The result of assessment of risk of brain metastasis indicates whether the risk of a certain progress or outcome is increased or not, but does not indicates that the certain progress or outcome is more likely to occur as compared with that the certain progress or outcome is not occurring. Thus, the assessment of risk of brain metastasis indicates that the progress or outcome of brain metastasis is more likely to occur in patients with increased the miR-181c level compared to patients exhibiting no such characteristics.

In the method for diagnosis and the method for risk assessment herein, the "subject cancer patient" is not particularly limited as long as the patient is the cancer patient as described above. The subject cancer patient in the method for diagnosis of brain metastasis is preferably a Stage IV cancer patient, a patient with metastasis to distant organs, or a patient with infiltration of cancer cells into the blood, since brain metastasis occurs mainly on late stages of cancer as described above. On the other hand, the subject in the method for assessing risk of brain metastasis is preferably a Stage I to III patient in which the risk of brain metastasis is high but metastasis itself is not yet likely to occur, a patient with no metastasis to distant organs, or a patient with no infiltration of cancer cells into the blood. Moreover, the subject cancer patient is preferably a breast cancer patient.

2. Method for Treatment or Prevention of Brain Metastasis in Cancer Patient

According to the mechanism of cancer metastasis found by the present inventors, miR-181c contained in EVs (including exosomes) secreted by cancer cells contributes to brain metastasis. Therefore, in another aspect, the present invention relates to a method for treating or preventing brain metastasis in a cancer patient, comprising inhibiting the expression or activity of miR-181c in the cancer patient. In this method, the inhibition of the expression or activity of miR-181c may be conducted by administering an miR-181c expression inhibitor or activity inhibitor to a patient in need thereof. Accordingly, in a certain embodiment, the present invention relates to a method for treating or preventing brain metastasis in a cancer patient, comprising administering an miR-181c expression inhibitor or activity inhibitor to the cancer patient.

Alternatively, the inhibition of the expression or activity of miR-181c can be accomplished indirectly by inhibiting the secretion of EVs containing miR-181c. Accordingly, in one aspect, the present invention relates to a method for treating or preventing brain metastasis in a cancer patient, comprising inhibiting secretion of EVs containing miR-181c in the cancer patient. The inhibition of secretion of EVs can be accomplished, for example, by inhibiting the expression or activity of protein (nSMase2 and RAB27B) essential for the secretion of EVs. Accordingly, in another aspect, the present invention relates to a method for treating or preventing brain metastasis in a cancer patient, comprising administering an exosome secretion inhibitor to the cancer patient. In a specific aspect, the present invention relates to a method for treating or preventing brain metastasis in a cancer patient, comprising administering an nSMase2 expression or activity inhibitor and/or an RAB27B expression or activity inhibitor to the cancer patient.

The administration of the pharmaceutical composition (therapeutic or preventive agent for brain metastasis) may be local or systemic. The mode of administration is not particularly limited and is parenteral or oral administration as described above. Examples of parenteral route of administration include subcutaneous, intraperitoneal, in blood (intravenous or intraarterial), injection or infusion into spinal fluid, or the like and a preferable route is administration into blood. Moreover, the pharmaceutical composition (therapeutic or preventive agent) may be administered at once or administered continuously or intermittently. For example, the administration may be a continuous administration for 1 minute to 2 weeks.

The dose of the pharmaceutical composition (therapeutic or preventive agent for brain metastasis) is not particularly limited as long as it can exert desired therapeutic effect or preventive effect, and may be determined depending on the stage of the cancer, the presence or absence of brain metastasis, symptoms, sex, age, or the like as appropriate. The dose of the pharmaceutical composition according to the present invention may be determined, for example, by referring a therapeutic effect or preventive effect on brain metastasis as indicator. For example, the pharmaceutical composition may be administered by intravenous injection at a dose of the active ingredient of usually about 0.01-20 mg/kg body weight, preferably about 0.1-10 mg/kg of body weight, further preferably about 0.1-5 mg/kg of body weight as one dose, at about 1-10 times a month, preferably about 1-5 times a month. An amount referring the above may be administered when administered parenterally via another route or orally. When symptoms are particularly severe, the dose or frequency of administration may be increased according to the symptoms.

3. Method for Increasing Permeability of Blood-Brain Barrier and Method for Delivering Desired Active Ingredient Across Blood-Brain Barrier into Brain The present inventors have found that the permeability of the blood-brain barrier is improved by decreasing the expression or activity of PDPK1. Accordingly, in another aspect, the present invention relates to a method for increasing permeability of blood-brain barrier, comprising inhibiting expression or activity of PDPK1 in vascular endothelial cells. In a further aspect, the present invention relates to a method for delivering a desired medicinal component across blood-brain barrier into brain, comprising administering the medicinal component with a PDPK1 expression inhibitor or activity inhibitor.

For example, the method for increasing permeability of blood-brain barrier of the present invention comprises the following method: a method for increasing permeability of blood-brain barrier in a patient, comprising suppressing the expression or inhibiting the activity of PDPK1 in brain microvascular endothelial cells (BMECs) in the patient. The suppression of the expression or inhibition of the activity of PDPK1 can be accomplished by administering a PDPK1 expression inhibitor or activity inhibitor. Accordingly, in another aspect, the present invention relates to a method for increasing the permeability of the blood-brain barrier in a patient, comprising administering a PDPK1 expression inhibitor or activity inhibitor.

The method for delivering desired medicinal component across blood-brain barrier into brain comprises the following method: a method for delivering a desired medicinal component across the blood-brain barrier of a patient into the brain, comprising suppressing the expression or inhibiting the activity of PDPK1 in brain microvascular endothelial cells (BMECs) in the patient, and administering the desired medicinal component to the patient. In this method, the inhibition of expression or activity of PDPK1 may be conducted by administering a PDPK1 expression inhibitor or activity inhibitor to a patient in need thereof. For example, the inhibition of expression of PDPK1 can be accomplished by administering miR-181c or EVs containing miR-181c. Accordingly, in another aspect, the present invention relates to a method for delivering a desired medicinal component across the blood-brain barrier of a patient into the brain, comprising administering the desired medicinal component and a PDPK1 expression inhibitor or activity inhibitor. Alternatively, the present invention may be a method for delivering a desired medicinal component across the blood-brain barrier of a patient into the brain, comprising increasing the permeability of the blood-brain barrier of the patient by administering a PDPK1 expression inhibitor or activity inhibitor to the patient; and administering the desired medicinal component to the blood-brain barrier permeability increased patient to deliver the medicinal component across the blood-brain barrier into the brain. The desired medicinal component may be administered simultaneously with the PDPK1 expression inhibitor or activity inhibitor or administered separately (for example, before or after the administration of the PDPK1 expression inhibitor or activity inhibitor).

The administration of the PDPK1 expression inhibitor or activity inhibitor or the agent-delivery composition of the present invention may be local or systemic. The route of administration is not particularly limited and can be parenteral or oral administration as described above. Examples of parenteral route of administration include subcutaneous, intraperitoneal, in blood (intravenous or intraarterial), injection or infusion into spinal fluid, or the like and a preferable route is administration into blood. Moreover, the PDPK1 expression inhibitor or activity inhibitor or the agent-delivery composition may be administered temporarily or administered continuously or intermittently. For example, the administration may be a continuous administration for 1 minute to 2 weeks. Moreover, the PDPK1 expression inhibitor or activity inhibitor or the agent-delivery composition may be administered simultaneously with or separately from the medicinal component, and preferably administered before the administration of the medicinal component or simultaneously with the medicinal component.

The dose of the PDPK1 expression inhibitor or activity inhibitor or the agent-delivery composition is not particularly limited as long as it is a dose at which a desired permeability of the blood-brain barrier or an intracerebral delivery effect of a desired medicinal component is obtained, and can be determined depending on the disease to be treated or prevented; the type, amount, and route of administration of the desired medicinal component to be administered; the symptoms, sex, and age of the patient; and the like as appropriate. The dose can be determined, for example, by using the amount of medicinal component delivered to the brain or the therapeutic or preventive effect thereby as an indicator. The active ingredient at a dose of usually about 0.01-20 mg/kg body weight, preferably about 0.1-10 mg/kg of body weight, further preferably about 0.1-5 mg/kg of body weight is conveniently administered by intravenous injection about 1-10 times a month, preferably about 1-5 times a month. The above amount may be applied to parenteral administration via another route or oral administration. When symptoms are particularly severe, the dose or frequency of administration may be increased according to the symptoms.

4. Apparatus for Judging Brain Metastasis/Apparatus for Assessing Risk of Brain Metastasis (Apparatus for Judging Brain Metastasis)

Figure 21:
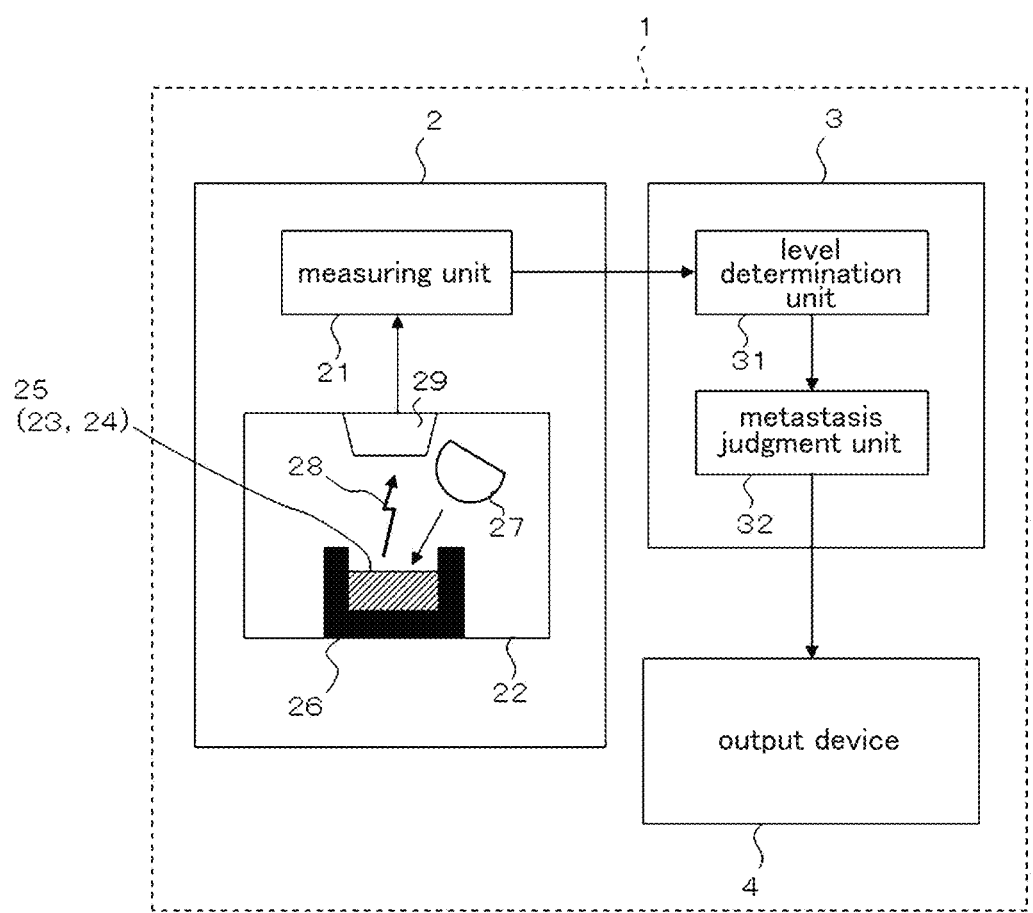
FIG. 21 A schematic configuration diagram of an apparatus for judging brain metastasis relating to an embodiment of the present invention.

In one aspect, the present invention relates to an apparatus for judging brain metastasis that measures an miR-181c level. As illustrated in FIG. 21, an apparatus for judging brain metastasis 1 relating to this embodiment is an apparatus for judging brain metastasis in a subject cancer patient. More specifically, the apparatus for judging brain metastasis 1 is an apparatus for judging whether a cancer patient with suspected brain metastasis (usually Stage IV patient) has brain metastasis. The apparatus for judging brain metastasis 1 comprises a measuring unit 21, a level determination unit 31, and a metastasis judgment unit 32, described below. In this embodiment, the apparatus for judging brain metastasis 1 comprises an input device 2 comprising at least the measuring unit 21, an information processing device 3 comprising at least the level determination unit 31 and the metastasis judgment unit 32, and an output device 4. However, the input device 2, the information processing device 3, and the output device 4 does not need to be separate devices and two or more of these devices 2, 3, and 4 may be configured as one device.

The input device 2 comprises the measuring unit 21 that functions as an miR-181c-measuring means and preferably further comprises a preparation entry/exit unit 22, but the preparation entry/exit unit 22 may be separate from the input device 2. The input device 2 is, for example, a computer comprising a central processing unit (CPU), a read-only memory (ROM), a random access memory (RAM) and a hard disk drive (HDD) or an apparatus containing a computer. Processing in the measuring unit 21 is mainly performed by the CPU reading a computer program in the HDD. The computer program may be, for example, stored in the RAM or the ROM, but not stored in the HDD.

The measuring unit 21 is a component having functions as miR-181c-measuring means that measures a polynucleotide having the nucleotide sequence of miR-181c or a part thereof in a sample 23. The preparation entry/exit unit 22 preferably comprises a preparation holder 26 for holding a preparation 25 containing the sample 23 and a reagent 24, an illuminator 27 for irradiating excitation light to the preparation 25, and a photodetector 29 for detecting fluorescence 28 emitted from the preparation 25 irradiated by the excitation light. When the preparation 25 itself can emit light without irradiating excitation light from the outside, the preparation entry/exit unit 22 does not need to comprise the illuminator 27 and the photodetector 29 detects the emitted light but not fluorescence.

The information processing device 3 comprises at least the level determination unit 31 and the metastasis judgment unit 32. The information processing device 3 is preferably a computer with a CPU, a ROM, a RAM, and an HDD. Processing in both of the level judgment unit 31 and the metastasis judgment unit 32 is mainly performed by the CPU reading a computer program in the HDD. The computer program may not be stored in the HDD, for example, but stored in the RAM or the ROM. The input device 2 and the information processing device 3 may comprise a common CPU, common ROM, common RAM, or a common HDD. In this case, the computer program may be stored in an HDD, a RAM, or a ROM that is common to the input device 2 and the information processing device 3.

The level determination unit 31 is a component that functions as miR-181c level-determining means that receives electrical signals from the measuring unit 21 in the input device 2 and determines the miR-181c level in the measured sample 23. The metastasis judgment unit 32 is a component that functions as metastasis-judging means for judging brain metastasis in the subject cancer patient from the miR-181c level determined in the level determination unit 31. The metastasis judgment unit 32 uses a sample obtained from the subject cancer patient as the sample 23, and judges that the subject cancer patient has brain metastasis if the miR-181c level in the sample is higher than the miR-181c level in a sample from a negative control. The determination by the level determination unit 31 is preferably performed by the CPU reading the information (for example, standard curve data) stored in a memory such as the HDD or the RAM beforehand, and referring to the information. However, the information may not be stored in a memory beforehand, and can be sequentially accumulated by measuring a polynucleotide having the nucleotide sequence of miR-181c or a part thereof with using a concentration predetermined control sample (for example, a sample in a series of serial dilution) as the sample 23. The judgment by the metastasis judgment unit 32 is preferably performed by the CPU reading the information (that is, information on the miR-181c level in the sample from the negative control) stored beforehand in a memory such as the HDD or the RAM and referring to the information. However, the information may not be stored in the memory beforehand, and can be sequentially accumulated by measuring a polynucleotide having the nucleotide sequence of miR-181c or a part thereof in the sample from the negative control used as the sample 23.

The output device 4 is an apparatus for outputting the judgment by the metastasis judgment unit 32 and, for example, can be a monitor for outputting still image or an animation. The output device 4 may be a computer comprising, for example, a CPU, a ROM, a RAM and an HDD or an apparatus containing the computer, like as the input device 2 or the information processing device 3. In that case, the computer program may be stored in an HDD, a RAM, or ROM which is common to the input device 2, the information processing device 3, and the output device 4, or common to the input device 2 and the output device 4, or common to the information processing device 3 and the output device 4.

The output device 4 is not limited to a monitor and may be a device that outputs the judgment in any output form such as a speaker that outputs the judgment with sound, a printer that prints the judgment onto a medium such as paper, or a luminescent device that outputs the judgment in the form of luminescence.

(Apparatus for Assessing Risk of Brain Metastasis)

Figure 22:
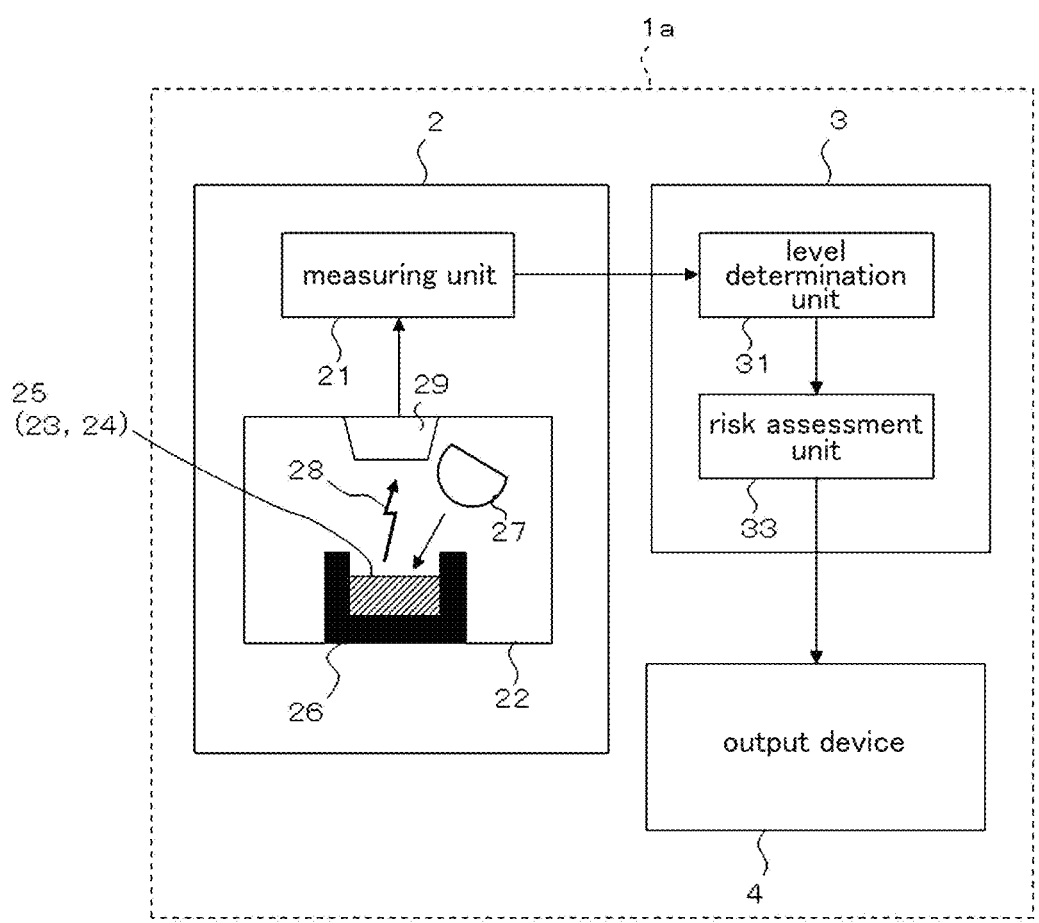
FIG. 22 A schematic configuration diagram of an apparatus for assessing risk of brain metastasis relating to an embodiment of the present invention.

In another aspect, the present invention relates to an apparatus for assessing risk of brain metastasis by measuring an miR-181c level. As illustrated in FIG. 22, an apparatus for assessing risk of brain metastasis 1a of this embodiment is an apparatus for assessing the risk of brain metastasis of a subject cancer patient (usually a Stage I, II, or III patient) who does not yet have brain metastasis. The apparatus for assessing risk of brain metastasis 1a comprises a measuring unit 21, a level determination unit 31, and a risk assessment unit 33 described below. In this embodiment, the apparatus for assessing risk of brain metastasis 1a has a configuration similar to that of the apparatus for judging brain metastasis 1 described above, and comprises an input device 2, an information processing device 3, and the output device 4. However, the apparatus for assessing risk of brain metastasis 1a does not need to be an apparatus in such a form that the input device 2, the information processing device 3, and the output device 4 are separated, like the apparatus for judging brain metastasis 1. Two or more of the devices 2, 3, and 4 may be configured as one device.

The apparatus for assessing risk of brain metastasis 1a comprises a risk assessment unit 33 instead of the metastasis judgment unit 32 in the apparatus for judging brain metastasis 1. The other configuration of the apparatus for assessing risk of brain metastasis 1a is common with the configuration of the apparatus for judging brain metastasis 1 except for the metastasis judgment unit 32. Therefore, the redundant descriptions are omitted.

The risk assessment unit 33 is a component that functions as risk assessment means for judging the risk of brain metastasis in the subject cancer patient from the miR-181c level determined in the level determination unit 31. The risk assessment unit 33 judges that the subject cancer patient has a high risk of brain metastasis if the miR-181c level in a sample 23 from the subject cancer patient is higher than the miR-181c level in a sample from a negative control. The judgment by the risk assessment unit 33 is preferably performed by the CPU reading the information (that is, information on the miR-181c level in the sample from the negative control) stored beforehand in a storage device such as the HDD or the RAM and referring to the information. However, the information may not be stored in the memory beforehand and can be sequentially accumulated by measuring a polynucleotide having the nucleotide sequence of miR-181c or a part thereof in the sample from the negative control used as the sample 23.

5. Computer Program for Brain Metastasis Judgment or Brain Metastasis Risk Assessment In one aspect, the present invention relates to a computer program used in the apparatus for judging brain metastasis or the apparatus for assessing risk of brain metastasis.

(Computer Program for Apparatus for Judging Brain Metastasis)

A computer program of this embodiment is a computer program to be installed in an apparatus for providing information for diagnosing brain metastasis in a subject cancer patient, that is, the above described apparatus for judging brain metastasis 1. The computer program directs the apparatus for judging brain metastasis 1, which is an apparatus for diagnosing brain metastasis in a cancer patient, to execute: an miR-181c-measuring procedure of measuring a polynucleotide having the nucleotide sequence of miR-181c or a part thereof using a sample 23 from the subject cancer patient, an miR-181c level-determining procedure of determining the miR-181c level in the sample 23 measured by the miR-181c-measuring procedure, an metastasis-judging procedure of judging brain metastasis in the subject cancer patient from the miR-181c level determined in the miR-181c level-determining procedure, and a judgement-output procedure of outputting the judgement by the metastasis-judging procedure; wherein the metastasis-judging procedure judges that the subject cancer patient has brain metastasis if the miR-181c level in the sample 23 from the subject cancer patient is higher than the miR-181c level in a sample from a negative control.

The miR-181c-measuring procedure is executed by the measuring unit 21 in the apparatus for judging brain metastasis 1. The miR-181c level-determining procedure is executed by the level determination unit 31 in the apparatus for judging brain metastasis 1. The metastasis-judging procedure is executed by the metastasis judgment unit 32 in the apparatus for judging brain metastasis 1. The judgment-output procedure is executed by the output device 4. These procedures are executed, for example, by a CPU reading the computer program stored in an HDD. This computer program may be a program that executes, by being read by processing of the CPU, the miR-181c-measuring procedure, the miR-181c level-determining procedure, and the metastasis-judging procedure, but not the subsequent judgment-output procedure.

This computer program cannot occupy space by itself, but can be circulated in the market by being stored in an information recording medium. The "information recording medium" is for example, a flexible disk, a hard disk, CD-ROM, CD-R, CD-RW, MO (magneto-optical disk), MD, DVD-R, DVD-RW, a flash memory, a chip card, or the like. By connecting these information recording mediums to a data input and output unit (not illustrated) in the apparatus for judging brain metastasis 1, the computer program can be installed in a memory such as an HDD in the apparatus for judging brain metastasis 1. It is also possible to transmit this computer program to the apparatus for judging brain metastasis 1 from a different computer storing the computer program through a communication line and install it in a memory such as an HDD in the apparatus.

Figure 23:
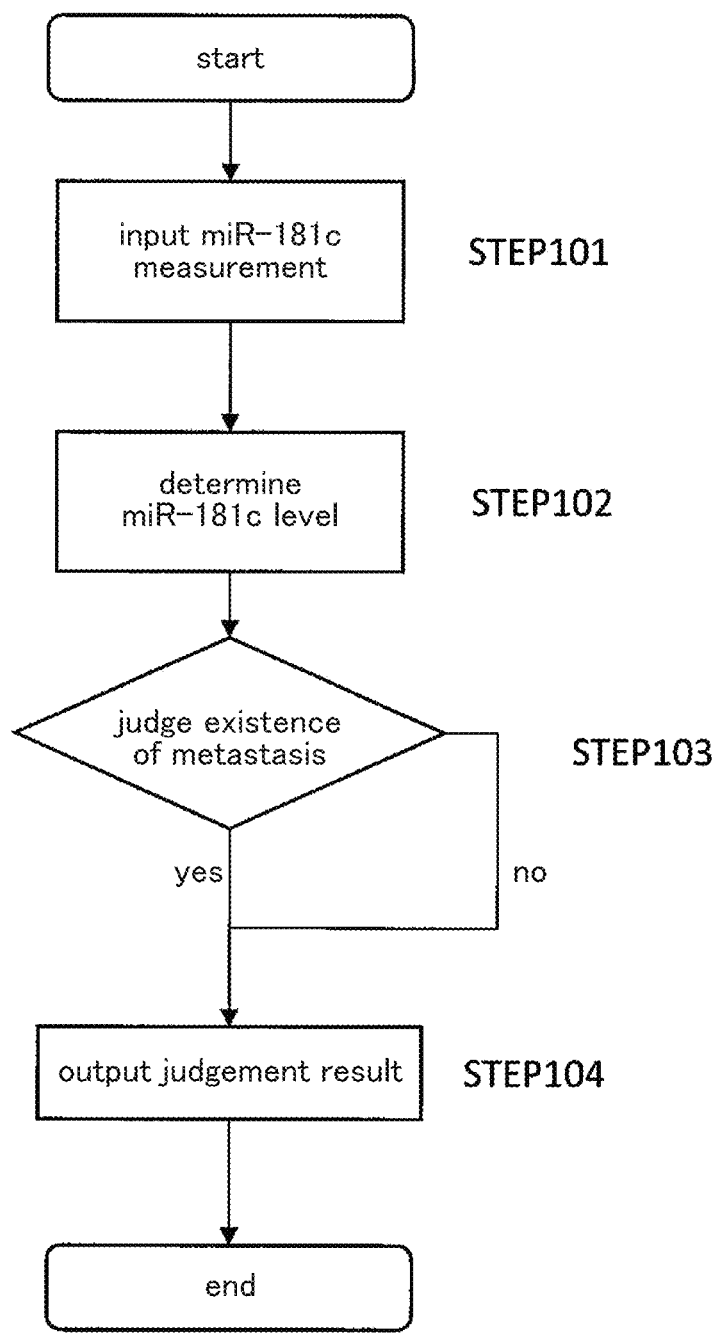
FIG. 23 A flow of processing that the apparatus for judging brain metastasis performs when the computer program for the apparatus for judging brain metastasis is executed.

FIG. 23 illustrates a flow of processing that the apparatus for judging brain metastasis performs when the computer program for the apparatus for judging brain metastasis is executed. The CPU in the apparatus for judging brain metastasis 1 reads the computer program for the apparatus for judging brain metastasis stored in a memory such as an HDD in the apparatus 1 and measures the polynucleotide having the nucleotide sequence of miR-181c or a part thereof using a sample 23 from a subject cancer patient (STEP 101: miR-181c-measuring procedure). Then, the CPU reads the computer program and determines the miR-181c level in the sample 23 measured (STEP 102: miR-181c level-determining procedure). Then, the CPU reads the computer program and judges the presence or absence of brain metastasis in the subject cancer patient from the miR-181c level determined in the miR-181c level-determining procedure (STEP 103: metastasis-judging procedure). Then, the CPU reads the computer program and outputs the result of judgement that there is brain metastasis or that there is no brain metastasis from the output device 4 (STEP 104: judgment-output procedure).

(Computer Program for Apparatus for Assessing Risk of Brain Metastasis)

A computer program relating to another embodiment is a computer program to be installed in an apparatus for assessing risk of brain metastasis in a subject cancer patient, that is, the apparatus for assessing risk of brain metastasis 1a. The computer program directs the apparatus for assessing risk of brain metastasis 1a, which is an apparatus for assessing brain metastasis in a cancer patient, to execute: an miR-181c-measuring procedure of measuring a polynucleotide having the nucleotide sequence of miR-181c or a part thereof using a sample 23 from the subject cancer patient, an miR-181c level-determining procedure of determining the miR-181c level in the sample 23 measured by the miR-181c-measuring procedure, a risk-assessing procedure of assessing risk of brain metastasis in the subject cancer patient from the miR-181c level determined in the miR-181c level-determining procedure; an assessment-output procedure of outputting the assessment by the risk-assessing procedure; wherein the risk-assessing procedure judges that the subject cancer patient has a high risk of brain metastasis if the miR-181c level in the sample 23 from the subject cancer patient is higher than the miR-181c level in a sample from a negative control.

The risk-assessing procedure is executed by the risk assessment unit 33 in the apparatus for assessing risk of brain metastasis 1a. The miR-181c-measuring procedure, the miR-181c level-determining procedure, and the assessment-output procedure are respectively executed by the measuring unit 21, the level determination unit 31, and the output device 4 as the same manner with the computer program for the apparatus for judging brain metastasis described above. These procedures are executed, for example, by a CPU reading the computer program stored in an HDD. This computer program may be a program that executes, by being read by processing of the CPU, the miR-181c-measuring procedure, the miR-181c level-determining procedure, and the risk-assessing procedure, but not the subsequent assessment-output procedure.

This computer program can be also stored in an information recording medium illustrated above. By connecting these information recording mediums to a data input and output unit (not illustrated) in the apparatus for assessing risk of brain metastasis 1a, the computer program can be installed in a memory such as an HDD in the apparatus for assessing risk of brain metastasis 1a. It is also possible to transmit this computer program to the apparatus for assessing risk of brain metastasis 1a from a different computer storing the computer program through a communication line and install it in a memory such as an HDD in the apparatus.

Figure 24:
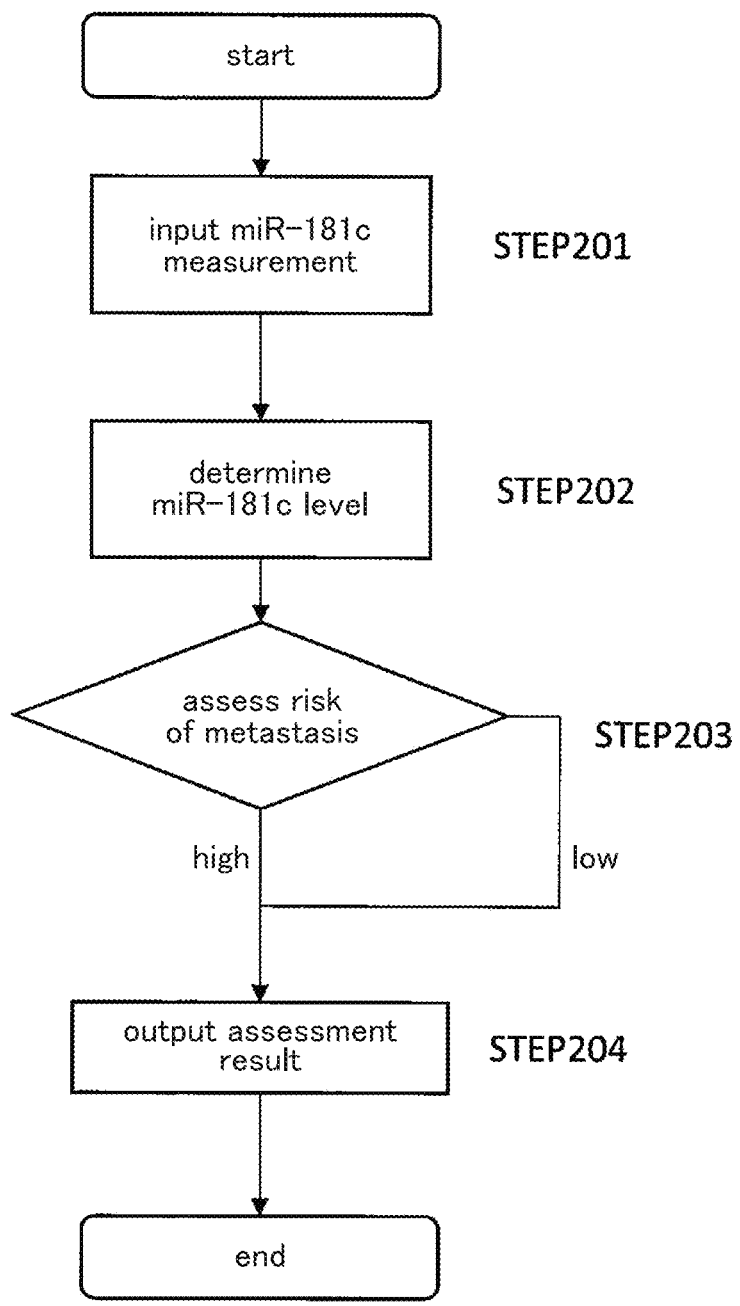
FIG. 24 A flow of processing that the apparatus for assessing risk of brain metastasis performs when the computer program for the apparatus for assessing risk of brain metastasis is executed.
Figure 25:
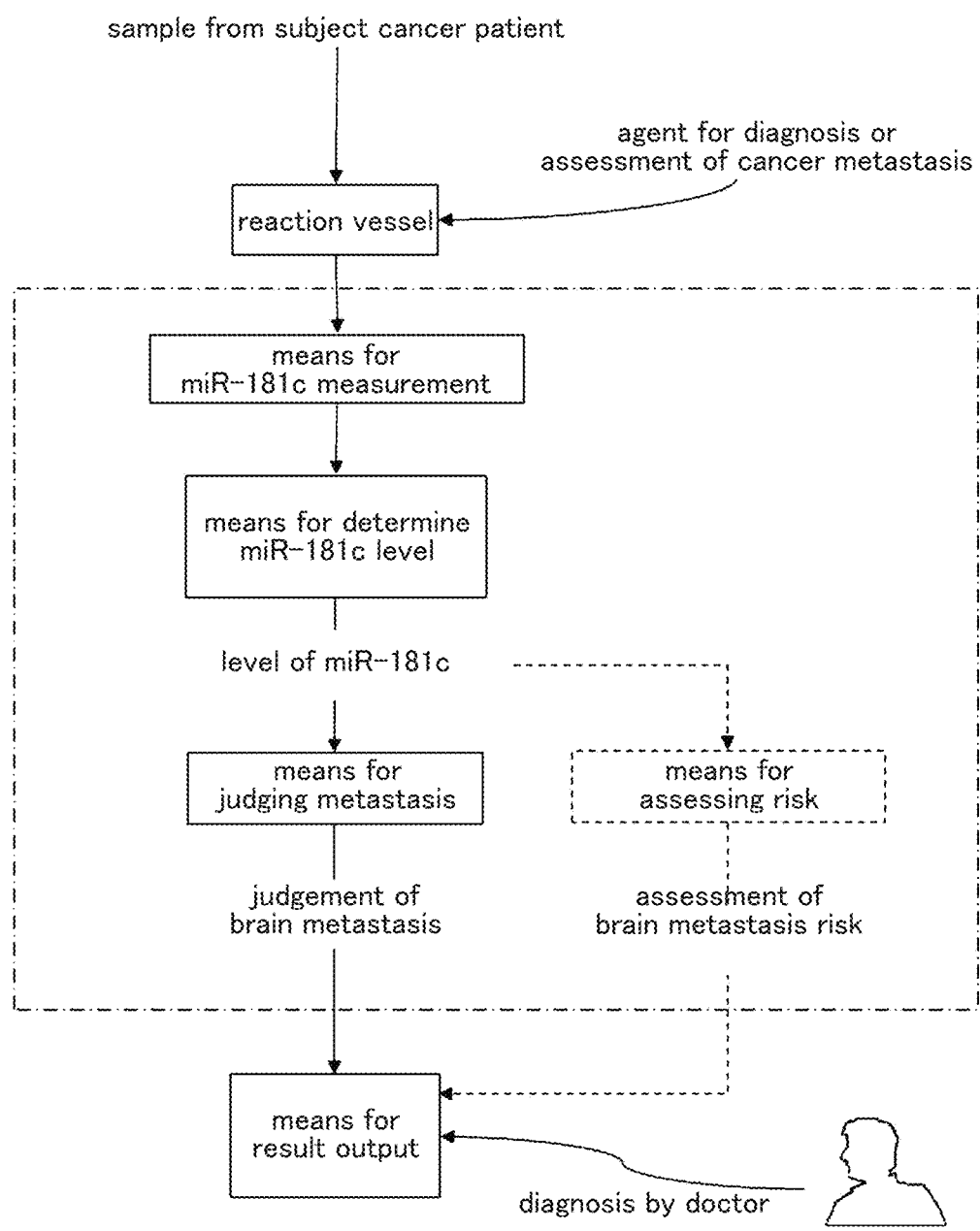
FIG. 25 A schematic diagram of an apparatus of the present invention and a method for judging brain metastasis (solid line) or a method for assessing risk of brain metastasis (dotted line) using the apparatus.

FIG. 24 illustrates a flow of processing that the apparatus for assessing risk of brain metastasis performs when the computer program for the apparatus for assessing risk of brain metastasis is executed. The CPU in the apparatus for assessing risk of brain metastasis 1a reads the computer program for the apparatus for assessing risk of brain metastasis stored in a memory such as an HDD in the apparatus 1a and measures the polynucleotide having the nucleotide sequence of miR-181c or a part thereof using a sample 23 from a subject cancer patient (STEP 201: miR-181c-measuring procedure). Then, the CPU reads the computer program and determines the miR-181c level in the sample 23 measured (STEP 202: miR-181c level-determining procedure). Then, the CPU reads the computer program and assesses whether the risk of brain metastasis in the subject cancer patient is high or low from the miR-181c level determined in the miR-181c level-determining procedure (STEP 203: risk-assessing procedure). Then, the CPU reads the computer program and outputs the result of assessment that the risk of brain metastasis is high or that the risk of brain metastasis is low from the output device 4 (STEP 204: judgment-output procedure).

Although the present invention will be hereinafter described in detail with reference to Examples, the present invention is not intended to be limited thereto. The all documents cited throughout the present application are incorporated as it is into the present application by reference.

EXAMPLES

In the experiments described in Examples below, all experiments using animals were conducted according to the protocols approved by the Institutional Animal Care and Use Committee of National Cancer Center (Independent Administrative Institution). In experiments described below, all numerical values are expressed as mean+/−standard deviation (S.D.). P values less than 0.05 by Student's t-test or Mann-Whitney U test were considered to be statistically significant.
(Cell Culture)

In the experiments described in the Examples, MDA-MB-231-luc-D3H1 cells, MDA-MB-231-luc-D3H2LN cells, BMD2a cells, and BMD2b cells were cultured in the RPMI 1640 medium containing 10% heat inactivated fetal bovine serum (Invitrogen) and antimicrobial-antifungal agents at 37° C., 5% $CO_2$.

(Example 1) Establishment of Brain Metastasis Breast Cancer Cell Line

Brain metastasized cell lines were newly generated using highly tumorigenic and metastatic human breast cancer cells, MDA-MB-231-luc-D3H2LN cells (hereinafter, referred to as the "D3H2LN cells") (Bos, P. D. et al., Nature, 459:1005-1009 (2009)) (FIG. 1a). Specifically, 100 µL of a cell suspension containing $2 \times 10^5$ D3H2LN cells was administered by intracardiac injection to the left ventricle in 7 week-old female C.B-17/Icr-scid/scid immunodeficient mice. The mice were observed every week for tumorigenesis by brain metastasis by bioluminescence in vivo imaging after intraperitoneal injection of luciferin using IVIS Spectrum (Caliper Life Science, Hopkinton, Mass., USA). 26-30 days later, brain metastasis of cancer cells was observed (FIG. 1b).

The brain metastasis sites were examined by histologic analysis after dissection. Cancer cell colonization in brain tissue was confirmed by fixation of half of the tissue with 4% para-formaldehyde and histologic analysis with hematoxylin-eosin (HE) staining (FIG. 1c).

To collect and culture brain metastatic cancer cells, the remaining half of the tissue was ground and added to the RPMI 1640 medium (Gibco) containing antimicrobial-antifungal agents and 10% FBS. After centrifugation for a short time, the cells were resuspended with 0.025% trypsin-EDTA (Gibco) and incubated at 37° C. for 10 minutes. The cells were resuspended in a medium containing 50 µg/mL of Zeocin (Gibco), then seeded in a 10 cm dish, and cultured and grown to confluent for approximately 30 days.

Using the grown cell population (brain metastatic derivative 1a, hereinafter, referred to as the "BMD1 cells"), the second in vivo selection was conducted in the way same as that described above and two brain metastatic derivative cell populations 2a and 2b (hereinafter, respectively referred to as the "BMD2a cells" and the "BMD2b cells") were obtained.

The obtained BMD2a and BMD2b cells were administered to mice like the D3H2LN cells and examined their brain metastasis activities. As a result, while brain metastasis was observed only 1 mouse (6.7%) out of the 15 mice in which the D3H2LN cells were injected into the left ventricle, 60% (3 out of 5) of the mice in which the BMD1a cells are injected into the left ventricle had brain metastasis. Accordingly, it was demonstrated that the BMD2a and BMD2b cells have a markedly increased brain metastasis activity compared to the parental D3H2LN cells.

(Example 2) Construction of In Vitro Blood-Brain Barrier (BBB) Model (1) In Vitro Blood-Brain Barrier Model An in vitro BBB culture system was constructed to measure effects on BBB easily. Conventional in vitro blood-brain barrier models use monolayer cell culture systems (Zhou, W. at al, J. Biol. Chem., 288:10849-10859). However, BBB consists of three different types of cells and these cells cooperate with each other to maintain the structure of BBB. Therefore, BBB Kit™ (#MTB-24H, PharmaCo-Cell Company Ltd., Nagasaki, Japan), which is a BBB model system that consists of primary cultures of brain capillary endothelial cells, brain pericytes and astrocytes (FIG. 2a) was used. Brain capillary endothelial cells, brain pericytes, and astrocytes were confirmed by Hoechst33342 staining. As a result, the presence of brain capillary endothelial cells, brain pericytes, and astrocytes in the constructed in vitro blood-brain barrier model was confirmed as illustrated in FIG. 2b.

(2) Confirmation of Localization of Tight Junction Proteins and the Like in Endothelial Cells Tight junctions are known to regulate the low permeability of BBB and are formed by specific proteins in endothelial cells (such as Claudin-5, Occludin, and ZO-1). Meanwhile, N-cadherin, which is a calcium-dependent cell-cell adhesion glycoprotein and has five extracellular cadherin repeats to mediate strong cell-cell adhesion, is mostly expressed on the apical and basal membranes. Tight junction proteins and N-cadherin regulate cell polarity through their intimate association with the actin cytoskeletal network. Therefore, the formation of tight junction and adherens junction were confirmed by fluorescently immunostaining Claudin-5, Occludin, ZO-1, or N-cadherin in the endothelial cells in the in vitro BBB model to confirm their localization.

Specifically, the endothelial cells collected from the in vitro BBB model were fixed with PBS containing 3% PFA at room temperature for 10 minutes, washed with PBS containing $Mg^{2+}$ and $Ca^{2+}$, and then treated with PBS containing 0.1% Triton-X100 for 10 minutes to permeabilize the cells. After fixation, the cells were incubated with PBS containing 3% BSA for 1 hour to block nonspecific binding of antibody. Subsequently, the endothelial cells were incubated at 37° C. with a rabbit polyclonal antibody to Claudin-5 (Z43.JK, Invitrogen, CA, USA), Occludin (ZMD.467, Invitrogen), ZO-1 (ZMD.437, Invitrogen), or N-cadherin (3B9, Invitrogen) for 1 hour. After washing with PBS containing $Mg^{2+}$ and $Ca^{2+}$, the cells were incubated at 37° C. with 594 Alexa Fluor-fused antirabbit IgG (Invitrogen) for 1 hour. Actin was stained with ActinGreen™ 488 Ready-Probes (TN) Reagent (R37110, Molecular Probes). The stained cells were washed with $Mg^{2+}$ and $Ca^{2+}$ free PBS, then mounted with VECTASHIELD Mounting Medium (H-1200, Vector Laboratories, CA, USA), and observed with a cofocal microscope (FluoViewFV1000, Olympus, Tokyo, Japan).

Figure 2:
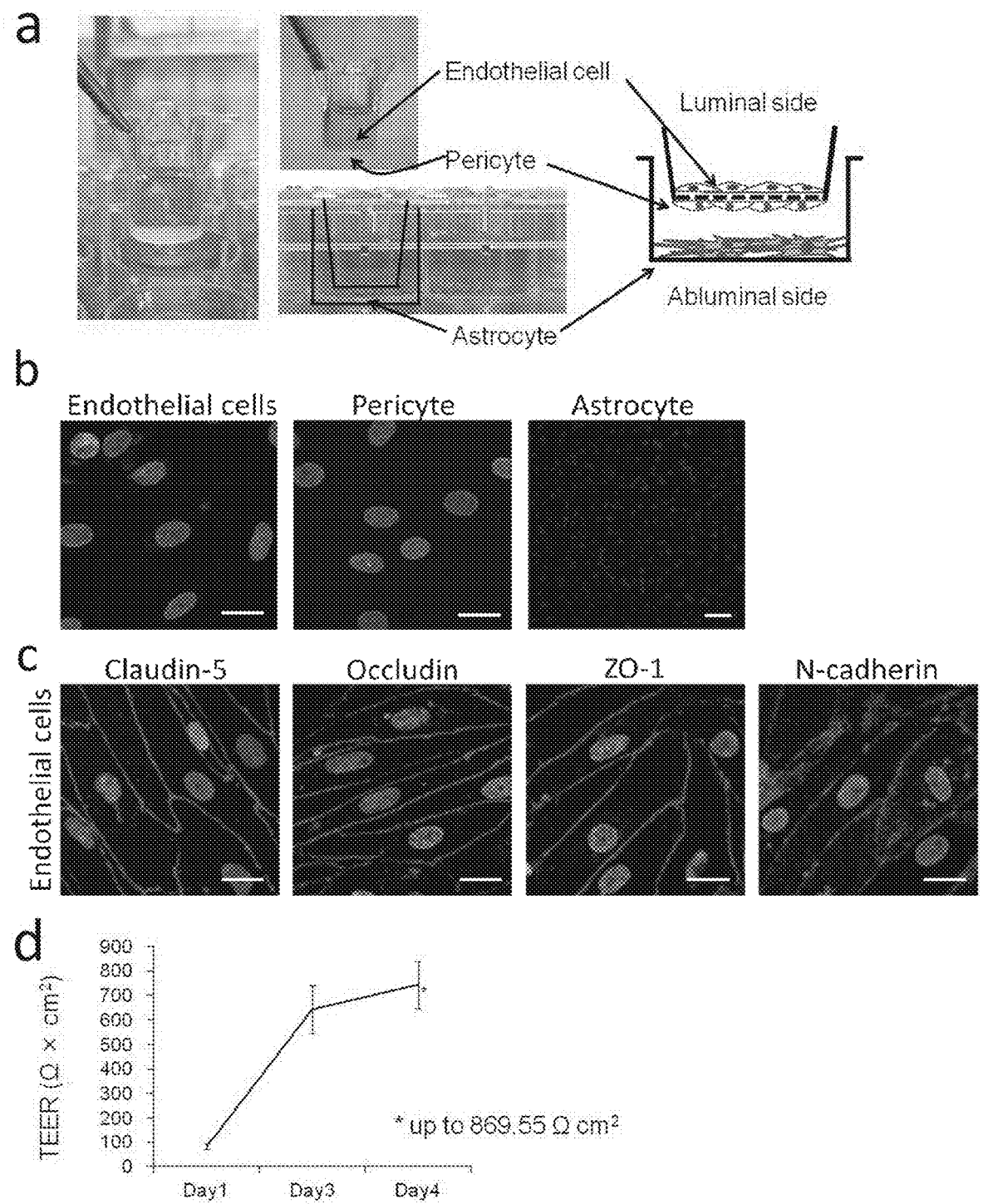
FIG. 2 (a)

It was demonstrated that all of the tight junction proteins (Claudin-5, Occludin, and ZO-1) and N-cadherin bind to the surface of the cell membrane and constitute intercellular tight junction and adherens junction as illustrated in FIG. 2c.
(3) Measurement of Transendothelial Electrical Resistance (TEER)

The formation of tight junction by brain capillary endothelial cells was measured by transendothelial electrical resistance (TEER) (Gaillard, P. J. et al., Eur. J. Pharm. Sci., 12:215-222 (2001), Wilhelm, I. et al., Acta. Neurobiol. Exp. (Wars), 71:113-128 (2011)). The resistance values (Ω) were measured by an ohmmeter (Millicell ERS-2, Millipore). The transendothelial electrical resistance (TEER) values were calculated by means of the unit area resistance by the following calculating formula. $R=(A-B)*0.33\ cm^2$, wherein R denotes TEER ($\Omega*cm^2$), A denotes measurement resistance value (Ω), and B denotes blank resistance value (Ω). It was done for n=12.

FIG. 2d illustrates the result of measuring the formation of tight junction by the brain capillary endothelial cells by transendothelial electrical resistance (TEER). The transendothelial electrical resistance (TEER) exceeded 150, which indicates that this system can be used as an in vitro BBB model.
(4) Permeability Assay NaF does not pass BBB in spite of having a low molecular weight (molecular weight: 376.27) (Nakagawa, S, et al., Neurochem. Int. 54: 253-263 (2009)). Accordingly, permeability of BBB was measured by measuring the concentration of NaF with a fluorescence monochromator. Specifically, a permeability assay modified from a previously described method (B. Kis et al., Adrenomedullin regulates blood-brain barrier functions in vitro. Neuroreport 12, 4139-4142 (2001)) was used. 200 μL of NaF (10 μg/mL, Sigma Aldrich) was added to the upper chamber and 900 μL of DPBS-H (Dulbecco's PBS (Mg+, Ca+) containing 10 mM HEPES and 4.5 mg/mL D-glucose) was added to the lower chamber. The plate was cultured with shaking at 37° C. After 30 min, the DPBS-H of the lower chamber was dispensed into a black plate (n=8) and measured with a multi detection monochrometer microplate reader (485/535 nm, SAFIRE, Tecan). The apparent permeability coefficient (Papp) was calculated by the following calculating formula:

$$Papp=(VA \times [C]A) \times A^{-1} \times [C]Luminal^{-1} \times t^{-1}$$

The abbreviations in the formula denote the following:
VA: volume of abluminal chamber (0.9 cm$^3$)
A: membrane surface area (0.33 cm$^2$)
[C]Luminal: initial luminal tracer concentration (μg/mL)
[C]A: abluminal tracer concentration (μg/mL)
t: time of experiment (min)

The permeability assay conducted by the method described above demonstrated, as a result, that the permeability of NaF is very low.

(Example 3) Examination of Invasive Capacity of Brain Metastatic Cancer Cell Using Matrigel™

Brain metastatic cancer cells are also considered to be highly invasive. Therefore, invasion chamber assays using Matrigel™ were used to confirm the pathological implications of the metastatic potential of established cell lines. BMD2a, BMD2b, D3H2LN, and D3H1 cells were trypsinized and labelled with PKH26 (Sigma Aldrich). $2 \times 10^4$ cells of each cancer cell line were suspend in serum-free RPMI1640 medium and plated in the top chamber with a Matrigel®-coated membrane (24-well insert, BD Biosciences, NJ, USA). RPMI1640 medium containing 10% serum was added to the lower chamber as a chemoattractant. The cells were cultured for 24 hours and cells that did not migrate or invade through the membrane pores were removed using a cotton swab. Cells on the lower surface of the membrane were stained with the Diff-Quick Staining Set (Sysmex, Hyogo, Japan) and counted. All assays were performed in triplicate. The data were expressed as percentage of the number of cells migrating through the Matrigel™ matrix and membrane relative to the number of cells migrating through the control membrane, according to the manufacturer's instructions.

Figure 3:
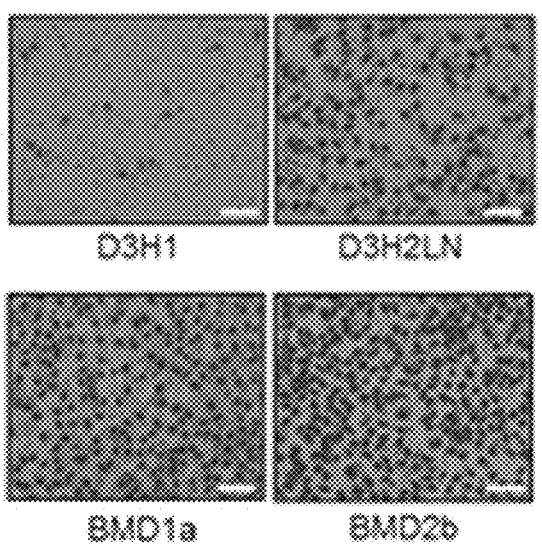
FIG. 3 (a) Representative photographs showing invasiveness of Matrigel by MDA-MB-231-D3H1 cells (hereinafter, D3H1 cells) MDA-MB-231-D3H2LN cells (hereinafter, D3H2LN cells), and BMD2a and BMD2b cells which were established as brain metastasis cell lines. The bar at the lower right corner in each photograph indicates 100 μm. (b) A graph showing the ratio (folds) of the number of D3H1 cells, BMD2a cells, and BMD2b cells invaded Matrigel relative to the number of D3H2LN cells invaded Matrigel. The error bar represents standard deviation (SD), and ** indicates P<0.01. (c) Photographs of representative morphology of D3H1, D3H2LN, BMD2a, and BMD2b cells. The bar at the lower right corner in each photograph indicates 100 μm.
Figure 3:
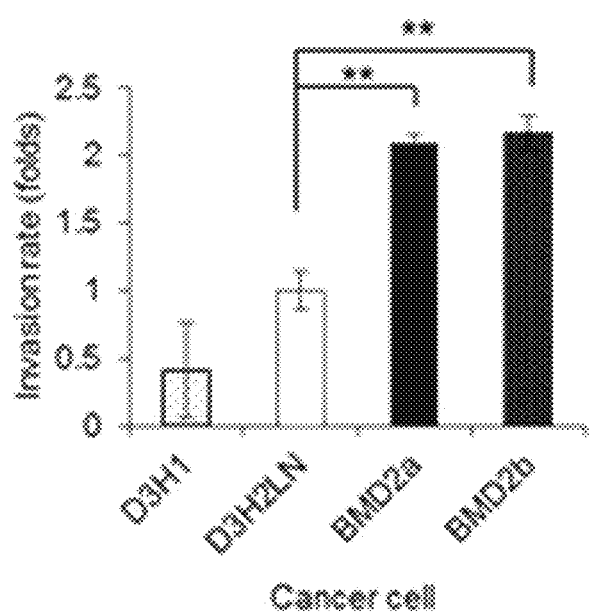
Figure 3:
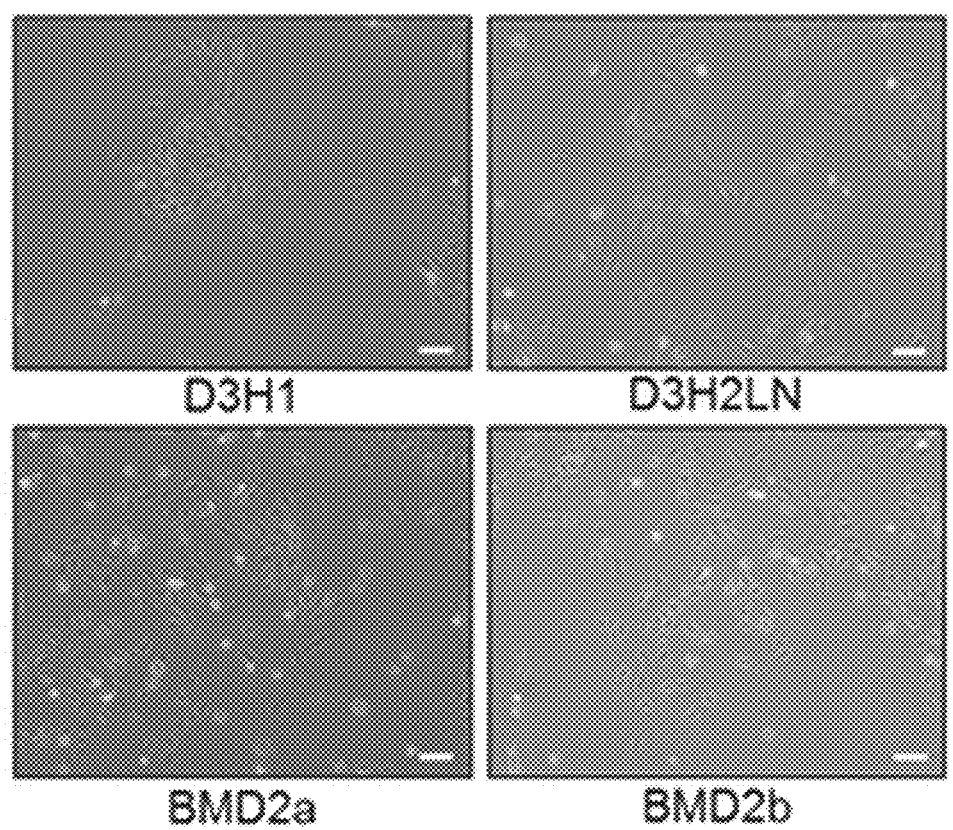

BMD2a and BMD2b cells were more invasive than D3H2LN cells and low-metastatic D3H1 cells (FIGS. 3a and 3b). However, the morphology of BMD2a and BMD2b cells did not differ from that of D3H2LN cells (FIG. 3c).

Figure 4:
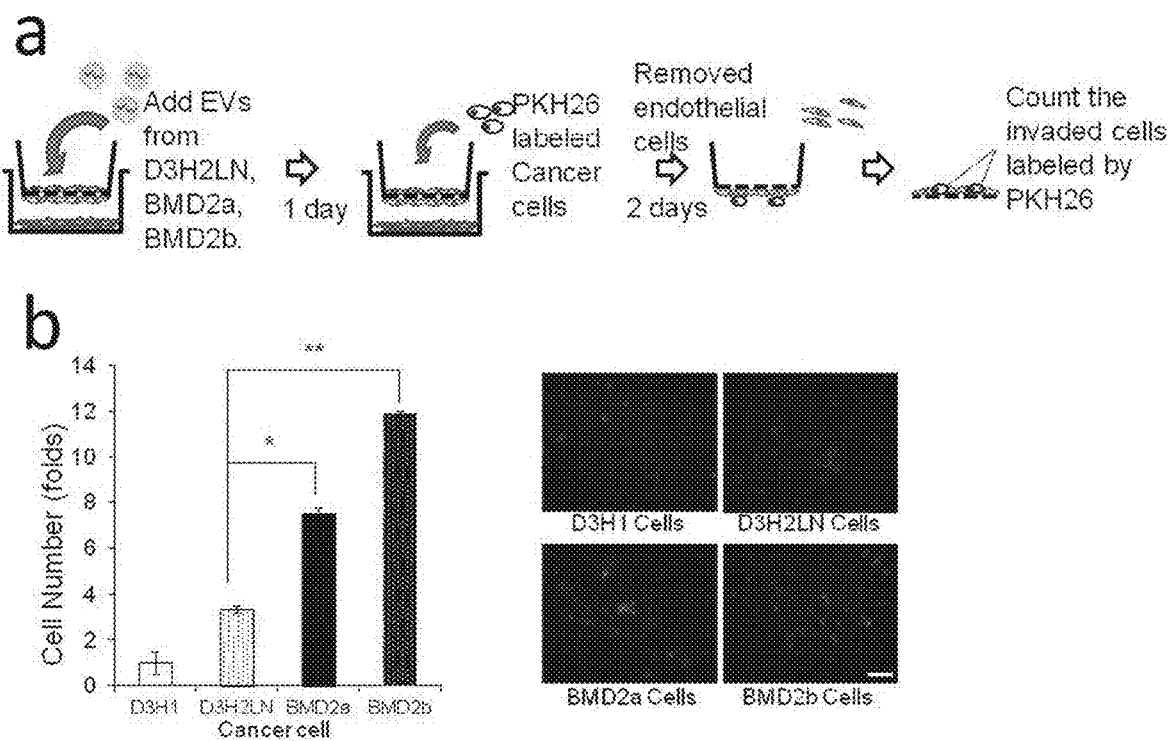
FIG. 4 (a)

(Example 4) Examination of Invasive Capacity of Brain Metastatic Cancer Cells Using BBB Model To confirm the entry of BMD2a and BMD2b cells into the brain parenchyma cell side, BMD2a, BMD2b, D3H2LN and D3H1 cells were trypsinized and labelled with PKH26 (Sigma Aldrich). Subsequently, $2 \times 10^4$ cancer cells were suspended in serum-free Ham's F-12 medium (Gibco) and added to the upper chamber of the in vitro BBB model prepared in Example 2 and cultured. After 2 days (48 hours), non-invading cells were removed with cotton swabs and the nuclei were stained with Hoechst 33342 (Dojindo Laboratories, Kumamoto, Japan). Subsequently, the PKH26 fluorescence of invading cells that had migrated to the lower surface side was counted with a fluorescence microscope (FIG. 4a). All cells were assayed in triplicate.

BMD2a and BMD2b cells were more invasive than D3H2LN and D3H1 cells (FIG. 4b). Accordingly, it was confirmed that the established BMD2a and BMD2b cells have a high potential for entry into the brain parenchymal cell side across BBB.

(Example 5) Preparation of EVs

D3H1, D3H2LN, BMD2a, and BMD2b cells were washed three times with Advanced RPMI medium containing antibiotic-antimycotic agents and 2 mM L-glutamine (hereinafter, referred to as the "medium A"). Fresh medium A was added to the washed cells and cultured for 2 days, and then the medium was collected and centrifuged at 2000*g for 10 min at 4° C. To thoroughly remove cellular debris, the culture supernatant was filtered with a 0.22-μm Stericup® (Millipore, MA, USA). The resultant conditioned medium was ultracentrifuged at 110,000*g for 70 min at 4° C. The resultant pellets were washed with 11 mL of phosphate buffered saline (PBS) and resuspended in PBS.

The fraction containing the EVs was measured for its protein content using the Micro BCA protein assay kit (Thermo Scientific, MA, USA). The obtained EVs was observed by phase contrast microscopy. Furthermore, the size and the number of the EVs were measured with Nano-Sight.

The expression of the standard exosomal markers CD63 and CD9 and the expression of the mitochondrial intermembrane protein Cytochrome C, which is known to be lacking in EVs, was measured by Western blotting. Samples were obtained from each cell line using M-PER (Thermo Scientific, MA, USA) and loaded in Mini-PROTEAN® TGX Gel (4-12%) (Bio-Rad) at 500 ng/lane (CD63 and CD9) or 3 μg/lane (Cytochrome C) and proteins were separated and then electrotransferred onto PVDF membranes (Millipore). The resultant membranes were blocked in Blocking One (Nacalai Tesque, Kyoto, Japan) and then incubated for 1 hour at room temperature with a primary antibody, anti-CD63 antibody (purified mouse anti-human CD63, H5C6, 1/200, BD), anti-CD9 antibody (ALB6, sc-59140, 1/200, BD), or anti-cytochrome C antibody (purified mouse anti-cytochrome C, 7H8.2C12, 1/200, BD). An HRP-linked anti-mouse IgG secondary antibody (NA931, GE Healthcare) or HRP-linked anti-rabbit IgG secondary antibody (NA934, GE Healthcare) was used at a dilution of 1/2000. The membranes were then made luminescent with ImmunoStar® LD (Wako, Osaka, Japan).

Figure 5:
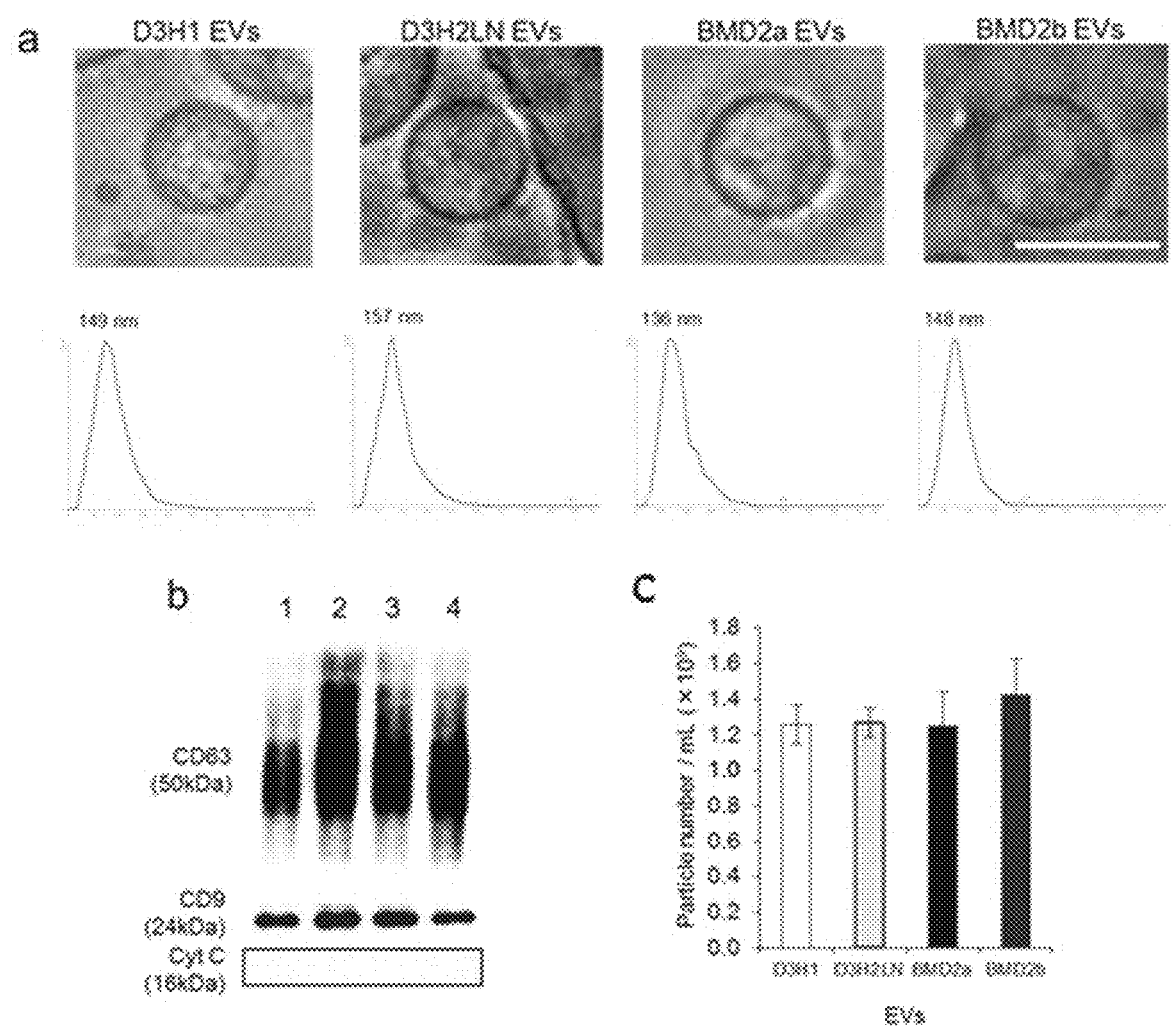
FIG. 5 (a) The upper panels are photographs of EVs visualized with a phase-contrast electron microscope. The bars represent 100 nm. The lower panels are graphs of the results of measurements of the EV sizes with NanoSight. The numerical values in the graphs are the mean values of the size of all EVs. (b) A photograph of the result of Western blotting to confirm the expression of CD63 and CD9 as the EV markers and Cytochrome C. In the photograph, from the left to the right, each lane shows D3H1 derived EVs (lane 1), D3H2LN derived EVs (lane 2), BMD2a derived EVs (lane 3), and BMD2b derived EVs (lane 4). (c) A graph of the result of measurement of the number of EVs isolated from D3H1, D3H2LN, BMD2a, and BMD2b cells with NanoSight. The horizontal axis indicates, from the left to the right, D3H1 derived EVs, D3H2LN derived EVs, BMD2a derived EVs, and BMD2b derived EVs. The vertical axis represents the number of EV particles per 1 mL ($\times 10^9$/mL).

As for the protein content, there was no difference in protein concentration among the EVs derived from D3H1 cells, the EVs derived from D3H2LN cells, the EVs derived from BMD2a cells, and the EVs derived from BMD2b cells. FIG. 5a illustrates photographs resulted from the phase contrast microscope observation and the result of the analysis of EV size. The average particle sizes of the EVs derived from D3H1 cells, D3H2LN cells, BMD2a cells, and BMD2b cells were 149 nm, 157 nm, 136 nm, and 148 nm, respectively. All these EVs expressed the standard exosomal markers CD63 and CD9 but not Cytochrome C (FIG. 5b). Furthermore, the number of EV release did not differ among the cells (FIG. 5c).

(Example 6) Examination of Correlation Between Secretion of EVs and Invasive Capacity of Cancer Cells To examine the involvement of EVs in the invasion of brain metastatic cells, the invasive capacity of BMD2a cells in which the EVs secretion was inhibited by siRNAs (Kosaka, N. et al., J. Biol. Chem., 288:10849-10859 (2013); Ostrowski, M et al., Nat. Cell Biol., 12:19-30 (2010)) against nSMase2 and RAB27B, which are proteins involved in the EVs secretion, was assessed in the in vitro BBB model (1) siRNA Transfection 25 nM each of either or both of RAB27B siRNA and nSMase2 siRNA or control siRNA was introduced into PKH26-labelled BMD2a cells using the DharmaFECT transfection reagent (Thermo Scientific) according to the manufacturer's protocol. Cells 24 hours after the transformation were used in assay.

(2) Confirmation of Expression of nSMase2 and RAB27B at mRNA Level in siRNA-Introduced Cells Total RNA was extracted from cells using QIAzol reagent and RNeasy Mini Kit (both Qiagen). RNU6 was used as an internal control according to a described method (Kosaka, N. et al., Net. Med., 18:883-891 (2012)). The expression level of each mRNA and RNU6 was measured with qRT-PCR performed in 96-well plates using Platinum Quantitative PCR SuperMix (Applied Biosystems) with the 7300 Real-Time PCR System (all Applied Biosystems, CA, USA). All reactions were performed in triplicate. The primers and probes were defined as follows: PAB27B (assay ID: Hs01072206_m1), nSMase2 (assay ID: Hs00920354_m1).

(3) Confirmation of Expression of nSMase2 at Protein Level in siRNA-Introduced Cells Expression of nSMase2 in siRNA-introduced cell was confirmed at the protein level by Western blotting. Samples were obtained from each cell line using M-PER (Thermo Scientific, MA, USA) and loaded in Mini-PROTEAN® TGX Gel (4-12%) (Bio-Rad) and proteins were separated and then electrotransferred onto PVDF membranes (Millipore). The resultant membranes were blocked in Blocking One (Nacalai Tesque, Kyoto, Japan) and then incubated for 1 hour at room temperature with a primary antibody, anti-nSMase2 antibody (H-195, sc-67305, 1/200, Santa Cruz Biotechnology Inc.). An HRP-linked anti-mouse IgG secondary antibody (NA931, GE Healthcare) or HRP-linked anti-rabbit IgG secondary antibody (NA934, GE Healthcare) was used at a dilution of 1/2000. The membranes were then made luminescent with ImmunoStar® LD (Wako, Osaka, Japan).

(4) Measurement of Number of EV Release from siRNA-Introduced Cells

The number of EV release from siRNA-introduced cells were measured with NanoSight.

(5) Examination of Invasive Capacity of Brain Metastatic Cancer Cell Using BBB Model The Matrigel invasion capacity of generated transformation cells and migration across BBB were examined according to the methods in Example 3 and Example 4, respectively.

(6) Results

Figure 6:
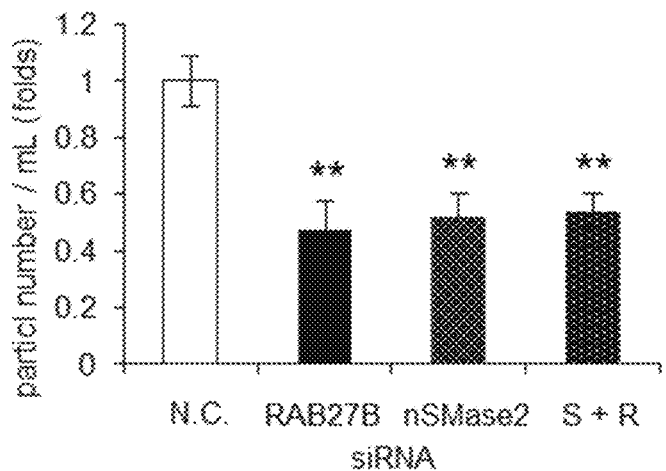
FIG. 6 Graphs of the results of treatment of BMD2a cells with siRNAs. In all graphs, the horizontal axis indicates treated siRNAs, which are from the left to the right, negative control cells (N.C.), RAB27B siRNA (RAB27B), nSMase2 siRNA (nSMase2), and RAB27B siRNA and nSMase2 siRNA (S+R). (a) A graph showing the number of EVs released from siRNA-treated BMD2a cells. The vertical axis represents the ratio (folds) of the number of EV particles (unit/mL) from cells treated with siRNA against the EV-release related protein relative to the number of EV particles from the negative control cells. (b) A graph of siRNA-treated BMD2a cells invaded Matrigel. The vertical axis represents the ratio (%) of the number of Matrigel invaded cells treated with siRNA against an EV-release related protein relative to that of the negative control cells. (c) A graph showing the result of the in vitro BBB transmigration activity test of siRNA-treated BMD2a cells. The vertical axis represents the ratio (folds) of the number of BBB transmigrated cells treated with siRNA against an EV-release related protein relative to that of the negative control cells.
Figure 6:
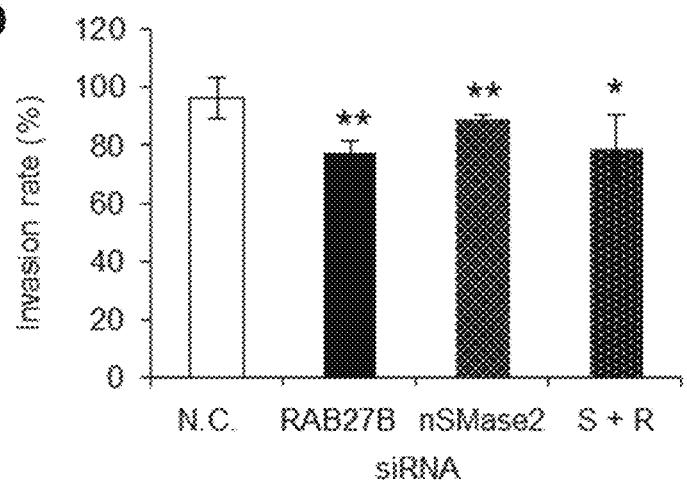
Figure 6:
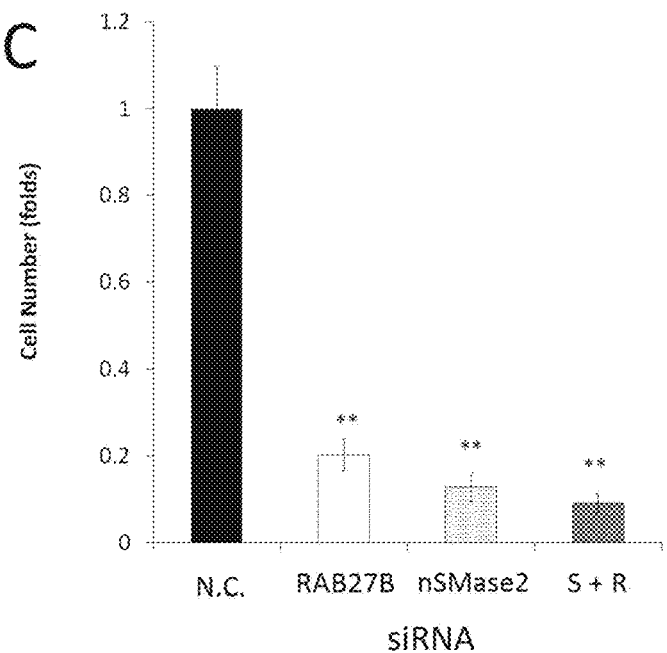

The cells into which either of nSMase2 siRNA and RAB27B siRNA was introduced and the cells into which both of the siRNAs were introduced had a reduced expression of nSMase2 and RAB27B at both mRNA and protein levels compared to the control siRNA-introduced cells (not shown). According to the result of measurement of the number of EV release from siRNA-introduced cells, the cells into which either of nSMase2 siRNA and RAB27B siRNA was introduced and the cells into which both of the siRNAs were introduced had a reduced number of EV release compared to the control siRNA-introduced cells (FIG. 6a). According to the result of test on capacity to migrate across BBB, while the cells treated with control siRNA migrated to the lower side across BBB, the cells in which the production of EVs was inhibited were not found on the lower side (FIG. 6c). In the invasive capacity assay using Matrigel, the inhibition of EVs secretion did not affect the invasive capacity of the cells (FIG. 6b). From this, it was suggested that extravasation is not only dependent on the cells' invasive capacity.

(Example 7) Examination of Correlation Between EVs and BBB Invasive Capacity of Cancer Cells Furthermore, to investigate whether EVs are involved in the extravasation of cancer cells to the brain parenchymal cell side, whether low-metastatic D3H1 cells migrate across BBB and extravasate after the addition of BMD2a cell-, BMD2b cell-, or D3H2LN cell-derived EVs or not was examined.

The EVs derived from BMD2a, BMD2b, or D3H2LN cells were added to each well and then incubated for 24 hours. Subsequently, PKH26-labelled D3H1 cells were added. After 2 days, the number of cells migrated across the filter was counted.

Figure 7:
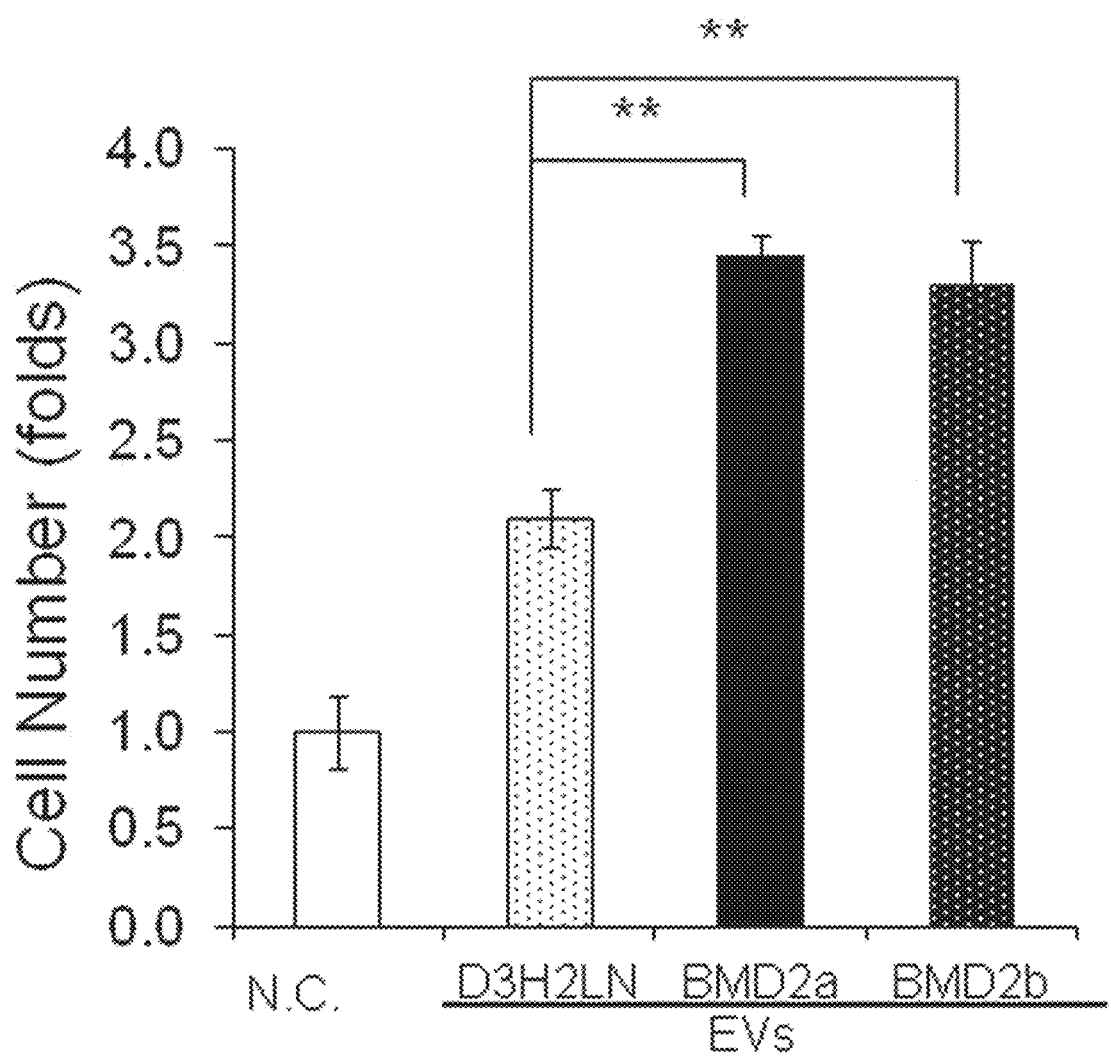
FIG. 7 A graph of the result of measurement of the BBB transmigrating capacity of D3H1 cells on addition of EVs derived from BMD2a, BMD2b, or D3H2LN cells using the in vitro BBB model. The vertical axis represents the ratio (folds) of the number of D3H1 cells that migrated across the in vitro BBB model on addition of EVs derived from BMD2a, BMD2b, or D3H2LN cells relative to that of the negative control cells. The horizontal axis indicates the cells from which the added EVs are derived, which are from the left to the right, negative control (N.C.), D3H2LN, BMD2a, and BMD2b cells.

The result is illustrated in FIG. 7. D3H1 cells could not migrate across BBB without the addition of EVs. However, the number of cells that migrated across BBB to the lower side was significantly increased by the addition of BMD2a cell- and BMD2b cell-derived EVs. The addition of D3H2LN cell-derived EVs did not efficiently promote the migration of low-metastatic D3H1 cells across BBB compared to BMD2a- and BMD2b cell-derived EVs. These results indicated that the EVs derived from brain metastasis breast cancer cells affected the extravasation of cancer cells to the brain parenchyma side across BBB.

(Example 8) Examination of Effect of EVs on Permeability of BBB

To determine whether EVs derived from brain metastatic cancer cells directly affects BBB disruption, whether addition of EVs in the in vitro BBB model disrupts BBB or not was examined. EVs were prepared according to the description in Example 5. Four days after thawing the in vitro BBB model, purified EVs derived from D3H2LN, BMD2a, and BMD2b cells or PBS (negative control) was added. Before the addition of the EVs and 24 hours after the addition, transendothelial electrical resistance (TEER) was measured to measure the strength of tight junction of the brain capillary endothelial cells, according to the method described in Example 2. All assays were performed in triplicate.

Furthermore, a permeability test using NaF was conducted according to the method described in Example 2 (2) to measure the permeability of BBB. 24 hours after the addition of purified EVs derived from D3H2LN, BMD2a, and BMD2b cells, NaF was added. NaF moved across BBB was measured with a fluorocytometer. The apparent permeability coefficient (Papp) ($10^{-6}$ cms$^{-1}$) was calculated according to the calculating formula described in Example 2 (2). All assays were performed in triplicate.

Figure 8:
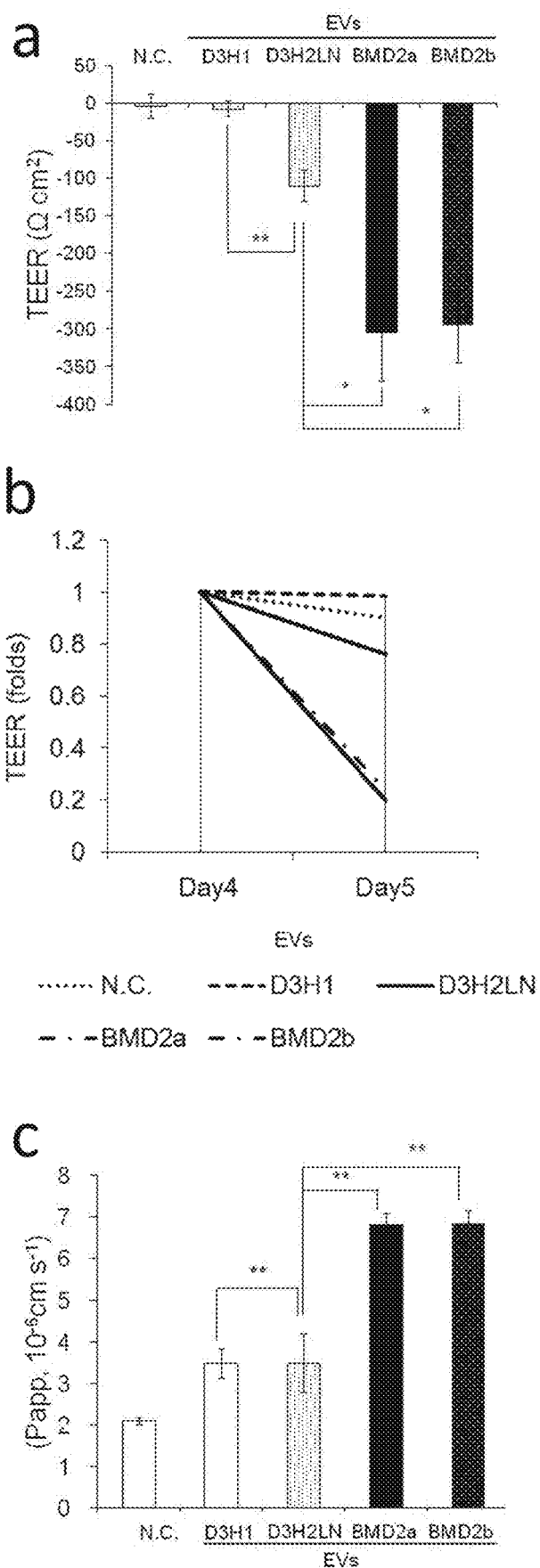
FIG. 8 (a) A graph showing the result of TEER measurement at 24 hours after the addition of EVs. The vertical axis represents the measurement of TEER ($\Omega \cdot cm^2$), the horizontal axis indicates the cells from which the added EVs are derived, which are from the left to the right, negative control (N.C.), D3H1, D3H2LN, BMD2a, and BMD2b cells. The error bars represent standard deviation (SD), * indicates P<0.05, and ** indicates P<0.01. (b) A graph showing changes of TEER between before and 24 hours after the EV addition. The horizontal axis represents the ratio (folds) of the TEER value at 24 hours after the EV addition relative to that before the EV addition. (c) A graph representing the result of the permeability test of BBB measured by NaF. The vertical axis represents the apparent permeability coefficient (Papp) ($10^{-6}$ $cms^{-1}$). The horizontal axis indicates the cells from which the added EVs was derived, which are from the left to right, negative control (N.C.), D3H1, D3H2LN, BMD2a, and BMD2b cells.

The measured TEER values are illustrated in FIG. 8a and the relative changes in TEER between before and after the addition of EVs are illustrated in FIG. 8b. TEER values in the BMD2a and BMD2b cell-derived EVs administrated groups were significantly decreased compared to that in the D3H2LN cell-derived EVs administrated group (P<0.05) and the D3H1 cell-derived EVs administrated group (P<0.01).

The result of the permeability test is illustrated in FIG. 8c. Both BMD2a and BMD2b cell-derived EVs administrated groups exhibited a clearly high (P<0.01) permeability coefficient (Papp) compared to the D3H2LN cell-derived EVs administrated group (P<0.05) and the D3H1 cell-derived EVs administrated group (P<0.01).

(Example 9) Analysis of Uptake of EV to BBB Constituent Cells

Figure 9:
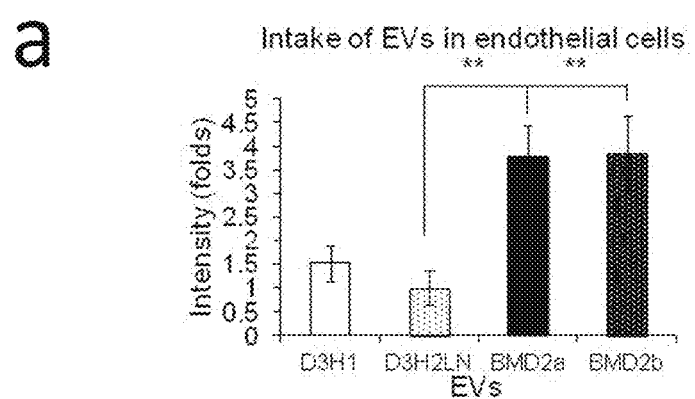
FIG. 9 (a) A graph representing the result of measurement of EV uptake to endothelial cells constituting the in vitro BBB model. The vertical axis represents the fluorescence intensity ratio (folds), relative to D3H2LN cell-derived EVs, of other cell-derived EVs taken up by endothelial cells. The horizontal axis indicates the cells from which the EVs used are derived, which are, from the left to the right, D3H1, D3H2LN, BMD2a, and BMD2b cells. The error bars represent standard deviation (SD), and ** indicates P<0.01. (b) Photographs of Hoechst33342 staining (light blue) of endothelial cells, pericytes, and the astrocytes constituting the in vitro BBB model as well as PKH67 (green) of up-taken EVs, observed with a fluorescence microscope. The cells from which the EVs derived are indicated on the left of the photographs. The bars in the photographs of endothelial cells and pericytes indicate 20 μm. The bar in the photographs of astrocytes indicates 100 μm.
Figure 9:
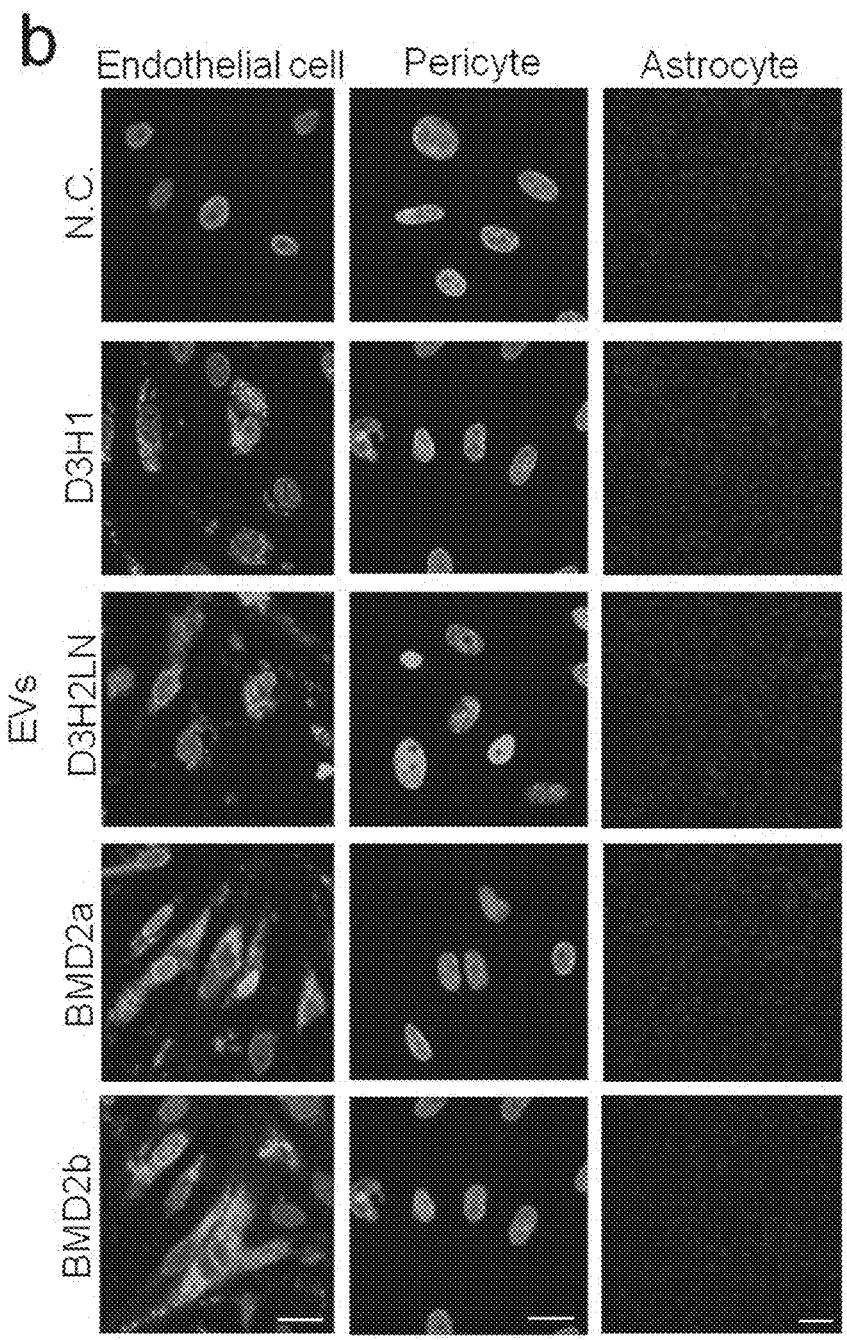

To confirm that EVs are taken up to BBB configuration cell, EVs were added to the in vitro BBB model and examined the uptake by the BBB constituent cells. All assays were performed in triplicate.
(1) Labeling of EV with PKH67
Purified EVs derived from D3H1, D3H2LN, BMD2a, and BMD2b cells prepared by the method in Example 4 were labelled with PKH67 green fluorescent labeling kit (Sigma Aldrich, Mo., USA). EVs were reacted with 2 µM PKH67 for 5 minutes and washed using a 100 kDa filter (Microcon YM-100, Millipore) five times to remove excess dye.
(2) Uptake of EVs into Cells in In Vitro BBB Model
According to the method described in Example 8, the labelled EVs or PBS (negative control) was added to the upper surface side in the in vitro BBB model, which was cultured at 37° C., 5% $CO_2$ for 24 hours. Brain capillary endothelial cells, brain pericytes, and astrocytes were confirmed by Hoechst33342 staining.
(3) Result
The result of measurements of uptake of EVs to BBB constituent cells is illustrated in FIG. 9a and FIG. 9b. All cancer cell-derived EVs were taken up by the endothelial cells, but little uptake to pericytes and astrocyte was observed. The observation that EVs derived from BMD led to the highest fluorescence intensity in endothelial cells revealed the tropism of EVs derived from BMD cells to the cerebrovascular endothelial cells.

(Example 10) Analysis of Mechanisms of BBB Destruction by EVs

To examine the mechanisms of BBB destruction by EVs, EVs were added to the in vitro BBB model and examined the change of molecular behaviors in BBB constituent cells. All assays were performed in triplicate.
(1) Localization of Tight Junction Proteins in Endothelial Cells after the EV Addition
Purified EVs derived from D3H1, D3H2LN, BMD2a, and BMD2b cells prepared by the method in Example 4 or PBS (negative control) was added and, 24 hours later, Claudin-5, Occludin, ZO-1, or N-cadherin in the endothelial cells in the in vitro BBB model was fluorescently immunostained with actin filaments to examine whether the localization is changed using a method similar to that in Example 2 (2).
(2) Change of Tight Junction Protein Levels Etc. In Endothelial Cells after EV Addition
Proteins were isolated from each cell line using M-PER (Thermo Scientific, MA, USA), separated in Mini-PROTEAN® TGX Gel (4-12%) (Bio-Rad), and electrotransferred onto PVDF membranes (Millipore). The resultant membranes were blocked in Blocking One (Nacalai Tesque, Kyoto, Japan) and then incubated for 1 hour at room temperature with a primary antibody, anti-Claudin-5 antibody (Z43.JK, 1/200, Invitrogen), anti-Occludin antibody (ZMD.481, 1/200, Invitrogen), anti-ZO-1 antibody (H-300, sc-10804, 1/100, Santa Cruz Biotechnology), anti-N-cadherin antibody (3B9, 1/500, Invitrogen), or anti-GAPDH antibody (6C5, 1/1000, Millipore). An HRP-linked anti-mouse IgG secondary antibody (NA931, GE Healthcare) or HRP-linked anti-rabbit IgG secondary antibody (NA934, GE Healthcare) was used at a dilution of 1/2000. The membranes were then made luminescent with ImmunoStar® LD (Wako, Osaka, Japan).

(3) Results

Figure 10:
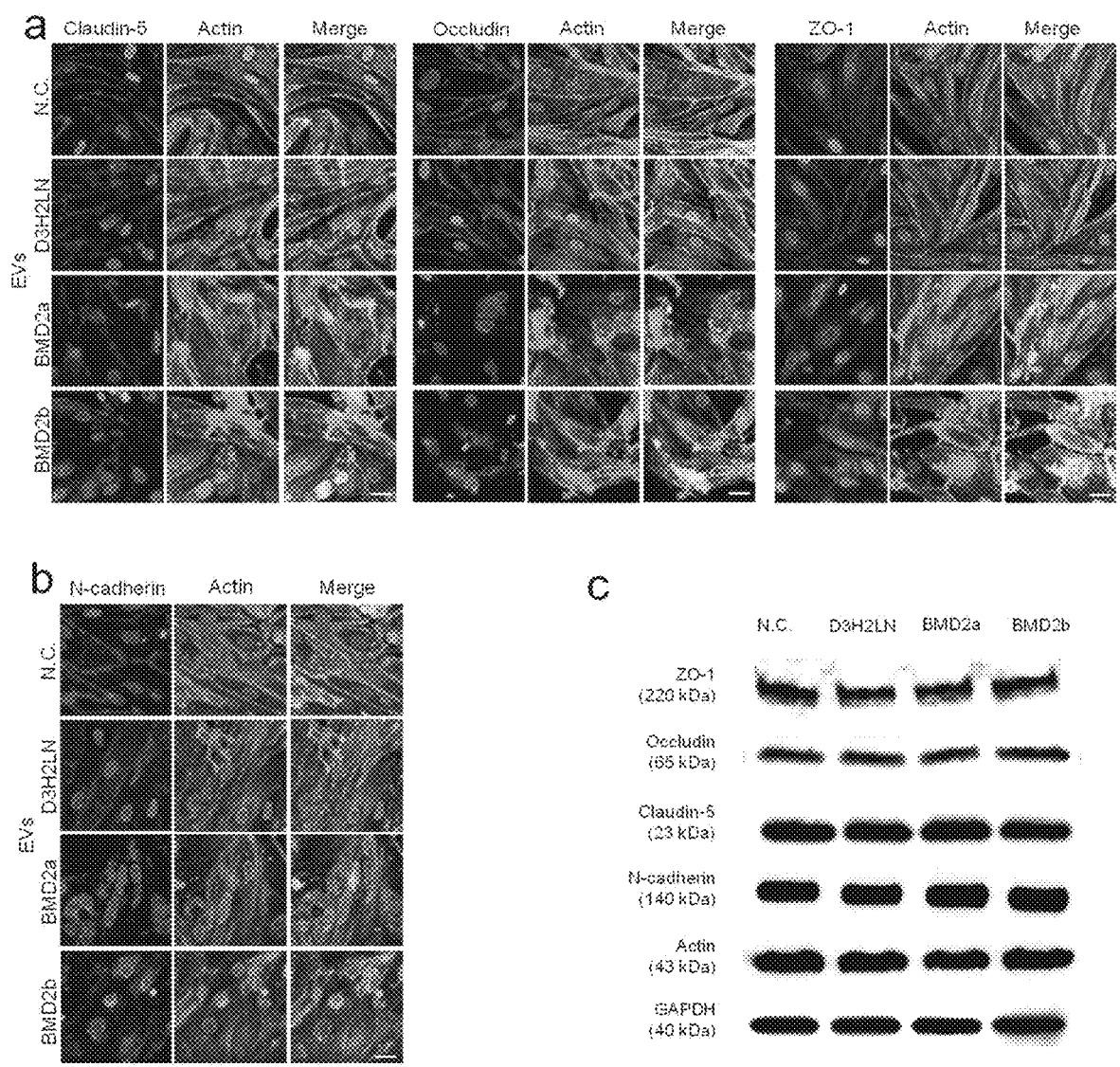
FIG. 10 (a) Photographs of co-immunofluorescence of tight junction proteins (Claudin-5, Occludin and ZO-1) (red) and actin filaments (green) in vascular endothelial cells constituting the in vitro BBB model after the addition of EVs derived from D3H2LN, BMD2a, and BMD2b cells. The bars indicate 20 μm. (b) Photographs of co-immunofluorescence of N-cadherin (red) and actin filaments (green) in blood vessel cells constituting the in vitro BBB model after the addition of EVs derived from D3H2LN, BMD2a or BMD2b cells. The bars indicate 20 μm. (c) A photograph of Western blot analysis on tight junction proteins, N-cadherin, Actin, and GAPDH (internal control) in proteins recovered from endothelial cells treated with PBS (negative control: N.C.) or EVs derived from D3H2LN, BMD2a, or BMD2b cells.

The results of localization of the tight junction proteins in the endothelial cells in the in vitro BBB model are illustrated in FIG. 10a and FIG. 10b. The tight junction proteins and the N-cadherin were localized on the cell membrane surface of the endothelial cells treated with PBS or the EVs derived from D3H2LN cells. However, the tight junction proteins and the N-cadherin were found in the cytoplasm in the cells treated with the EVs derived from BMD2a and BMD2b. Moreover, the treatment of cerebrovascular endothelial cells with the EVs derived from BMD2a and BMD2b had no effect on the expression of the tight junction proteins, N-cadherin, and actin (FIG. 10c). Thus, it was revealed that cancer-derived EVs changes the localization of tight junction proteins, N-cadherin, and actin filament without affecting the expression thereof.

(Example 11) Examination of Effect on Blood-Brain Barrier Permeability of EVs in In Vivo Since the results of the in vitro BBB model tests demonstrated that cancer cell-derived EVs are taken up by endothelial cells and increase the permeability of BBB, in vivo permeability tests were conducted to examine whether they also have the effect on the blood ability barrier in vivo. Purified EVs derived from D3H2LN cells (control) and BMD2a cells were labelled by XenoLight DiR fluorescent staining. The labelled EVs were injected into the tail vein of mice and, 6 hours later, Tracer-653, a dye for in vivo blood vessel permeability tests, was injected into the mice for monitoring BBB disruption.

Figure 11:
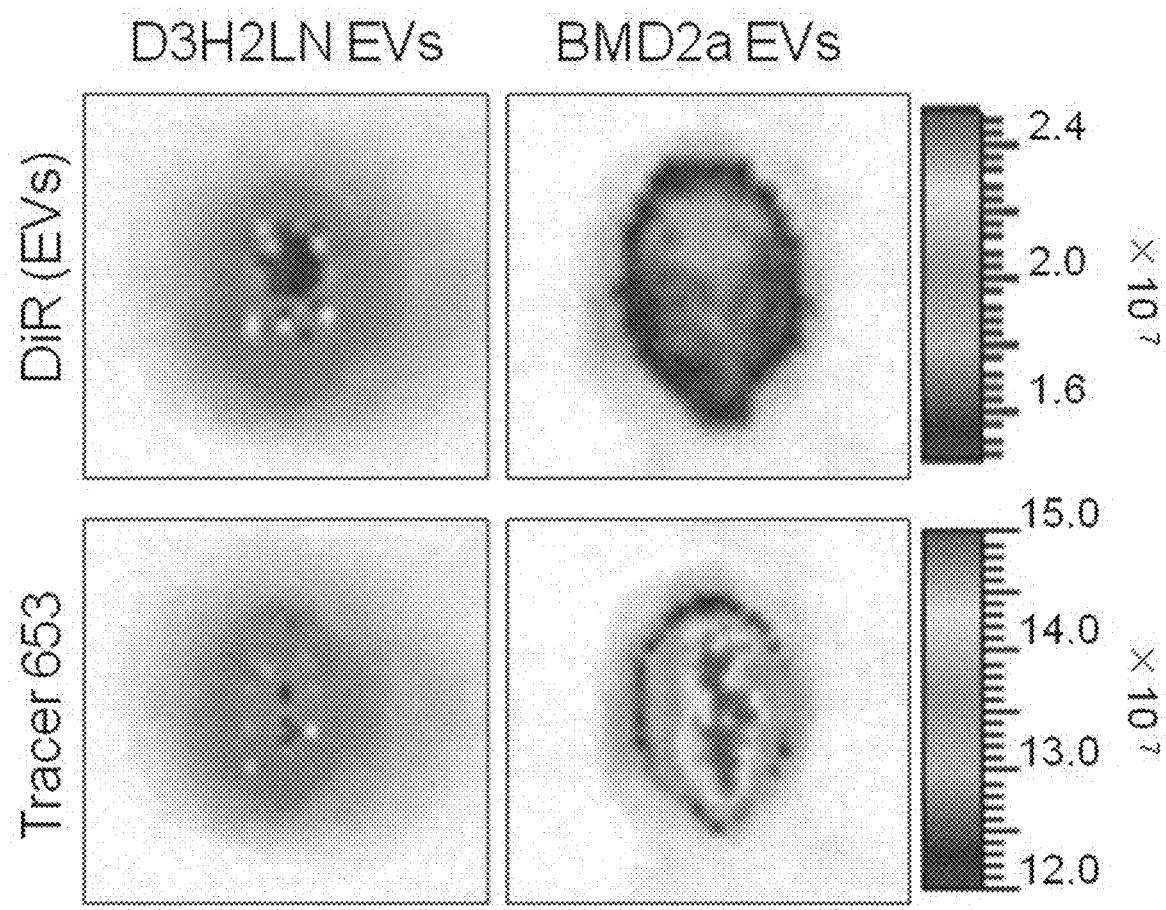
FIG. 11 Fluorescence image photographs of a brain of a mouse administered D3H2LN (control) or BMD2a cell derived EVs. The fluorescence intensity of the upper panels represents DiR-labelled EVs up-taken by a mouse brain. The fluorescence intensity of the lower panels represents the blood vessel permeability of a mouse brain.

The upper panels in FIG. 11 illustrate the intake of EVs and the lower panels illustrate the permeability of brain blood vessels. As illustrated in the upper panels of FIG. 11, BMD2a cell-derived EVs were more incorporated within the brains of mice than were D3H2LN cell-derived EVs. As illustrated in the lower panels of FIG. 11, BMD2a cell-derived EV-treated mice exhibited greater permeability of brain blood vessels compared to D3H2LN cell-derived EV-treated mice.

(Example 12) Effect of EVs on Cancer Metastasis In Vivo

To examine whether increase in in vivo brain blood vessel permeability by EVs, confirmed in Examples above, actually has an effect on brain metastasis, cancer cells were injected into EV-treated mice and whether brain metastasis occurs or not was examined. Purified EVs (5 µg/animal for each) derived from D3H2LN cells (control) or BMD2a cells or PBS (negative control) were injected in the tail vein of 9 animals per group of C.B-17/Icr-scid/scid mice (Day 0). 24 hours later (Day 1), the D3H2LN breast cancer cell line ($2\times10^5$ cells) was injected in the left cardiac ventricle of each mice. 18 days later (Day 19), brain metastasis of cancer cells was observed by intraperitoneal luciferin injection and bioluminescence in vivo imaging using IVIS Spectrum (Caliper Life Science, Hopkinton, Mass., USA). Evaluation was made by measuring photon intensity in the brain from the obtained images. Significant difference was evaluated by Mann Whitney one-tailed testing. Brain metastasis was also confirmed by hematoxylin and eosin (HE) staining and immunofluorescence staining for human vimentin.

Figure 12:
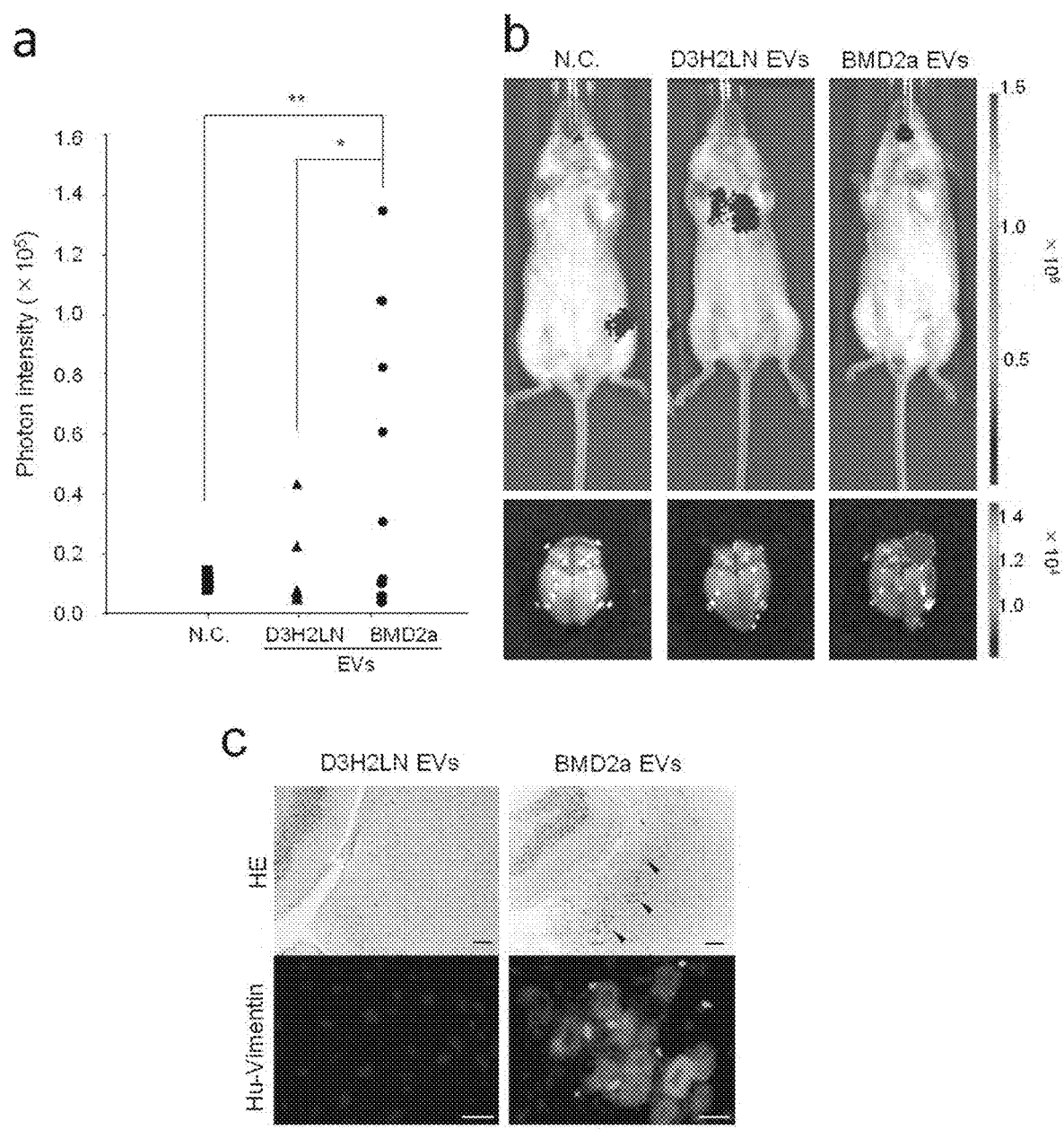
FIG. 12 (a) A graph showing distribution of photon intensity in the mouse brain. The vertical axis represents photon intensity ($\times 10^5$). The horizontal axis indicates each mouse group, which are from the left to the right, negative control (N.C.), the D3H2LN-derived EVs administrated group (D3H2LN), and the BMD2a-derived EVs administrated group (BMD2a). * indicates P<0.05 and ** indicates P<0.01. (b) Photographs showing bioluminescence image of cancer cell metastasis in mice into which cancer cells were transplanted after administration of PBS (negative control) (N.C.) (left), EVs derived from D3H2LN (D3H2LN EVs) (middle), and EVs derived from BMD2a (BMD2a EVs) (right). The upper panels are bioluminescence images of the whole body of the mice, and the lower panels are bioluminescence images of a mouse brains. (c) Photographs of sections from a mouse brain cerebral cortex. The upper panels are photographs of hematoxylin and eosin (HE) staining and the arrowheads indicate metastatic cancer cells. The bars at the lower right corner in the photographs indicate 100 μm. The lower panels are image photographs of anti-human vimentin immunofluorescence staining and the bars at the lower right corner in the photographs indicate 20 μm.

In the BMD2a-derived EVs administrated group, brain metastasis in 5 out of 9 animals (55.6%), which is clearly higher than brain metastasis in the D3H2LN cell-derived EVs administrated group (brain metastasis in 1 out of 9 animals: 11.1%) and the PBS administrated group (brain metastasis in 0 out of 9 animals: 0%), was found. According to the result of fluorescence intensity measurement, there were clearly more invading and metastasizing cancer cells in brains in the BMD2a-derived EVs administrated group compared to those in other groups (FIG. 12a, b, $p<0.05$). HE staining also confirmed brain metastasis (FIG. 12c). As indicated by these results, it was revealed that increase of the brain blood vessel permeability by EVs increases brain metastasis (Example 13) Elucidation of Molecule Responsible for Change of Blood-Brain Barrier Permeability by EVs To elucidate the molecular mechanisms by which EVs changed the permeability of the blood-brain barrier, miRNA contained in EVs derived from D3H2LN, BMD2a, and BMD2b cells was analyzed.

Total RNA was extracted from EVs using the QIAzol reagent and the miRNeasy Mini Kit (both Qiagen). The quality and quantity of the RNA were determined using NanoDrop ND-1000 spectrophotometer (Thermo Fisher Scientific Inc.) and Agilent Bioanalyzer (Agilent Technologies) according to the recommended methods. The obtained total RNA was labelled with cyanine 3 (Cy3) using miRNA Complete Labeling and Hyb Kit (Agilent Technologies) according to the manufacturer's instructions. More specifically, 100 ng of total RNA was dephosphorylated by reacting for 30 minutes at 37° C. using Calf Intestinal Alkaline Phosphatase (CIP) Master Mix. The dephosphorylated RNA was denatured with DMSO by incubation for 5 minutes at 100° C. The RNA was then immediately transferred on ice and incubated for 2 minutes. The resultant reaction products were mixed with Ligation master mix for T4 RNA Ligase and Cy3-pCp (Cyanine 3-Cytidine biphosphate) and incubated for 2 hours at 16° C. The labelled RNA was dried using vacuum concentrator at 55° C. for 1.5 hours. Cy3-pCp-labelled RNA was hybridized on Agilent SurePrint G3 Human miRNA 8×60K Rel. 19 microarray (design ID: 046064) at 55° C. for 20 hours. There are a total of 2,006 miRNA probes on the microarray without control probes. After washing, the microarray was scanned using an Agilent DNA microarray scanner. Intensity values of each scanned feature were quantified using Agilent Feature Extraction software version 10.7.3.1, which performs background subtractions. Only using features that were flagged as no errors (Detected flags), the expression analysis was performed with Agilent GeneSpring GX version 12.6.1. Features that were not positive, not significant, not uniform, not above background, saturated and population outliers (not detected flags) were excluded. In this experiment, the significant differences of gene expression were identified by applying more than 2-fold change in signal intensity.

Figure 13:
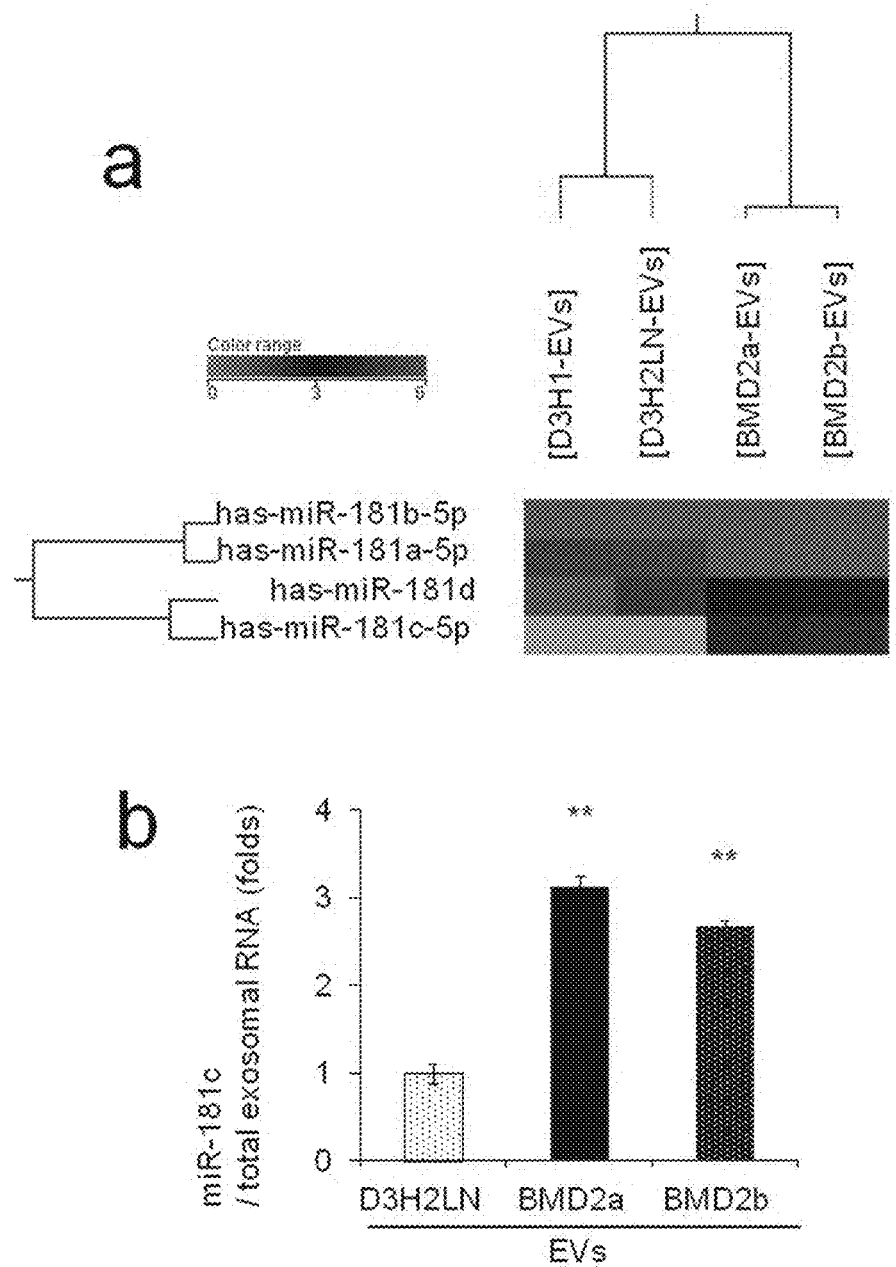
FIG. 13 (a) A heat map of expression levels of miR-181c in cancer cell-derived EVs. (b) A graph showing the ratio (folds) of the rate of an amount of miR-181c to an amount of total RNA (miR-181c/(total exosome RNA)) in EVs isolated from BMD2a and BMD2b cells as compared with the rate of miR-181c/(total exosome RNA) in EVs derived from D3H2LN cells. The vertical axis represents the ratio (folds) of the rate of the amount of miR-181c to the amount of total RNA in isolated EVs from each cell as compared with the rate (which is set to be 1) of the amount of miR-181c to the amount of total RNA in EVs isolated from D3H2LN cells. For BMD2a cell and BMD2b cell, the error bars represent standard deviation (SD) and ** indicates P<0.01 as compared with EVs derived from D3H2LN cells.

In addition to miRNA, proteins contained in EVs derived from D3H2LN, BMD2a, and BMD2b cells were analyzed. However, any candidate protein characteristic of BMD2a and BMD2b cells was not found (not illustrated). As a result of the miRNA analysis, miR-181c was found to be significantly upregulated in BMD2a cell- and BMD2b cell-derived EVs compared to EVs derived from D3H2LN cells (FIG. 13a, FIG. 13b). Therefore, to confirm whether miR-181c is expressed in D3H2LN, BMD2a, and BMD2b cells, intracellular miR-181c was detected. As a result, any significant difference in expression of miR-181c was not confirmed in any of D3H2LN cells, BMD2a cells, and BMD2b cells (not illustrated).

(Example 14) Evaluation of Effect of miR-181c on BBB

Figure 14:
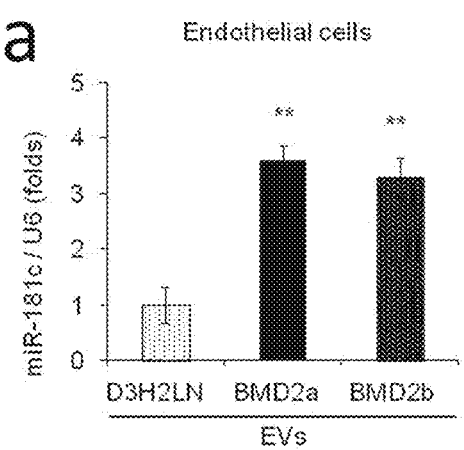
FIG. 14 (a) A graph showing a change in amount of miR-181c in vascular endothelial cells of in vitro BBB model. The vertical axis indicates the ratio (folds) of the amount of miR-181c in the RNAs recovered from vascular endothelial cells of the in vitro BBB model after adding cancer cell-derived EVs to the in vitro BBB model, relative to the amount of miR-181c contained in the vascular endothelial cells to which EVs derived from D3H2LN cells were added, wherein the amounts of miR-181c are corrected by that of RNU6. The horizontal axis indicates the cells from which the EVs added to the in vitro BBB model were derived from, which are D3H2LN, BMD2a, and BMD2b cells from the left to the right. For BMD2a and BMD2b cells, the error bars represent standard deviation (SD) and  indicates P<0.01 as compared with EVs derived from D3H2LN cells. (b) A graph of the TEER measurement at 24 hours after transfecting the vascular endothelial cells of the in vitro BBB model with miR-181c. The vertical axis indicates the measurement of TEER ($\Omega \cdot cm^2$) and the horizontal axis indicates the transfected microRNAs, which are negative control (N.C.) and miR-181c, from the left to the right. The error bars represent standard deviation (S.D.), and  indicates P<0.01. (c) Photographs of the co-immunofluorescence of tight junction proteins (Claudin-5, Occludin, and ZO-1), N-cadherin (red), and actin filaments (green) in vascular endothelial cells constituting the in vitro BBB model after the transfection with the negative control (N.C.) or miR-181c. The bar indicates 20 μm. (d) A photograph illustrating Western blot analysis of tight junction proteins, N-cadherin, actin, and GAPDH (internal control), using proteins recovered from the vascular endothelial cells constituting the in vitro BBB model, which had been transfected with the negative control (N.C.) or miR-181c.
Figure 14:
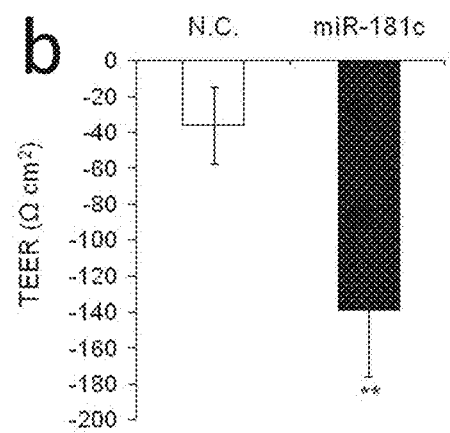
Figure 14:
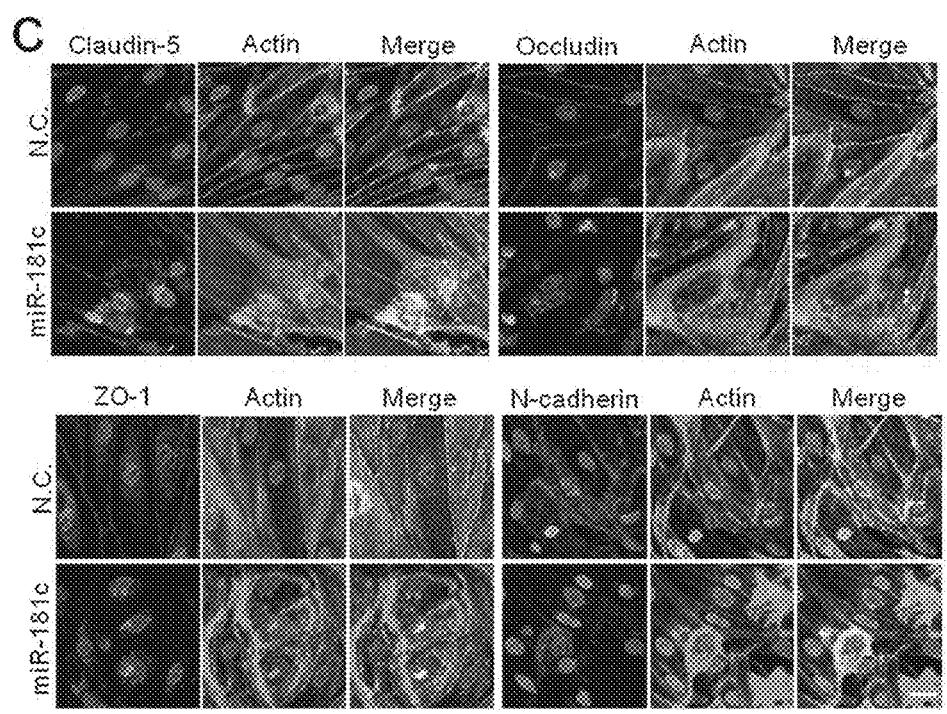
Figure 14:
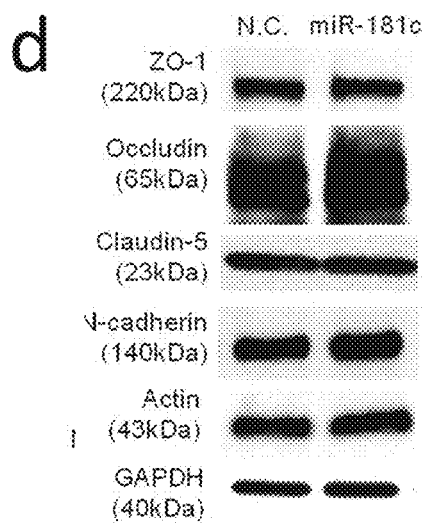

The foregoing results suggested that the BBB destruction by cancer cell-derived EVs involves miR-181c contained in EVs taken up by the endothelial cells. Therefore, the abundance of miR-181c in the endothelial cells after the addition of the EVs was examined to study the effect of miR-181c on BBB. Changes of permeability and behaviors of tight junction proteins were also examined using the in vitro BBB model containing the endothelial cells into which miR-181c had been introduced.
(1) Change of miR-181c Abundance in Endothelial Cells by Addition of EVs To evaluate the effect of miR-181c on BBB, EVs isolated from BMD2a and BMD2b was added to endothelial cells and the change of miR-181c abundance was examined. EVs were prepared according to the description in Example 5. Four days after thawing the in vitro BBB model, purified EVs derived from D3H2LN, BMD2a, and BMD2b cells or PBS (negative control) were added. 24 hours after the addition of EVs, the expression of miR-181c in endothelial cells was measured. All assays were performed in triplicate.
(2) Effect of Change of miR-181c Abundance in in Endothelial Cells To further examine the effect of change of miR-181c abundance on endothelial cells, synthetic miR-181c was introduced into the endothelial cells constituting the in vitro BBB model. Transendothelial electrical resistance (TEER) was measured according to the method described in Example 2 (3). The localization and expression levels of tight junction proteins, N-cadherin, and actin were detected according to the method described in Example 10. Endothelial cells into which miR-181c was not introduced was used as a negative control.
(3) Results The abundance of miR-181c in the endothelial cells was significantly increased by the addition of EVs derived from BMD2a and BMD2b (FIG. 14a). The transfection of miR-181c significantly decreased the value of TEER in the in vitro BBB model (FIG. 14b). While tight junction proteins, N-cadherin and actin localized on the membrane in the negative control group, the localization had been changed to the cytoplasm in miR-181c-transfected cells (FIG. 14c). Furthermore, it was found that the expression of tight junction proteins, N-cadherin, and actin was not affected by the transfection of miR-181c into brain blood vessel endothelial cells (FIG. 14d).

(Example 15) Measurement of Serum miR-181c in Brain Metastasis Breast Cancer Patients To confirm whether there is actually miR-181c in EVs in the blood of brain metastasis breast cancer patients or not, EVs were purified from sera from brain metastasis breast cancer patients and the expression of miR-181c was examined. Sera from 56 breast cancer patients (10 brain metastasis patients, 46 non-brain metastasis patients) were collected at National Cancer Center Japan (No. 2013-111). Informed consent was obtained from all the patients. Serum was aliquoted and stored at −80° C. until used, and freeze-thawing was avoided as much as possible after that. EVs were isolated from the sera using Total Exosome Isolation (from sera) (Invitrogen), The total RNA was then isolated from the obtained EVs using the RNeasy Mini Kit (Qiagen). The expression of miRNA was measured by qRT-PCT using RNU6 as an internal control by an already reported method (Kosaka, N. et al. Net. Med., 18:883-891 (2012)). More specifically, the expression levels of miR-181c and RNU6 were measured in a 96-well plate by qRT-PCR using TaqMan® MicroRNA Assays and TaqMan® Universal PCR Master Mix in 7300 Real-Time PCR System (all from Applied Biosystems, CA, USA). All reactions were performed in triplicate.

Figure 15:
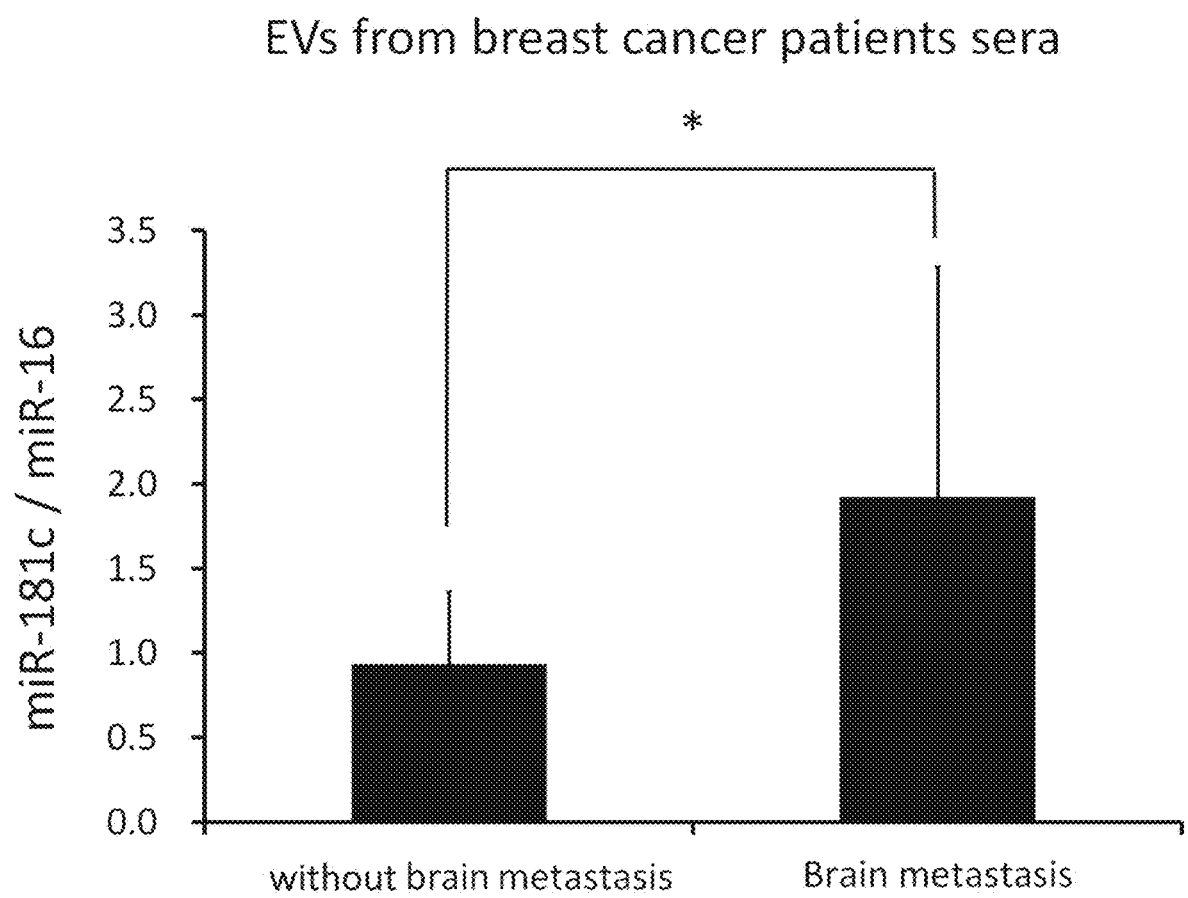
FIG. 15 A graph showing the amount of miR-181c contained in serum EVs derived from patients. The vertical axis indicates the ratio of the amount of miR-181c relative to the amount of miR-16. The left in horizontal axis indicates "without brain metastasis" (n=46) and the right indicates "Brain metastasis" (n=10). * indicates P<0.05. The miR-181c levels were assessed by t-test.
Figure 16:
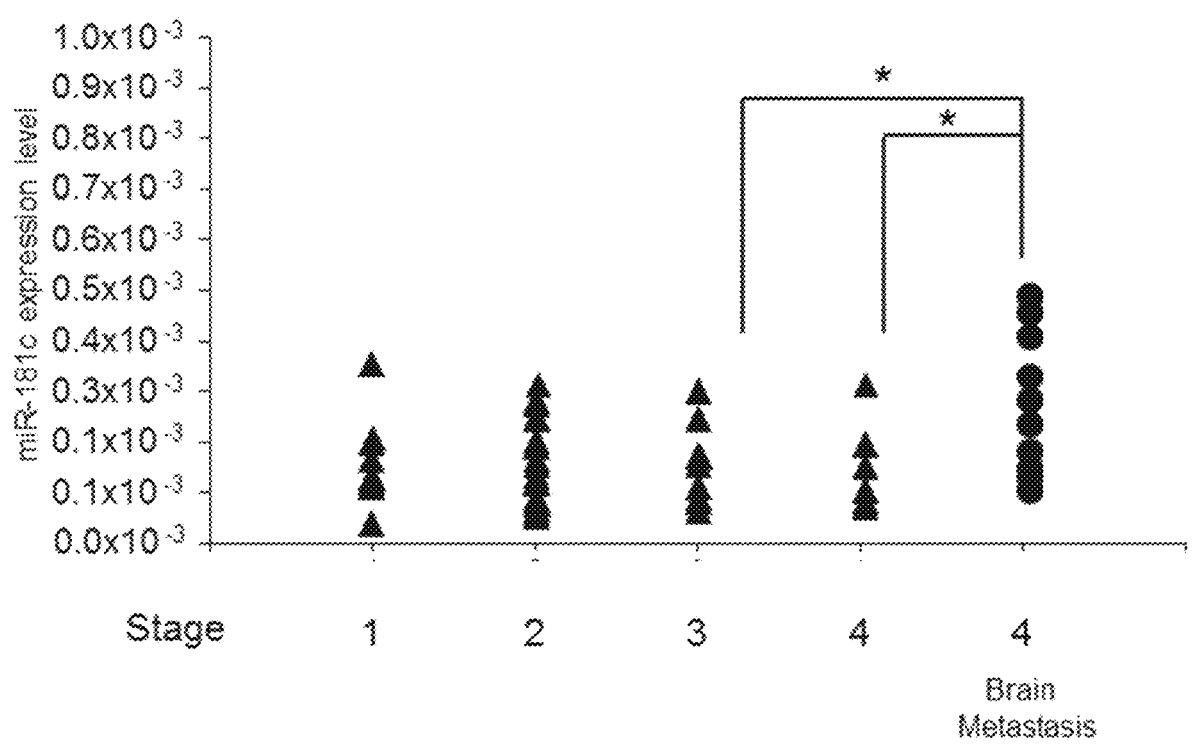
FIG. 16 A graph showing the distribution of the amount of miR-181c contained in sera of breast cancer patients. The vertical axis indicates the abundance of miR-181c corrected by the abundance of miR-16 ($\Delta\Delta Ct$ value). The horizontal axis indicates the stage of breast cancer using the TNM staging. * indicates significant differences (P<0.05) in Mann-Whitney U test between the patient group with brain metastasis and the patient groups in Stage 3 and in Stage 4 without brain metastasis.

Significantly more miR-181 was present in the EVs obtained from sera from the brain metastasis patients compared to the non-brain metastasis patients (P<0.05, T test; FIG. 15). There was no difference in the serum miR-181c abundance among stages in the non-brain metastasis breast cancer patients (FIG. 16). In the comparison between same IV patients, there was a significant difference between the brain metastasis and the non-brain metastasis patients (P<0.05) and the miR-181c level was clearly higher in EVs derived from the sera from brain metastasis patients. This suggested that the secretion of miR-181c to blood contributes to brain metastasis in real patients as well.

The foregoing results indicated that EVs derived from brain metastatic cancer cells induce the abnormal localization of tight junction proteins by transferring miR-181c into endothelial cells, which results in the destruction of the cell-cell contact.

(Example 16) Search of Target of miR-181c in Endothelial Cells

To elucidate the mechanisms of BBB destruction by miR-181c, search for the target of miR-181c in the endothelial cells was conducted. The gene expression in endothelial cells transfected with a negative control or miR-181c and the gene expression in endothelial cells after the addition of EVs derived from in BMD2a, BMD2b, or D3H2LN cells were analyzed.

The total RNA from respective endothelial cells was isolated using the QIAzol reagent and the mirRNeasy Mini Kit (both Qiagen). The quality and quantity of the RNA were determined using NanoDrop ND-1000 spectrophotometer (Thermo Fisher Scientific Inc.) and Agilent Bioanalyzer (Agilent Technologies) according to the recommended methods. The obtained total RNA was labelled with cyanine 3 (Cy3) during amplification using Low Input Quick Amp Labeling Kit, one-color (Agilent Technologies) according to the manufacturer's instructions. More specifically, 100 ng of total RNA was reverse-transcripted into double strand complementary DNA (cDNA) using poly dT-T7 promoter primers. The primers, the template RNA, and a quality control transcription product of known concentration and quality were first denatured at 65° C. for 10 minutes and then incubated for 2 hours at 40° C. with 5× first strand buffer, 0.1 M dithiothreitol, 10 mM deoxynucleotide triphosphate mixture, and AffinityScript RNase Block Mix, which was then incubated with AffinityScript enzyme at 70° C. for 15 minutes. Using the cDNA product as template, fluorescent complementary RNA (cRNA) was produced by in vitro transcription. The cDNA product was mixed with transcription master mix in the presence of T7 RNA polymerase and Cy3-labeled CTP (cytidine 5'-triphosphate) and incubated at 40° C. for 2 hours. The labelled cRNA was purified using RNeasy Mini Spin Columns (Qiagen) and eluted with 30 mL of nuclease-free water. After the amplification and labeling, the quantity of the cRNA and incorporation of cyanine were determined using NanoDrop ND-1000 spectrophotometer (Thermo Fisher Scientific Inc.) and Agilent Bioanalyzer (Agilent Technologies). In each hybridization, 0.6 μg of Cy3-labeled cRNA was fragmented and hybridized with Agilent Cynomolgus macaque Gene Expression Profiling Array (design ID: 028520) at 65° C. for 17 hours. There are a total of 12,243 miRNA probes on the microarray without control probes. After washing, the microarray was scanned using an Agilent DNA microarray scanner. Intensity values of each scanned feature were quantified using Agilent Feature Extraction software version 10.7.3.1, which performs background subtractions. Only using features that were flagged as no errors (Detected flags), the normalization was performed with Agilent GeneSpring GX version 12.6.1 (for each tip: normalization for third quartile shift; for each gene: normalization for the median of all samples). Features that were not positive, not significant, not uniform, not above background, saturated and population outliers (Compromised and not detected flags) were excluded. Changed transcription products were quantified by using the comparison method. In this experiment, the significant differences of gene expression were identified by applying 2-fold change in signal intensity.

Figure 17:
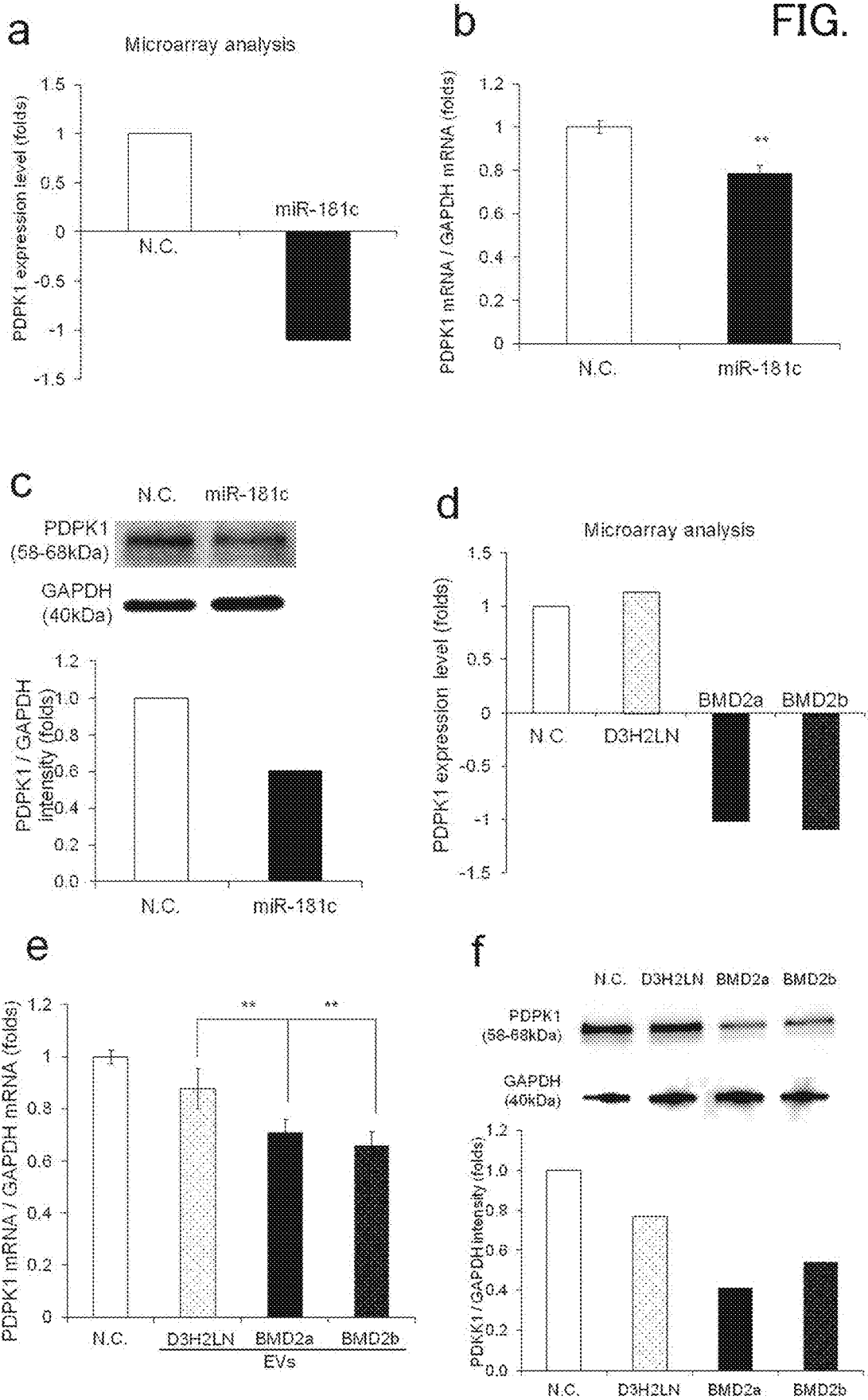
FIG. 17 (a) The ratio of PDPK1 expression amounts in a microarray analysis. After transfecting vascular endothelial cells constituting the in vitro BBB model with the negative control (N.C.) or miR-181c, RNAs recovered from the vascular endothelial cells were analyzed with microarray. The vertical axis indicates a ratio of an amount of PDPK1 expression by each cells relative to an amount of PDPK1 expression by cells transfected with the negative control (N.C.) which is set to be 1. The horizontal axis indicates the micro RNA used for the transfection, N.C. and miR-181c from the left to the right. (b) The expression amount of PDPK1 mRNA expression in vascular endothelial cells constituting the in vitro BBB model. After transfecting the vascular endothelial cells with the negative control (N.C.) or miR-181c, RNAs are recovered from the vascular endothelial cells, and the amount of PDPK1 mRNA contained in the RNA was analyzed by RT-PCR. The vertical axis indicates the value of the amount of PDPK1 mRNA corrected by the amount of GAPDH mRNA (ΔΔCt value) which is set to be 1. The horizontal axis indicates the microRNAs used for the transfection, N.C. and miR-181c from the left to the right.  indicates $P<0.01$. (c) A photograph of Western blot analysis on PDPK1 and GAPDH (internal control), using proteins recovered from the vascular endothelial cells constituting the in vitro BBB model transfected with the negative control (N.C.) or miR-181c. The graph indicates the value of the luminescence intensity of PDPK1 corrected by the luminescence intensity of GAPDH in Western blot analysis. (d) The ratio of PDPK1 expression levels in a microarray analysis. After adding negative control (N.C.), D3H2LN cell-derived EVs, BMD2a cell-derived EVs, or BMD2b cell-derived EVs to the vascular endothelial cells constituting the in vitro BBB model, RNAs were recovered from the vascular endothelial cells and analyzed by microarray analysis. The vertical axis indicates the ratio of the expression amount of PDPK1 relative to the expression amount of PDPK1 by cells treated with the negative control (N.C.), which is set to be 1. The horizontal axis indicates the added EVs, negative control (N.C.), D3H2LN cell-derived EVs, BMD2a cell-derived EVs, and BMD2b cell-derived EVs. (e) The expression levels of PDPK1 mRNA in the vascular endothelial cells constituting the in vitro BBB model. After adding negative control (N.C.), D3H2LN cell-derived EVs, BMD2a cell-derived EVs, or BMD2b cell-derived EVs to the vascular endothelial cells constituting the in vitro BBB model, the amount of PDPK1 mRNA contained in the RNA recovered from the vascular endothelial cells was analyzed by RT-PCR. The vertical axis indicates the ratio of the value (ΔΔCt value) that is the amount of PDPK1 mRNA corrected by the amount of GAPDH mRNA relative to the value of the negative control which is set to be 1. The horizontal axis indicates the added EVs, negative control (N.C.), D3H2LN cell-derived EVs, BMD2a cell-derived EVs, and BMD2b cell-derived EVs.  indicates $P<0.01$. (f) A photograph of Western blot analysis of PDPK1 and GAPDH (internal control) using the proteins recovered from the vascular endothelial cells constituting the in vitro BBB model after adding negative control (N.C.), D3H2LN cell-derived EVs, BMD2a cell-derived EVs, or BMD2b cell-derived EVs. The graph indicates the value of the luminescence intensity of PDPK1 corrected by the luminescence intensity of GAPDH in Western blot analysis.

It was confirmed at both mRNA and protein levels that the expression of 3-phosphoinositide dependent protein kinase-1 (PDPK1) is suppressed in the brain blood vessel endothelial cells transfected with miR-181c compared to the negative control (FIG. 17a-c). Furthermore, it was confirmed at both mRNA and protein levels that the expression of PDPK1 is suppressed compared to the control (endothelial cells treated with EVs derived from D3H2LN cells) in the endothelial cells treated with EVs derived from BMD2a and BMD2b cells (FIG. 17d-f). These results indicated that miR-181c suppresses the expression of PDPK1 in brain blood vessel endothelial cells.

(Example 17) Effect of PDPK1 on Localization of Tight Junction Proteins Etc

To examine the effect of PDPK1 on brain blood vessel endothelial cells, transendothelial electrical resistance (TEER) and the localization and expression of tight junction proteins, N-cadherin, and actin filaments after treatment with PDPK1 siRNA were examined.

25 nM of PDPK1 siRNA (Ambion, ID: 510275) or 25 nM of control siRNA was introduced into brain blood vessel endothelial cells using DharmaFECT transfection reagent (Thermo Scientific) according to the manufacturer' protocol. Transendothelial electrical resistance (TEER) of the in vitro BBB model using the transfected cells after 24 hours was measured according to the method described in Example 2 (3). Moreover, the localization and expression of tight junction proteins, N-cadherin, and actin filaments in the transfected cells after 24 hours were measured according to the method described in Example 10.

Figure 18:
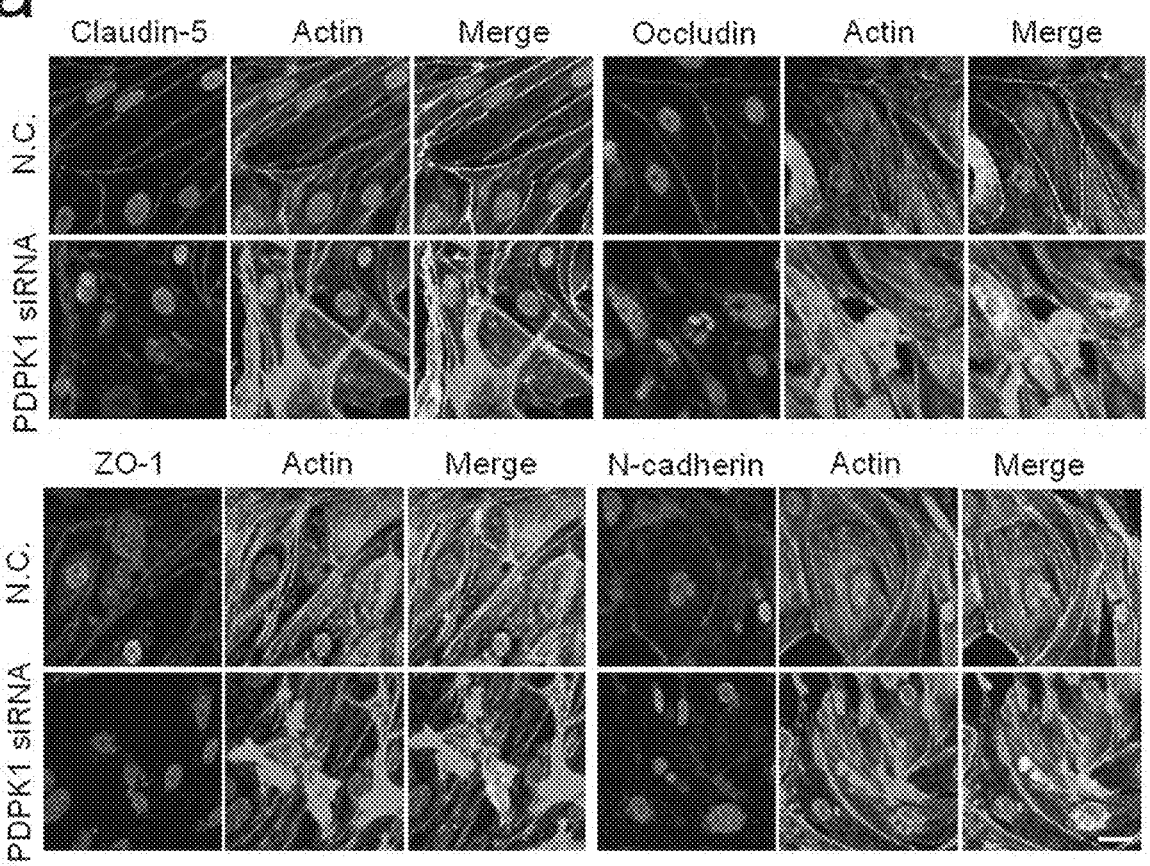
FIG. 18 (a) Photographs of the co-immunofluorescence of tight junction proteins (Claudin-5, Occludin, and ZO-1), N-cadherin (red), and actin filaments (green) in the vascular endothelial cells constituting the in vitro BBB model after transfecting with the negative control (N.C.) or PDPK1 siRNA. The bar indicates 20 μm. (b) A photograph illustrating Western blot analysis of tight junction proteins, N-cadherin, actin, and GAPDH (internal control), using the proteins recovered from the vascular endothelial cells constituting the in vitro BBB model transfected with the negative control (N.C.) or PDPK1 siRNA. (c) A graph of the result of the TEER measurement at 24 hours after the transfection of the vascular endothelial cells of the in vitro BBB model with PDPK1 siRNA. The vertical axis represents the measurement of TEER (Ω, cm$^2$) and the horizontal axis indicates the microRNAs used for the transfection, which are from the left to the right, the negative control (N.C.) and PDPK1 siRNA. The error bars represent standard deviation (S.D.), and ** indicates $P<0.01$.
Figure 18:
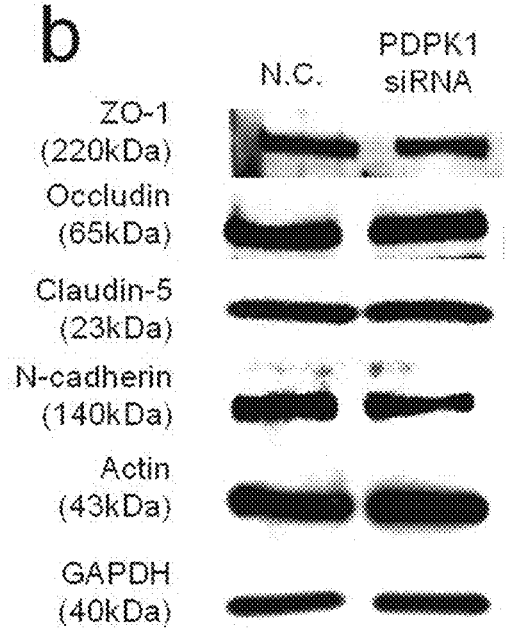
Figure 18:
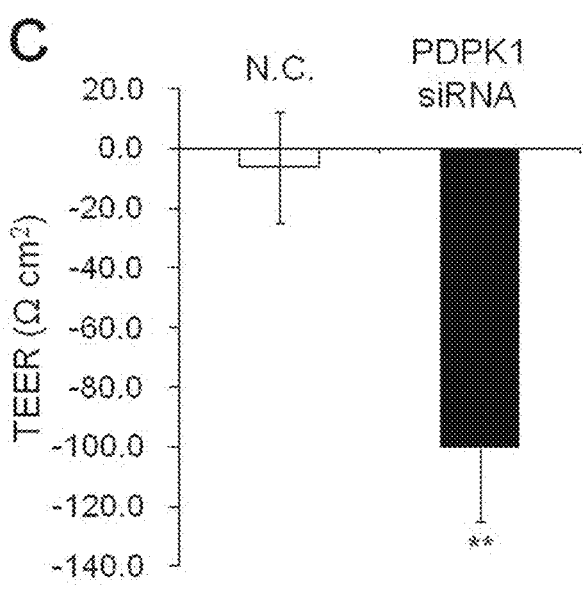
Figure 20:
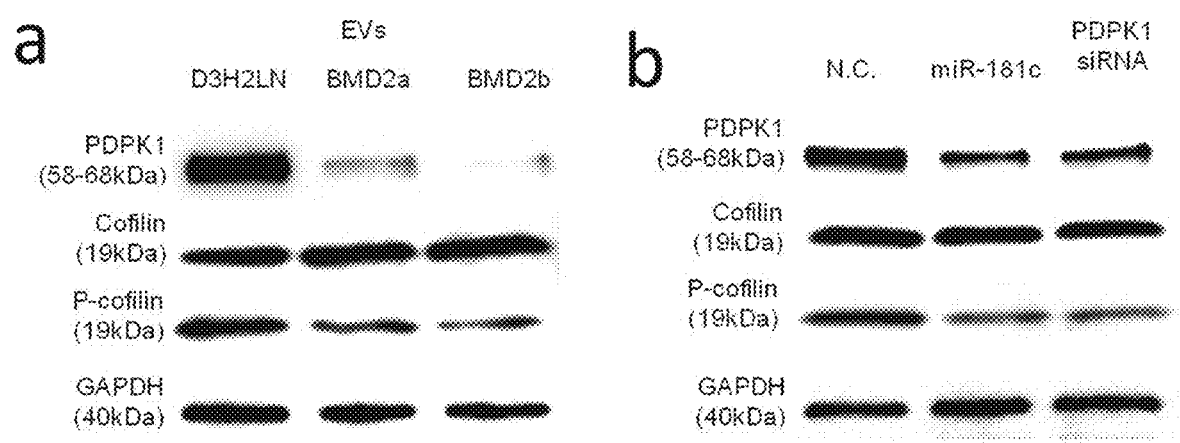
FIG. 20 (a) A photograph of Western blot analysis of PDPK1, Cofilin, phosphorylated Cofilin (P-cofilin), and GAPDH (internal control) using the proteins recovered from the vascular endothelial cells constituting the in vitro BBB model after adding D3H2LN cell-derived EVs, BMD2a cell-derived EVs, and BMD2b cell-derived EVs. (b) A photograph of Western blot analysis of PDPK1, Cofilin, phosphorylated Cofilin (P-cofilin), and GAPDH (internal control) using the proteins recovered from the vascular endothelial cells constituted the in vitro BBB model transfected with the negative control (N.C.), miR-181c, or PDPK1 siRNA.

The introduction of PDPK1 siRNA reduced the expression of PDPK1 protein (see FIG. 20b). While tight junction proteins and N-cadherin were located on the cell membrane in the cells treated with the control siRNA, the localization on the cell membrane had been lost in the PDPK1 siRNA-treated cells (FIG. 18a).

Tight junction proteins, N-cadherin, and actin were found in cytoplasm, which is consistent with the results of the observation of the cells treated with BMD2a cell- or BMD2b cell-derived EVs or the miR-181c-transfected cells. Actin condensation was observed in the PDPK1 siRNA-treated endothelial cells. This phenomenon is also consistent with the results of the cells treated with BMD2a cell- or BMD2b cell-derived EVs or the miR-181c-transfected cells (FIG. 10a, FIG. 10b, FIG. 14c, and FIG. 18a). The expression of tight junction proteins, N-cadherin, and actin was not changed with or without PDPK1 siRNA treatment (FIG. 18b). The transendothelial electrical resistance (TEER) was decreased by the introduction of PDPK1 siRNA (FIG. 18c). These results revealed that the inhibition of PDPK1 changes the localization of tight junction proteins and the N-cadherin and increases the permeability of BBB.

The foregoing results demonstrated that after EVs secreted from brain metastatic cancer cells are taken up by endothelial cells, miR-181c enclosed in the EVs suppresses the expression of PDPK1 in the endothelial cells, thereby changes the localization of tight junction proteins and the N-cadherin, and increases the permeability of BBB.

(Example 18) Confirmation of Suppression of PDPK1 Expression by miR-181c

Furthermore, whether miR-181c can directly suppress the expression of PDPK1 in endothelial cells or not is examined by 3'-untranslated region (3' UTR) luciferase reporter assay using the 3' UTR of the PDPK1 gene (*Macaca*: SEQ ID NO: 14; Human: SEQ ID NO: 15).

The 3' UTR for PDPK1 was obtained by PCR amplification using total RNA extracted from brain blood vessel endothelial cells of the *Macaca fascicularis* as template. The PCR primers used for the 3'UTR amplification are as follows:

```
Forward:
                                     (SEQ ID NO: 16)
AACTCGAGAATGCTGGCTATTGTTGGCCTC Reverse:
                                     (SEQ ID NO: 17)
AAGCGGCCGCAAGATTAAATCACTGACCCAATAG
```

The PCR products were cloned and incorporated into a pGEM-T Easy Vector (Promega, Wis., USA). The amplified 3' UTR was cloned downstream of the *Renilla* luciferase coding region in the psiCHECK-2™ (Promega). An alignment analysis confirmed that there is a sequence complementary to miR-181c in the 3' UTR of PDPK1 (FIG. 19b).

HEK293 cells were seeded at $5 \times 10^4$ cells/well in 96-well plates and cultured overnight. 100 ng of a reporter plasmid along with 100 nM of pre-miR-181c was co-transfected using DharmaFECT Duo transfection reagent (Thermo Scientific).

Cells were collected 24 hours after the transfection and assayed for luciferase activity using EnVision (PerkinElmer, MA, USA). To examine the effect of endogenous miRNA, synthetic precursor miRNA (pre-miR; Ambion®, Invitrogen) was co-transfected as a negative control. All experiments were performed in triplicate.

Figure 19:
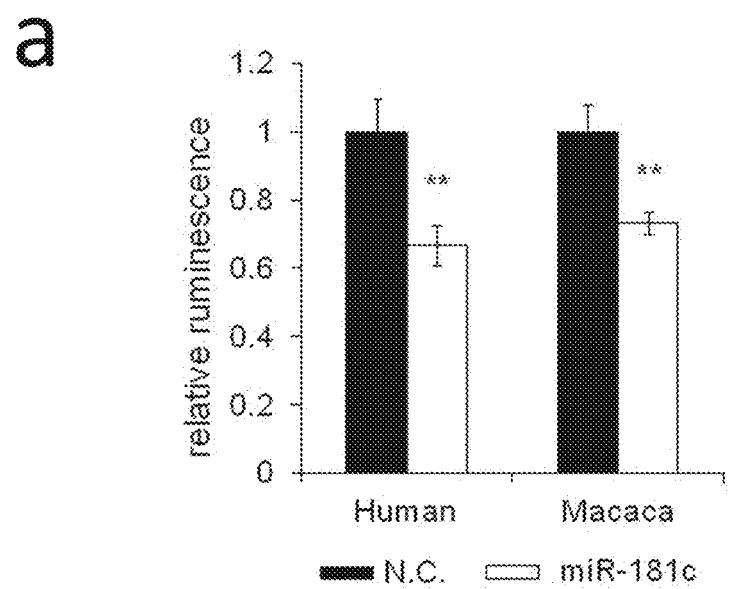
FIG. 19 (a) The result of 3'UTR reporter assay, using the PDPK1 mRNA 3'UTR region derived from Human and *Macaca*. The black bar indicates the result of the negative control (N.C.), and the white bar indicates the result of miR-181c. The values are the ratio relative to the negative control (N.C.) which is set to be 1. ** indicates $P<0.01$.

According to the results obtained by using HEK293 cells, the expression of luciferase, a reporter gene, was decreased by miR-181c (FIG. 19a). These results revealed that PDPK1 is a direct target of miR-181c.

(Example 19) Effect on Cofilin Phosphorylation

PDPK1 is known to be one of the proteins positioning upstream of the pathway that controls Cofilin phosphorylation (Lyle, A. N, et al., Physiology (Bethesda), 21:269-280 (2006); Higuchi, M., et al., Nat. Cell Biol., 10:1356-1364

(2008)). Cofilin is a family of actin-binding proteins, which disassembles actin filaments, that is activated with dephosphorylation. Since actin condensation was observed in the PDPK1 siRNA-treated endothelial cells, whether Cofilin is involve in BBB destruction by miR-181c or not was examined.

Brain blood vessel endothelial cells were treated with EVs derived from D3H2LN, BMD2a, or BMD2b cells. Moreover, miR-181c was introduced into brain blood vessel endothelial cells. Furthermore, brain blood vessel endothelial cells were treated with PDPK1 siRNA according to the method described in Example 17. The expression of phosphorylated Cofilin in each of these cells was analyzed by Western blot analysis.

Samples were obtained from each cell line using M-PER (Thermo Scientific, MA, USA) and loaded in Mini-PROTEAN® TGX Gel (4-12%) (Bio-Rad) and proteins were separated and then electrotransferred onto a PVDF membrane (Millipore). The resultant membranes were blocked in Blocking One (Nacalai Tesque, Kyoto, Japan) and then incubated for 1 hour at room temperature with a primary antibody, anti-PDPK1 antibody (#3062, 1/500, Cell Signaling), anti-Cofilin antibody (D3F9, #5157, 1/1000, Cell Signaling), anti-Phospho-Cofilin antibody (Ser3) (#3311, 1/500, Cell Signaling), or anti-GAPDH antibody (6C5, 1/1000, Millipore). An HRP-linked anti-mouse IgG secondary antibody (NA931, GE Healthcare) or HRP-linked anti-rabbit IgG secondary antibody (NA934, GE Healthcare) was used at a dilution of 1/2000. The membranes were then made luminescent with ImmunoStar®LD (Wako, Osaka, Japan).

Phosphorylation of Cofilin in BMD2a cell- or BMD2b cell-derived EVs-treated cells was decreased compared to that in D3H2LN cell-derived EVs-treated cells (FIG. 20a). Furthermore, phosphorylation of Cofilin in miR-181c or PDPK1 siRNA-treated brain endothelial cells was decreased compared to that in control siRNA treated cells (FIG. 20b). These results revealed that miR-181c in EVs reduces the expression of PDPK1 in brain blood vessel endothelial cells and, as a result, phosphorylation of Cofilin is inhibited, which changes behaviors of actin and causes actin condensation and thereby increases permeability of the blood-brain barrier.

The invention claimed is:

1. A method for increasing the permeability of the blood-brain barrier in a patient having a neurological disease or disorder selected from the group consisting of trigeminal neuralgia, disc herniation, spinal stenosis, Parkinson's disease, spinocerebellar degeneration, epilepsy, Alzheimer's disease and non-Alzheimer type degenerative dementia, comprising:
administering to the patient:
(a) a small interfering ribonucleic acid (siRNA) against the 3-Phosphoinositide Dependent Protein Kinase 1 (PDPK1) gene; or
(b) micro ribonucleic acid (miRNA) miR-181c (SEQ ID NO: 1);
thereby increasing the permeability of the blood-brain barrier in the patient, wherein the patient does not have cancer or a central nervous system (CNS) tumor.

2. A method for delivering a desired active agent into the brain of a patient, comprising:
increasing the permeability of the blood-brain barrier of the patient according to the method of claim 1; and
administering the desired active agent to the patient.

* * * * *